(12) United States Patent
Murase et al.

(10) Patent No.: US 7,763,447 B2
(45) Date of Patent: *Jul. 27, 2010

(54) METHOD OF PRODUCING SUCCINIC ACID WITH BACTERIUM COMPRISING A MODIFIED FUMARATE REDUCTASE GENE OR A MODIFIED SUCCINATE DEHYDROGENASE GENE

(75) Inventors: Makoto Murase, Yokohama (JP); Ryusuke Aoyama, Yokohama (JP); Miki Ikuta, Yokohama (JP); Kenji Yamagishi, Yokohama (JP); Mika Moriya, Kawasaki (JP); Jun Nakamura, Kawasaki (JP); Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 144 days.

This patent is subject to a terminal disclaimer.

(21) Appl. No.: 11/362,931

(22) Filed: Feb. 28, 2006

(65) Prior Publication Data

US 2006/0205048 A1 Sep. 14, 2006

Related U.S. Application Data

(63) Continuation of application No. PCT/JP2004/012404, filed on Aug. 27, 2004.

(30) Foreign Application Priority Data

Aug. 28, 2003 (JP) ............................ 2003-304443

(51) Int. Cl.
  *C12P 7/46* (2006.01)
  *C12N 1/21* (2006.01)
  *C12N 9/02* (2006.01)
  *C12N 15/00* (2006.01)
  *C07K 14/00* (2006.01)
  *C07H 21/00* (2006.01)

(52) U.S. Cl. ............... 435/145; 435/252.3; 435/252.33; 435/252.32; 435/252.31; 435/189; 435/320.1; 530/350; 536/23.2

(58) Field of Classification Search ............... 435/145, 435/252.3, 252.33, 252.32, 252.31, 189, 435/320.1; 530/350; 536/23.2
See application file for complete search history.

(56) References Cited

U.S. PATENT DOCUMENTS

| | | |
|---|---|---|
| 4,489,160 A | 12/1984 | Katsumata et al. |
| 4,500,640 A | 2/1985 | Katsumata et al. |
| 4,514,502 A | 4/1985 | Miwa et al. |
| 4,617,267 A | 10/1986 | Katsumata et al. |
| 5,034,105 A | 7/1991 | Berglund et al. |
| 5,132,456 A | 7/1992 | King et al. |
| 5,142,834 A | 9/1992 | Laclave et al. |
| 5,143,833 A | 9/1992 | Datta |
| 5,143,834 A | 9/1992 | Glassner et al. |
| 5,168,055 A | 12/1992 | Datta et al. |
| 5,185,262 A | 2/1993 | Kohama et al. |
| 5,504,004 A | 4/1996 | Guettler et al. |
| 5,770,435 A | 6/1998 | Donnelly et al. |
| 5,827,700 A | 10/1998 | Felman et al. |
| 5,869,301 A | 2/1999 | Nghiem et al. |
| 5,958,744 A | 9/1999 | Berglund et al. |
| 5,977,331 A | 11/1999 | Asakura et al. |
| 6,265,190 B1 | 7/2001 | Yedur et al. |
| 6,448,061 B1 | 9/2002 | Pan et al. |
| 6,455,284 B1 | 9/2002 | Gokarn et al. |
| 6,696,561 B1 | 2/2004 | Pompejus et al. |
| 2002/0055152 A1* | 5/2002 | Farwick et al. ............... 435/106 |
| 2002/0150999 A1 | 10/2002 | Dusch et al. |
| 2002/0197605 A1 | 12/2002 | Nakagawa et al. |
| 2003/0017559 A1 | 1/2003 | Donnelly et al. |
| 2003/0069354 A1 | 4/2003 | Oyasato et al. |
| 2003/0087381 A1 | 5/2003 | Gokarn et al. |
| 2003/0100079 A1* | 5/2003 | Mockel et al. ............... 435/106 |
| 2005/0196848 A1 | 9/2005 | Dusch et al. |
| 2006/0046288 A1 | 3/2006 | Ka-Yiu et al. |
| 2006/0172401 A1 | 8/2006 | Yamagishi |
| 2006/0228712 A1 | 10/2006 | Nakagawa et al. |
| 2006/0276674 A1 | 12/2006 | Kushiku et al. |

(Continued)

FOREIGN PATENT DOCUMENTS

CA 2322553 4/2001

(Continued)

OTHER PUBLICATIONS

Branden et al., Introduction to Protein Structure, Garland Publishing Inc., New York, p. 247, 1991.*

(Continued)

*Primary Examiner*—Delia M Ramirez
(74) *Attorney, Agent, or Firm*—Greenblum & Bernstein, P.L.C.

(57) ABSTRACT

Succinic acid is produced by allowing a bacterium modified to enhance fumarate reductase activity or cell preparation thereof to react with an organic raw material in a reaction solution containing one of a carbonate ion, a bicarbonate ion, and carbon dioxide gas to generate succinic acid. More preferably, succinic acid is produced by allowing a bacterium modified to enhance activities of fumarate reductase and pyruvate carboxylase and decrease lactate dehydrogenase activity or cell preparation thereof to react with an organic raw material in a reaction solution containing one of a carbonate ion, a bicarbonate ion, and carbon dioxide gas to generate succinic acid. Succinic acid is obtained by collecting the produced succinic acid.

5 Claims, 8 Drawing Sheets

U.S. PATENT DOCUMENTS

| | | |
|---|---|---|
| 2006/0281156 A1 | 12/2006 | Aoyama et al. |
| 2007/0087423 A1 | 4/2007 | Murakami et al. |
| 2007/0154999 A1 | 7/2007 | Fukui et al. |

FOREIGN PATENT DOCUMENTS

| | | |
|---|---|---|
| EP | 0075612 | 4/1983 |
| EP | 0078537 | 5/1983 |
| EP | 0 389 103 | 9/1990 |
| EP | 0410728 | 1/1991 |
| EP | 1 096 013 | 5/2001 |
| EP | 1 108 790 | 6/2001 |
| EP | 1 748 062 | 1/2007 |
| JP | 57-134500 | 8/1982 |
| JP | 57-183799 | 11/1982 |
| JP | 58-035197 | 3/1983 |
| JP | 58-067679 | 4/1983 |
| JP | 58-077895 | 5/1983 |
| JP | 58-192900 | 11/1983 |
| JP | 61-209596 | 9/1986 |
| JP | 62-048394 | 3/1987 |
| JP | 62-238231 | 10/1987 |
| JP | 62-238232 | 10/1987 |
| JP | 62-294090 | 12/1987 |
| JP | 1-191686 | 8/1989 |
| JP | 2-072876 | 3/1990 |
| JP | 2-283289 | 11/1990 |
| JP | 3-072891 | 3/1991 |
| JP | 3-151884 | 6/1991 |
| JP | 3-210184 | 9/1991 |
| JP | 5-260985 | 10/1993 |
| JP | 6-14781 | 1/1994 |
| JP | 7-67683 | 3/1995 |
| JP | 7-304839 | 11/1995 |
| JP | 11-113588 | 4/1999 |
| JP | 11-130852 | 5/1999 |
| JP | 11-196887 | 7/1999 |
| JP | 11-196888 | 7/1999 |
| JP | 11-206385 | 8/1999 |
| JP | 2000-500333 | 1/2000 |
| JP | 2000-037196 | 2/2000 |
| JP | 2001-161386 | 6/2001 |
| JP | 2001-190297 | 7/2001 |
| JP | 2001-514900 | 9/2001 |
| JP | 2002-511250 | 4/2002 |
| JP | 2002-191370 | 7/2002 |
| JP | 2002-291477 | 10/2002 |
| JP | 2003-171448 | 6/2003 |
| JP | 2003-199522 | 7/2003 |
| JP | 2003-235592 | 8/2003 |
| JP | 2003-235593 | 8/2003 |
| JP | 2005-095169 | 4/2005 |
| JP | 2006-238843 | 9/2006 |
| JP | 2006-320208 | 11/2006 |
| WO | 95/34672 | 12/1995 |
| WO | 97/16528 | 5/1997 |
| WO | 99/06532 | 2/1999 |
| WO | 99/09196 | 2/1999 |
| WO | 99/53035 | 10/1999 |
| WO | 01/66508 | 9/2001 |
| WO | 02/29020 | 4/2002 |
| WO | 02/36797 | 5/2002 |
| WO | 02/072855 | 9/2002 |
| WO | 03/040290 | 5/2003 |
| WO | 2005/005649 | 1/2005 |
| WO | 2005/010182 | 2/2005 |
| WO | 2005/021770 | 3/2005 |
| WO | 2005/026349 | 3/2005 |
| WO | 2005/030973 | 4/2005 |
| WO | 2005/113744 | 12/2005 |
| WO | 2005/113745 | 12/2005 |
| WO | 2006/020663 | 2/2006 |
| WO | 2006/031424 | 3/2006 |
| WO | 2006/069174 | 6/2006 |
| WO | 2007/046389 | 4/2007 |
| WO | 2007/099867 | 9/2007 |

OTHER PUBLICATIONS

Witkowski et al., Biochemistry 38:11643-11650, 1999.*
Seffernick et al., J. Bacteriol. 183(8):2405-2410, 2001.*
Ba et al., Biomacromolecules 4:1827-1834, 2003.*
Gokarn et al., Biotechnology Letters 20(8):795-798, 1998.*
Hong et al., Applied Microbiology and Biotechnology 58:286-290, 2002.*
Jaurin et al., GenBank accession No. J01611, Feb. 2000.*
Maklashina et al., Journal of Bacteriology 180(22):5989-5996, 1998.*
Bott and Niebisch, *Journal of Biotechnology* 104:129-153 (2004).
Goldberg et al., *Applied and Environmental Microbiology* 45(6): 1838-1847 (1983).
Kurokawa and Sakamoto, *Arch. Microbiol.* 183: 317-324 (2005).
Schnorpfeil et al., *Eur. J. Biochem.* 268: 3069-3074 (2001).
KEGG Database on-line, NCg10359, 2006.
KEGG Database on-line, NCg10360, 2006.
KEGG Database on-line, NCg10361, 2006.
U.S. Appl. No. 11/561,011, Fukui et al., filed Nov. 17, 2006.
U.S. Appl. No. 12/104,595, Koseki et al., filed Apr. 17, 2008.
U.S. Appl. No. 12/090,431, Koseki et al., filed Apr. 16, 2008.
English Language Abstract of JP 3-072891.
English Language Abstract of JP 5-260985.
English Language Abstract of JP 6-014781.
English Language Abstract of JP 7-67683.
English Language Abstract of JP 7-304839.
English Language Abstract of 11-113588.
English Language Abstract of JP 11-130852.
English Language Abstract of JP 11-196888.
English Language Abstract of JP 11-206385.
English Language Abstract of JP 61-209596.
English Language Abstract of JP 62-048394.
English Language Abstract of JP 62-238231.
English Language Abstract of JP 62-238232.
English Language Abstract of JP 2000-037196.
English Language Abstract of JP 2001-161386.
English Language Abstract of JP 2001-190297.
English Language Abstract of JP 2002-191370.
English Language Abstract of JP 2003-171448.
English Language Abstract of JP 2003-199522.
Calvary et al. *Microchemical Journal* 23(4):473-480, 1978.
Chotani et al. *Biochimica et Biophysica Acta* 1543(2):434-455, 2000.
Database UniProt, "Acetyl-CoA Hydrolase", Accession No. Q8NMK4, Oct. 1, 2002.
Database EPO Proteins, "Sequence 32 from International Publication No. WO 03/040290", Accession No. AX771820, Jul. 2, 2003.
Database EMBL, "Sequence 31 from International Publication No. WO 03/040290", Accession No. AX771819, Jul. 2, 2003.
Database Geneseq, "C-Glutamicum Protein Fragment SEQ ID No: 6326", Accession No. AAG92572, Sep. 26, 2001.
Database EMBL, "Sequence 2826 from EP 1 108 790", Accession No. AX122910, May 10, 2001.
Database UniProt, "Butyryl-CoA: Acetate Coenzyme A Transferase", Accession No. Q6M2R3, Jul. 5, 2004.
Gong et al. *Applied Biochemistry and Biotechnology* 57/58:481-487, 1996.
Guettler et al. *International Journal of Systematic Bacteriology* 49:207-216, 1999.
Hong et al. *Biotechnology and Bioengineering* 74(2):89-95, 2001.
Inui et al. *J. of Mol. Microbiol. and Biotechnol.* 7(4):182-196, 2004.
Kalinowski et al. *J. of Biotech.* 104(1-3):5-25, 2003.
Kirchner et al. *J. of Biotech.* 104(1-3):287-299, 2003.
Maxa et al. *Mitteilungen Klosterneuburg* 41(6):233-237, 1991.
Millard et al. *Applied and Environmental Microbiology* 62(5):1808-1810, 1996.
Mori et al. *Shokuhin to Kagaku* 44(4):43-49, 2002.

NP13_601767, NCBI Sequence Viewer, Acetyl-CoA hydrolase, Mar. 20, 2002.
NP13_601811, NCBI Sequence Viewer, Pyruvate Dehyrogenase, Mar. 20, 2002.
Reinscheid et al. *Microbiology* 145:503-513, 1999.
English Language Abstract of JP 1-191686.
English Language Abstract of JP 2-072876.
English Language Abstract of JP 3-210184.
English Language Abstract of JP 57-134500.
English Language Abstract of JP 57-183799.
English Language Abstract of JP 58-035197.
English Language Abstract of JP 58-077895.
English Language Abstract of JP 58-192900.
English Language Abstract of JP 2005-095169.
English Language Abstract of JP 2006-238843.
English Language Abstract of JP 2006-320208.
Arikawa et al. *J. Biosci. Bioeng.* 87(1):28-36, 1999.
Chang et al. *J. Bacteriol.* 151:1279-1289, 1982.
Dunn et al. *J. Bacteriol.* 178:5960-5970, 1996.
Gergely et al. *J. Biol. Chem.* 198:323-334, 1952.
Imabori et al. "Seikagaku Jiten" Dai 3 Pan Tokyo Kagaku Dojin, Oct. 8, 1998, p. 392-393.
Kanarek et al. *J. Biol. Chem.* 239:4202-4206, 1964.
Klotzsch et al., *Meth. Enzymol.* 12:381-386, 1969.
Kondo et al. *Gene* 191:47-50, 1997.
Lehn et al. *Gene* 165:331-332, 1995.
Liebl et al. *International Journal of Systemic Bacteriology* 41:255-260, 1991.
Mackay et al. *Biochem. Biophys. Res. Comm.* 202:1009-1014, 1994.
Peters-Windisch et al. *Microbiology* 144:915-927, 1998.
Ramponi, *Meth. Enzymol.* 42:409-426, 1975.
Schafer et al., *Gene* 145:69-73, 1994.
Shiio et al. *Agric. Biol. Chem.* 44(8):1897-1904, 1980.
Song et al. *Enzyme Microbiol. Technol.* 309:352-361, 2006.
Stucka et al. *Mol. Gen. Genet.* 229:307-315, 1991.
Tomar et al. *Appl. Microbiol. Biotechnol.* 62:76-82, 2003.
Torino et al. *J. Appl. Microbiol.* 91:846-852, 2001.
Uematsu et al. *Plant Cell Reports* 10:286-290, 1991.
Usuda et al. *Microbiology* 142:3347-3354, 1996.
Vertes et al. *Res. Microbiol.* 144:181-185, 1993.
Whisstock et al. *Q. Rev. Biophysics* 36(3):307-340, 2003.
Zhang et al. *Proc. Natl. Acad. Sci.* USA 90:1766-1770, 1993.
U.S. Appl. No. 12/280,426 to Murase et al., filed Dec. 9, 2008.

* cited by examiner

US 7,763,447 B2

METHOD OF PRODUCING SUCCINIC ACID WITH BACTERIUM COMPRISING A MODIFIED FUMARATE REDUCTASE GENE OR A MODIFIED SUCCINATE DEHYDROGENASE GENE

This is a continuation of International Application No. PCT/JP2004/012404, with an international filing date of Aug. 27, 2004.

TECHNICAL FIELD

The present invention relates to the production of succinic acid using bacteria such as coryneform bacteria.

BACKGROUND ART

For the production of non-amino-organic acids including succinic acid by fermentation, anaerobic bacteria including those belonging to the genera *Anaerobiospirillum* or *Actinobacillus* are usually used (U.S. Pat. No. 5,142,834 and U.S. Pat. No. 5,504,004, and International Journal of Systematic Bacteriology (1999), 49, 207-216). Although the yield of products is high by using such anaerobic bacteria, many nutrients are required for their proliferation, and therefore, it is necessary to add a large amount of organic nitrogen sources such as corn steep liquor (CSL) into a culture medium. The addition of large amount of organic nitrogen sources not only leads to an increase in the culture cost but also an increase in purification cost for separating the product, thereby it is not economical.

In addition, a method in which aerobic bacteria such as coryneform bacteria are cultured under aerobic condition to proliferate bacterial cells and then harvested and washed to allow them as resting bacteria to produce non-amino organic acid without oxygen aeration, has been known in the art (JP11-113588A and JP11-196888A). This method is economical because bacteria can grow sufficiently in a simple culture medium containing less amount of organic nitrogen for proliferating bacterial cells. However, there is still a desire for improvement in terms of the production amount of a desired organic acid, the concentration thereof, and the production rate thereof per bacterial cells as well as simplification of the production process, and so on. Furthermore, the production of non-amino organic acid with fermentation using bacteria having an enhanced phosphoenol pyruvate carboxylase activity has been reported (e.g., JP11-196887A). However, there has been no report about the production of non-amino organic acids using bacteria having an enhanced fumarate reductase activity.

DISCLOSURE OF THE INVENTION

An object of the present invention is to provide a method for producing succinic acid with higher productivity.

The inventors of the present invention have intensively studied for solving the aforementioned problems and found that an increase in consumption rate of organic raw materials, production rate of succinic acid, or yield thereof can be attained by allowing a bacterium modified to enhance fumarate reductase activity or cell preparation thereof to react with an organic raw material in a reaction solution containing a carbonate or bicarbonate ion or carbon dioxide gas, and thereby accomplished the present invention.

That is, according to the present invention, the invention described below is provided.

(1) A method for producing succinic acid, comprising allowing a bacterium modified to enhance fumarate reductase activity or cell preparation thereof to react with an organic raw material in a reaction solution containing a carbonate ion, a bicarbonate ion, or carbon dioxide gas to generate succinic acid; and collecting the succinic acid.

(2) The method according to (1), wherein the bacterium is selected from the group consisting of coryneform bacterium, *Bacillus* bacterium, and *Rhizobium* bacterium.

(3) The method according to (1) or (2), wherein the bacterium is a bacterium modified to enhance fumarate reductase by using a succinate dehydrogenase gene from coryneform bacterium.

(4) The method according to (1) or (2), wherein the bacterium is a bacterium modified to enhance fumarate reductase activity by using a fumarate reductase gene from *Escherichia coli*.

(5) The method according to any one of (1) to (4), wherein the bacterium is further modified to decrease lactate dehydrogenase activity to 10% or less as compared to an unmodified strain.

(6) The method according to any one of (1) to (5), wherein the bacterium is further modified to enhance pyruvate carboxylase activity.

(7) The method according to any one of (1) to (6), wherein said bacterium or cell preparation thereof is reacted with the organic raw material under an anaerobic condition.

(8) The method according to any one of (1) to (7), wherein the organic raw material is glucose.

(9) A method for producing a polymer containing succinic acid, comprising producing succinic acid by the method according to any one of (1) to (8), and polymerizing the obtained succinic acid.

DESCRIPTION OF THE PREFERRED EMBODIMENTS

Figure 1:
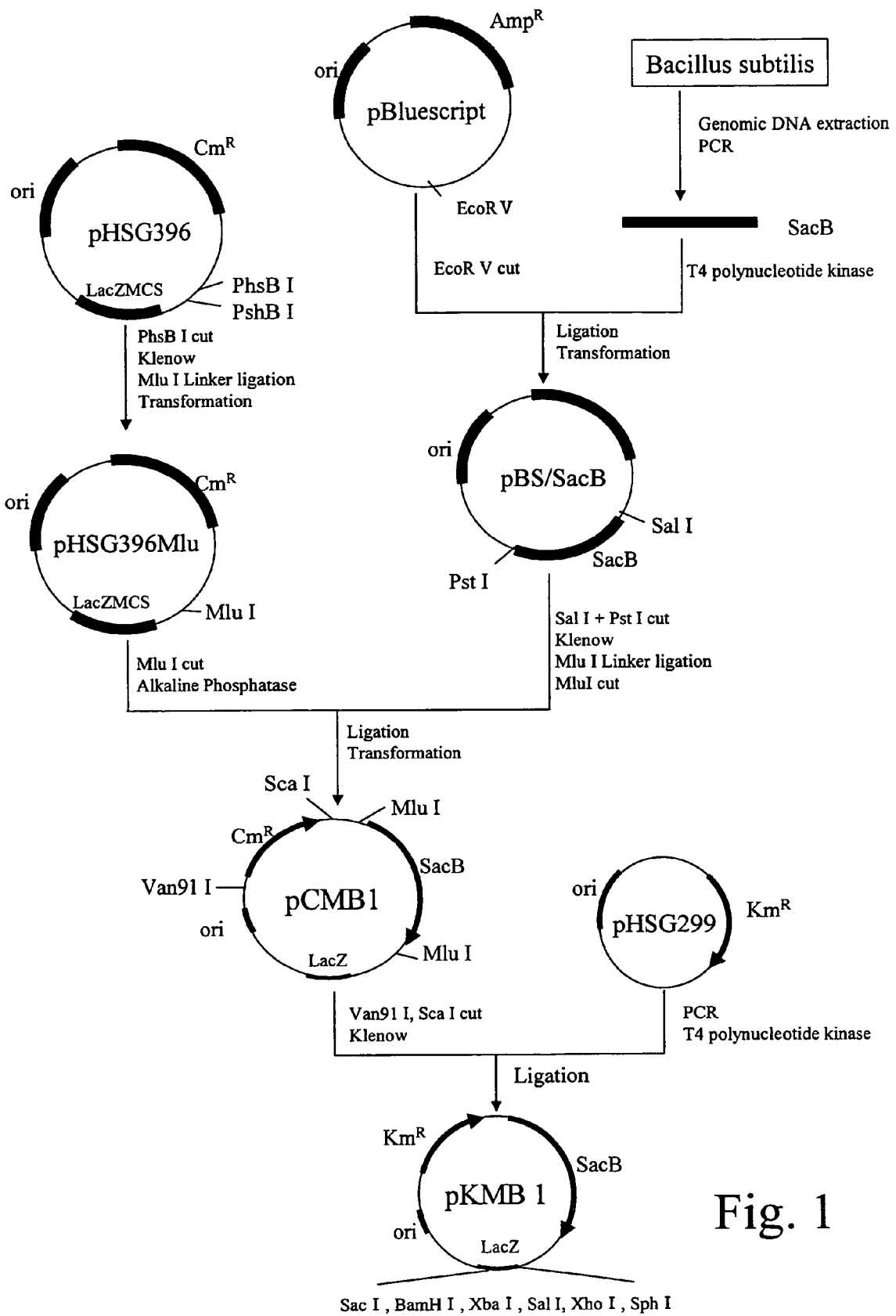
FIG. 1 shows the procedure for constructing the plasmid pKMB1 and a restriction enzyme map thereof.

Hereinafter, embodiments of the present invention will be described in detail.

Bacteria which can be used in the production method of the present invention are those modified so as to enhance fumarate reductase activity. Here, the term "fumarate reductase activity" means an activity to catalyze a reaction in which fumaric acid is converted into succinic acid by reductive reaction, and the term "fumarate reductase activity is enhanced" means an increase in fumarate reductase activity compared to that of a wild-type or fumarate reductase-unmodified strain. The fumarate reductase activity can be determined by a method of measuring a decrease in $K_3Fe(CN)_6$ level as described later. Fumarate reductase of *Escherichia coli* is an enzyme responsible for a reverse reaction of succinate dehydrogenase that works in the clockwise rotation in TCA cycle, and it is involved in fumaric acid respiration under aerobic conditions. It is reported that expression of the gene is repressed at a transcription level under aerobic conditions (Jones, H. M., Gunsalus, R. P., J. Bacteriol., 1985, Vol. 164, p 1100-1109). Therefore, it may be considered that the growth of bacterial cells may be attenuated when the fumarate reductase activity is excessively enhanced. For this reason, in the present invention, it is preferable that the fumarate reductase activity is enhanced insofar as significant growth inhibition of bacterial cells does not occur.

The enhancement of fumarate reductase activity can be performed by modifying a parent strain of the bacterium, for example, by a genetic recombination technique using a fumarate reductase gene. Furthermore, a gene encoding succinate dehydrogenase may be a gene encoding a protein having fumarate reductase activity as well as succinate dehydrogenase activity. Therefore, the expression of the gene encoding the protein having both the fumarate reductase activity and the succinate dehydrogenase activity may be enhanced. For instance, the succinate dehydrogenase of coryneform bacteria is able to catalyze a reaction of producing succinic acid from fumaric acid, which is an inverse reaction of succinate dehydrogenase. The succinate dehydrogenase activity can be determined by a method of Arkell B. A. C et al. (Meth Enzymol, 53, 466-483).

A parent strain of the bacterium that can be used in the present invention is not particularly limited as long as the strain has productivity of succinic acid. Among them, a coryneform bacterium, *Bacillus* bacterium, or *Rhizobium* bacterium is preferable, and a coryneform bacterium is more preferable. Examples of the coryneform bacterium include a microorganism belonging to the genus *Corynebacterium*, a microorganism belonging to the genus *Brevibacterium*, and a microorganism belonging to the genus *Arthrobacter*. Of those, bacteria belonging to the genus *Corynebacterium* or *Brevibacterium* are preferable, and bacteria belonging to *Corynebacterium glutamicum, Brevibacterium flavum, Brevibacterium ammoniagenes*, or *Brevibacterium lactofermentum* are more preferable.

Specific examples of preferable parent strains of the bacterium include *Brevibacterium flavum* MJ-233 (FERM BP-1497), *Brevibacterium flavum* MJ-233 AB-41 (FERM BP-1498), *Brevibacterium ammoniagenes* ATCC6872, *Corynebacterium glutamicum* ATCC31831, and *Brevibacterium lactofermentum* ATCC13869. *Brevibacterium flavum* may be currently classified into *Corynebacterium glutamicum* (Lielbl, W., Ehrmann, M., Ludwig, W. and Schleifer, K. H., International Journal of Systematic Bacteriology, 1991, vol. 41, p 255-260). Therefore, in the present invention, *Brevibacterium flavum* MJ-233 strain and its mutant MJ-233 AB-41 strain are defined as the same strains as *Corynebacterium glutamicum* MJ-233 strain and *Corynebacterium glutamicum* MJ-233 AB-41 strain, respectively.

*Brevibacterium flavum* MJ-233 has been deposited with the accession number FERM P-3068 at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-8566, Japan) on Apr. 28, 1975, and then converted to the international deposit under Budapest Treaty on May 1, 1981 with the accession number FERM BP-1497.

The above-mentioned bacteria used as a parent strain in the method of the present invention may be any strains including variants obtained by conventional treatments for mutagenesis, such as UV irradiation and NTG treatment, and recombinant strains bred by genetic procedures such as cell fusion and genetic recombination techniques, as well as wild-type strains. Furthermore, hosts for the genetic recombinant strains may be those classified in the same genus and species or those classified as different genus and species with respect to a parent strain, so long as it is a transformable microorganism, but preferably the host may be aerobic bacteria as described above.

In the case when the modification is carried out to enhance fumarate reductase activity by fumarate reductase (FRD) gene, the gene which can be used is not specifically limited so long as it encodes a protein having the fumarate reductase activity, and examples thereof include genes of *Escherichia coli* having nucleotide sequence shown in SEQ ID NO: 19. These genes form an operon that comprises genes (nucleotide numbers 440-2239, 2241-2975, 2986-3381, and 3392-3751 of SEQ ID NO: 19) each encoding four subunits (frdA, frdB, frdC, and frdD; SEQ ID NOS: 20-23) that constitute fumarate reductase. The whole operon gene may be introduced into the bacteria, or each of the subunit genes may be introduced separately. Each of the subunit genes may be, as long as it encodes a subunit protein capable of forming a complex having the FRD activity, a DNA that hybridizes with a DNA having the above-mentioned nucleotide sequence under stringent conditions, or a homolog such as a DNA having homology of not less than 90%, preferably not less than 95%, more preferably not less than 99% with respect to the DNA having the above-mentioned nucleotide sequence. Here, the stringent conditions include conditions that allow hybridization at salt concentration corresponding to a washing condition of conventional Southern hybridization, 60° C., 1×SSC, 0.1% SDS, preferably 60° C., 0.1×SSC, 0.1% SDS. By the way, among those FRD gene homologs, a gene that encodes a protein in which an amino acid corresponding to the 17th amino acid in the B subunit of FRD (frdB) (SEQ ID NO: 21) is lysine may be used. A gene having a nucleotide sequence shown in SEQ ID NO: 19 or a homolog thereof can be obtained by PCR method or a hybridization method.

If required, a mutation changing an amino acid corresponding to the 17th amino acid of frdB to lysine can also be introduced by a known method.

Furthermore, a gene that encodes a protein having both the activities of succinic dehydrogenase and fumarate reductase may be used. An example thereof includes the sdh genes of coryneform bacteria, which has a nucleotide sequence shown in SEQ ID NO: 28. These genes form an operon that comprises genes (nucleotide numbers 1153-3171, 3174-3920, and 363-1133 of SEQ ID NO: 28) each encoding three subunits (sdhA, sdhB, and sdhC) that constitute succinate dehydrogenase. The sdh operon of *Corynebacterium glutamicum* is shown in GeneBank Accession NOS. NCg10359 (sdhC), NCg10360 (sdhA), and NCg10361 (sdhB).

The whole operon gene may be introduced into the bacteria, or each of the subunit genes may be introduced. Each of the subunit genes may be, so long as it encodes a subunit protein capable of forming a complex having the FRD activity, a DNA that hybridizes with a DNA having the above-mentioned nucleotide sequence under stringent conditions, or a homolog such as a DNA having homology of not less than 90%, preferably not less than 95%, more preferably not less than 99% with respect to the DNA having the above-mentioned nucleotide sequence. Here, the stringent condition includes a conditions that allow hybridization at salt concentration corresponding to a washing condition of conventional Southern hybridization, 60° C., 1×SSC, 0.1% SDS, preferably 60° C., 0.1×SSC, 0.1% SDS.

In addition, it may be a gene that encodes a protein having an amino acid sequence of any of those shown in SEQ ID NOS: 20-23 and 29-31 including substitution, deletion, insertion, or addition of one or several amino acids, as long as the protein has the fumarate reductase activity. Here, for example, the term "several" means 2 to 20, preferably 2 to 10, more preferably 2 to 5.

The FRD gene obtained from any bacteria other than *Escherichia coli* or coryneform bacteria, or from any other microorganisms, animals, and plants can also be used. For instance, the FRD gene obtained from any microorganisms, animals, or plants may be a gene whose nucleotide sequence is already known, or a gene whose nucleotide sequence is determined after isolating a gene that encodes a protein having the FRD activity from chromosome of a bacterium, animal, or plant, based on a homology. In addition, after the determination of the nucleotide sequence, a gene synthesized in accordance with the sequence can also be used. These genes can be obtained by amplifying a region comprising promoter and ORF by the hybridization or PCR.

When a coryneform bacterium is used, for example, a recombinant plasmid capable of enhancing the expression of FRD gene in the coryneform bacterium can be obtained by inserting a DNA fragment containing the FRD gene into a suitable plasmid such as a plasmid vector containing at least a gene responsible for replication of plasmid in coryneform bacteria. The plasmid vector capable of introducing the FRD gene into a coryneform bacterium is not particularly limited so long as it contains at least a gene responsible for replication and amplification in coryneform bacteria. Specific examples thereof include: plasmid pCRY30 described in JP03-210184A; plasmids pCRY21, pCRY2KE, pCRY2KX, pCRY31, pCRY3KE, and pCRY3KX described in JP02-72876A and U.S. Pat. No. 5,185,262; plasmids pCRY2 and pCRY3 described in JP01-191686A; pAM330 described in JP58-67679A; pHM1519 described in JP58-77895A; pAJ655, pAJ611, and pAJ1844 described in JP58-192900A; pCG1 described in JP57-134500A; pCG2 described in JP58-35197A; pCG4 and pCG11 described in JP57-183799A; and pVK7 described in JP10-215883A.

As described above, an excess increase of fumarate reductase activity may attenuate the growth of bacterial cells. Therefore, it is preferable to adjust the expression level of the FRD gene to the extent that the growth of bacterial cells is not inhibited, by selecting an appropriate number of plasmid copies. Furthermore, the enhancement of FRD activity can be carried out by introducing, substituting, or amplifying the FRD gene on a chromosome by conventional homologous recombination.

In addition to the methods as described above, when the FRD gene has an operon structure, the enhancement can also be attained by introducing a mutation in a promoter region that regulates its expression, as described in WO00/18935.

In the incorporation of the above-described into a recombinant plasmid or a chromosome, a promoter for FRD gene expression may be any promoter so long as it functions in coryneform bacteria. Alternatively, it may be the promoter of the FRD gene itself. The promoter may be suitably selected to adjust the expression level of the FRD gene.

So far, the examples of using the coryneform bacteria are described. However, the same process can be applied in the use of other bacteria to attain the enhancement of FRD activity.

By the way, in the reaction of the present invention, it is more effective to use a bacterial strain modified to decrease lactate dehydrogenase activity in addition to the enhancement of fumarate reductase activity. Here, the term "the lactate dehydrogenase activity is decreased" means a decrease in lactate dehydrogenase activity as compared to a strain in which lactate dehydrogenase is unmodified. The lactate dehydrogenase activity per bacterial cells is preferably decreased to 10% or less as compared to a strain with unmodified lactate dehydrogenase. In addition, the lactate dehydrogenase activity may be completely eliminated. The decrease in lactate dehydrogenase activity can be confirmed by determining the lactate dehydrogenase activity by a known method (L. Kanarek and R. L. Hill, J. Biol. Chem. 239, 4202 (1964)). As a specific method for preparing a mutant strain of coryneform bacterium in which lactate dehydrogenase activity is decreased, a method using homologous recombination on a chromosome as described in JP11-206385A or a method using the SacB gene described in the Examples of the present specification (Schafer, A. et al., Gene 145 (1994) 69-73) can be used. The coryneform bacterium of the present invention having an enhanced FRD gene expression and decreased lactate dehydrogenase activity can be obtained, for example, by preparing a bacterium having disrupted LDH gene and transforming the bacterium with a recombinant vector containing the FRD gene, as described in Example 2 shown below. However, either of the modification for decreasing the LDH activity and the modification for enhancing the FRD activity may be performed first.

In addition, a bacterium modified so that pyruvate carboxylase activity is enhanced in addition to the enhancement of fumarate reductase activity may be used in the reaction of the present invention. The term "the pyruvate carboxylase activity is enhanced" means an increase in pyruvate carboxylase activity as compared to that of an unmodified strain such as a wild-type strain or a parent strain. The pyruvate carboxylase activity can be, for example, determined by a method of measuring a decrease of NADH as described later. The coryneform bacterium with enhanced expressions of fumarate reductase and pyruvate carboxylase can be prepared by expressing the fumarate reductase (FRD) gene and the pyruvate carboxylase (PC) gene at high level in coryneform bacterium in a similar way as described in JP11-196888A.

The PC gene used in the method of the present invention may be a gene whose nucleotide sequence is already known. Alternatively, a gene obtained by isolating a DNA fragment encoding a protein having the PC activity from a chromosome of a microorganism, animal, plant, or the like by such a method as described below, and determining its nucleotide sequence can be used. Furthermore, after the determination of the nucleotide sequence, a gene synthesized based on the sequence can also be used.

DNA fragments containing PC genes reside on a chromosome from microorganisms, animals, and plants. Basic procedures for preparing PC genes from those donor microorganisms, animals, and plats will be exemplified by referring to a gene derived from coryneform bacteria whose sequence is known.

The PC gene resides on the chromosomes of *Corynebacterium glutamicum* strain ATCC 13032, one of coryneform bacteria, (Peters-Wendisch, P. G. et al., Microbiology, vol. 144 (1998) p 915-927), and its nucleotide sequence is known in the art (GenBank Database Accession No. AP005276) (SEQ ID NO: 15), so that the gene can be isolated and obtained by PCR.

For instance, the PC gene of about 3.7 kb can be amplified by carrying out PCR using oligonucleotides having nucleotide sequences shown in SEQ ID NOS: 13 and 14 as primers and using chromosome of *Corynebacterium glutamicum* as a template. In this case, an appropriate restriction enzyme recognition site may be added to the 5'-terminal of the primers used in PCR to allow the gene to be inserted into a suitable region of such a vector as described below, and the obtained recombinant vector can be used for gene transfer into coryneform bacterium.

In addition, even if a nucleotide sequence is unidentified, a protein can be purified based on PC activity and a probe is then synthesized based on the N-terminal amino acid sequence of the protein or a sequence of partially-digested fragments to isolate a gene fragment by a routine hybridization procedure. Alternatively, a probe or primer may be synthesized on the basis of an amino acid sequence in a region conserved in PC proteins to obtain a fragment by hybridization or PCR. The nucleotide sequence of the obtained fragment can be determined by a conventional procedure.

In the present specification, the size of the digested DNA fragments and plasmids can be calculated; when agarose gel electrophoresis is employed, on the basis of a reference line drawn by migration distances of DNA fragments having known molecular weights obtained by digestion of *Escherichia coli* λ phage with the restriction enzyme HindIII on the same agarose gel; or when polyacrylamide gel electrophoresis is employed, on the basis of a reference line drawn by migration distances of DNA fragments having known molecular weights obtained by digestion of *Escherichia coli* φX174 phage with the restriction enzyme HaeIII on the same polyacrylamide gel. On the determination of the size of each DNA fragment, 1% agarose gel electrophoresis were employed for the fragments of 1 kb or more in size, and 4% polyacrylamide gel electrophoresis were employed for the fragments of about 0.1 kb or more but less than 1 kb in size.

In the present invention, the DNA fragment including the above PC gene used for enhancing the PC activity is not only one isolated from the chromosomal DNA of *Corynebacterium glutamicum*, but one synthesized using a conventional DNA/RNA synthesizing apparatus, for example, a 394 DNA/RNA synthesizer manufactured by Applied Biosystems Inc. Furthermore, as a PC gene obtained from the chromosomal DNA of coryneform bacteria as described above, some nucleotides in the nucleotide sequence of SEQ ID NO: 15 may be substituted with other nucleotides, deleted, or inserted with additional nucleotides, so long as there is no substantial defect in the function of PC encoded by the gene, i.e., the property of carbon dioxide fixation. Furthermore, some nucleotide sequence may be inverted. Any of those derivatives can be used in the present invention. A DNA that hybridizes with a DNA having a nucleotide sequence of SEQ ID NO: 15 under stringent conditions, or a DNA having homology of not less than 90%, preferably not less than 95%, more preferably not less than 99% to the nucleotide sequence of SEQ ID NO: 15, and encodes a protein having PC activity, can be preferably used. Here, the stringent condition includes any condition that allows hybridization at salt concentrations corresponding to a washing condition of conventional Southern hybridization, 60° C., 1×SSC, 0.1% SDS, preferably, 60° C., 0.1×SSC, 0.1% SDS.

The PC gene obtained from any bacteria other than *Corynebacterium glutamicum*, or from any microorganisms, animals, and plants can also be used. In particular, the nucleotide sequence of the PC genes from the microorganisms, animals, and plants, such as those described below, are known (references are indicated below). Therefore, PC gene can be obtained in the same way as described above with hybridization or the amplification of ORF by PCR.

*Homo sapiens* [Biochem. Biophys. Res. Comm., 202, 1009-1014, (1994)]
*Mus musculus* [Proc. Natl. Acad. Sci. USA., 90, 1766-1779, (1993)]
rat [GENE, 165, 331-332, (1995)]
yeast; *Saccharomyces cerevisiae* [Mol. Gen. Genet., 229, 307-315, (1991)] *Schizosaccharomyces pombe* [DDBJ Accession No.; D78170]
*Bacillus stearothermophilus* [GENE, 191, 47-50, (1997)]
*Rhizobium etli* [J. Bacteriol., 178, 5960-5970, (1996)]

The DNA fragment containing the PC gene can be expressed by inserting the DNA fragment into a suitable expression plasmid such as pUC118 (manufactured by Takara Shuzo Co., Ltd.), followed by introduction into a suitable host microorganism such as *Escherichia coli* JM109 (manufactured by Takara Shuzo Co., Ltd.). The expressed PC gene product, pyruvate carboxylase (SEQ ID NO: 16), can be confirmed by directly determining the PC activity by the method of Magasanik [J. Bacteriol., 158, 55-62, (1984)] using a crude enzyme solution prepared from the transformant, and then comparing the PC activity with that of a crude enzyme solution prepared from a non-transformant. The DNA fragment containing the PC gene is inserted into a suitable plasmid, such as a plasmid vector containing at least a gene responsible for replication of the plasmid in coryneform bacteria, and thereby, a recombinant plasmid capable of high expression of PC in coryneform bacteria can be obtained. In the recombinant plasmid, a promoter for expressing PC gene may be one derived from coryneform bacteria. However, it is not limited to such promoters, and any promoter can be used so long as it is a nucleotide sequence capable of initiating the transcription of PC gene. For instance, TZ4 promoter as described in Example 3 may be used.

A Plasmid vector, into which the PC gene can be introduced, is not specifically limited so long as it contains a gene responsible for replication in coryneform bacterium. The specific examples include: plasmid pCRY30 described in JP03-210184A; plasmids pCRY21, pCRY2KE, pCRY2KX, pCRY31, pCRY3KE, and pCRY3KX described in JP02-72876A and U.S. Pat. No. 5,185,262; plasmids pCRY2 and pCRY3 described in JP01-191686A; pAM330 described in JP58-67679A; pHM1519 described in JP58-77895A; pAJ655, pAJ611, and pAJ1844 described in JP58-192900A; pCG1 described in JP57-134500A; pCG2 described in JP58-35197A; and pCG4 and pCG11 described in JP57-183799A.

Of those, plasmids comprising a gene responsible for replication and a gene responsible for the stabilization of the plasmid in coryneform bacteria are preferably used as plasmid vectors for the host-vector system in coryneform bacterium. For instance, plasmids pCRY30, pCRY21, pCRY2KE, pCRY2KX, pCRY31, pCRY3KE, and pCRY3KX can be preferably used.

Coryneform bacterium having enhanced PC gene expression can be obtained by transforming the coryneform bacteria, for example, *Brevibacterium flavum* strain MJ-233 (FERM BP-1497), with a recombinant vector prepared by inserting the PC gene into an appropriate site of a plasmid vector which can be replicable in aerobic coryneform bacteria as described above. In addition, the enhancement of PC activity can also be performed by expressing PC gene on chromosome by introducing, substituting, or amplifying the gene, according to conventional homologous recombination. The resulting bacterium is transformed with a recombinant vector containing the FRD gene to obtain coryneform bacteria having enhanced expressions of the PC and FRD genes. Either of FRD and PC genes may be introduced first. The transformation may be carried out by, for example, the electric pulse method (Res. Microbiol., Vol. 144, p. 181-185, 1993).

Furthermore, in the present invention, the bacterium modified so that activities of fumarate reductase and pyruvate carboxylase are enhanced and lactate dehydrogenase activity is decreased is particularly preferably used in the production of succinic acid. Such bacterium can be obtained by transforming a coryneform bacterium having disrupted LDH gene with recombinant vectors containing PC genes and FRD genes, respectively. Any of the modification procedures using those genes may be performed first.

When the above-described bacterium is used in the reaction for producing succinic acid, cells subjected to slant culture on a solid medium such as an agar medium may be used, and preferably the above-described bacterium may be pre-incubated in a liquid medium (seed culture) before use. It is possible to produce succinic acid by allowing the seed-cultured bacterium to react with the organic materials while growing it in a culture medium containing organic raw materials. In addition, succinic acid can be produced by allowing the proliferated bacterial cells to react with organic raw materials in a reaction solution containing the organic raw materials. When aerobic coryneform bacterium is used for the method of the present invention, it is preferable to use the bacterium after culturing the bacterial cells under normal aerobic condition. The culture medium used for culture may be any of those normally used for culture of microorganisms. For instance, a conventional culture medium, which is prepared by adding a natural nutrient source such as meat extract, yeast extract, or peptone to a composition made up of inorganic salt such as ammonium sulfate, potassium phosphate, and magnesium sulfate, can be used. The bacterial cells after culture can be collected by centrifugation, membrane separation, or the like, and then used for reaction.

In the present invention, cell preparation of bacteria can also be used. For instance, the cell preparation of the bacteria include immobilized bacterial cells immobilized in acrylamide, carrageenan, or the like, lysed bacterial cells, centrifugal supernatant thereof, or fraction obtained by partially purifying the supernatant with an ammonium sulfate treatment or the like.

An organic raw material to be used in the production method of the present invention is not limited as long as it is a carbon source which the microorganism can assimilate to produce succinic acid. Generally, fermentable carbohydrates such as galactose, lactose, glucose, fructose, glycerol, sucrose, saccharose, starch, and cellulose; or polyalcohol such as glycerin, mannitol, xylitol, and ribitol are used as carbon sources. Of those, glucose, fructose, and glycerol are preferable, and glucose is particularly preferable.

In addition, a saccharified starch solution, molasses, or the like, which contains the above-described fermentable carbon hydrates, can also be used. Those fermentable carbohydrates may be used solely or in combination. The concentration of the above-described organic raw material is not particularly limited, but it is advantageous to increase the amount so long as it is within the range under which the production of succinic acid is not inhibited. The concentration of the organic raw material is generally in the range of 5 to 30% (w/v), preferably 10 to 20% (w/v). Furthermore, the organic raw materials can also be supplemented when the above-described organic raw material is decreased as the reaction progresses.

The reaction solution containing the organic raw materials is not particularly limited and, for instance, may be any culture media for bacterial culture or any buffers including a phosphate buffer. The reaction solution is preferably an aqueous solution containing a nitrogen source, inorganic salts, and so on. Here, the nitrogen source is not particularly limited so long as it can be assimilated by the microorganism for the production of succinic acid. Specifically, the nitrogen source includes various organic and inorganic nitrogen compounds such as ammonium salt, nitrate, urea, soybean hydrolysate, casein hydrolysate, peptone, yeast extract, meat extract, and corn steep liquor. The inorganic salt includes various kinds of phosphate salt, sulfate salt, and metal salts such as magnesium salt, potassium salt, manganese salt, iron salt, zinc salt, and the like. In addition, any components that promote the growth of bacterial cells, including vitamins such as biotin, pantothenic acid, inositol and nicotinic acid, nucleotides and amino acids, may be added if necessary. Furthermore, it is preferable that an optimum amount of a commercially available anti-foaming agent is added to the culture medium to suppress foaming at the time of reaction.

The pH of the reaction solution can be adjusted by adding sodium carbonate, sodium bicarbonate, potassium carbonate, potassium bicarbonate, magnesium carbonate, sodium hydroxide, calcium hydroxide, magnesium hydroxide, or the like. The pH for the reaction is usually pH of 5 to 10, preferably pH of 6 to 9.5, and therefore, pH of the reaction solution can be adjusted within the above range with an alkaline material, carbonate, urea, or the like during the reaction if required.

The reaction solution used in the present invention may be water, a buffer, a culture medium, or the like, but the culture medium is preferable. For example, a carbonate or bicarbonate ion, or carbon dioxide gas as well as the above-described organic raw materials is added to the culture medium, and then reaction can be performed under anaerobic condition. The carbonate or bicarbonate ion may be supplied from magnesium carbonate, sodium carbonate, sodium bicarbonate, potassium carbonate, or potassium bicarbonate, which can also be used as a neutralizing agent. However, if required, the carbonate or bicarbonate ion may be supplied from carbonic acid or bicarbonic acid or salts thereof or carbon dioxide gas. The specific examples of the salts of carbonate or bicarbonate include magnesium carbonate, ammonium carbonate, sodium carbonate, potassium carbonate, ammonium bicarbonate, sodium bicarbonate, and potassium bicarbonate. In addition, the carbonate ion or bicarbonate ion is added at a concentration of 0.001 to 5 M, preferably 0.1 to 3 M, more preferably 1 to 2 M. When the carbon dioxide gas is added, the amount of carbon dioxide gas is 50 mg/l to 25 g/l, preferably 100 mg/l to 15 g/l, more preferably 150 mg/l to 10 g/l in the solution.

The optimal temperature for growth of the bacterium used in the reaction is generally in the range of 25 to 35° C. The temperature of the reaction is generally in the range of 25 to 40° C., preferably in the range of 30 to 37° C. The amount of bacterial cells used in the reaction is, but not limited to, 1 to 700 g/L, preferably 10 to 500 g/L, more preferably 20 to 400 g/L. The reaction time is preferably 1 to 168 hours, more preferably 3 to 72 hours.

For culturing the bacterium, it is necessary to supply oxygen by aeration and agitation. On the other hand, succinic acid may be produced with aeration and agitation, or may be produced under anaerobic atmosphere without aeration and oxygen supply. The term "anaerobic condition" used herein means that a reaction is conducted while keeping the dissolved oxygen level low in the solution. In this case, it is preferable to carry out a reaction at a dissolved oxygen level of 0 to 2 ppm, preferably 0 to 1 ppm, more preferably 0 to 0.5 ppm. For that purpose, the reaction may be performed in a hermetically sealed vessel without aeration; the reaction may be performed while inert gas such as nitrogen gas is supplied; or the reaction may be performed while inert gas containing carbon dioxide gas is supplied.

Succinic acid accumulated in the reaction solution (culture medium) can be collected and purified from the reaction solution according to conventional procedures. Specifically, succinic acid can be collected and purified from the solution, by removing solid components such as bacterial cells or the like by centrifugation, filtration, or the like, and desalting it with an ion exchange resin or the like, followed by crystallization or column chromatography.

In the present invention, after production of succinic acid by the method of the present invention as described above, a polymerization reaction may be carried out using the obtained succinic acid as a raw material to produce a polymer containing succinic acid. In recent years, the number of environmentally-friendly industrial products increases, and polymers prepared from raw materials of a plant origin are attracting attention. The succinic acid produced in the present invention can be processed into polymers such as polyester and polyamide. In addition, the succinic acid obtained by the production method of the present invention or a composition containing said succinic acid can be used for food additives, pharmaceutical agents, cosmetics, and the like.

EXAMPLES

Hereinafter, the present invention will be described in further detail with reference to Examples. However, the present invention is not limited to these examples.

Example 1

Construction of a Gene Disruption Vector (A) Extraction of *Bacillus subtilis* Genomic DNA

*Bacillus subtilis* ISW1214 was cultured until a late logarithmic growth phase in a 10 mL LB medium [composition: 10 g of tryptone, 5 g of yeast extract, and 5 g of NaCl dissolved in 1 L of distilled water], and the bacterial cells were collected. The obtained bacterial cells were suspended in 0.15 mL of 10 mM NaCl/20 mM Tris buffer (pH of 8.0)/1 mM EDTA.2Na containing 10 mg/mL of lysozyme.

Then, proteinase K was added to the suspension at a final concentration of 100 µg/mL, and maintained at 37° C. for 1 hour. Then, sodium dodecyl sulfate solution was added thereto at a final concentration of 0.5%, and maintained at 50° C. for 6 hours for lysis. To this lysate, an equal amount of a phenol/chloroform solution was added, and shaken slowly at room temperature for 10 minutes. Then, the total suspension was subjected to centrifugation (5,000×g, 20 minutes, 10 to 12° C.), and a supernatant fraction was taken. Sodium acetate solution was added to the supernatant fraction at a concentration of 0.3 M, and then twice amount of ethanol was added and mixed. A precipitate was recovered by centrifugation (15,000×g, 2 minutes), then washed with 70% ethanol and air dried. 5 mL of 10 mM Tris buffer (pH of 7.5)/1 mM EDTA-2Na was added to the obtained DNA. The resultant solution was left standing overnight at 4° C., and used as a template DNA for PCR.

(B) Amplification and Cloning of SacB Gene by PCR

A *Bacillus subtilis* SacB gene was obtained by performing PCR by using the DNA prepared in the above section (A) as a template; and using synthetic DNAs (SEQ ID NOS: 1 and 2) designed based on the reported nucleotide sequence of the gene (GenBank Database Accession No. X02730).

The composition of the reaction solution is as follows. 1 µL of the template DNA, 0.2 µL of PfxDNA polymerase (available from Invitrogen), 1-fold concentration of the supplied buffer, 0.3 µM of respective primers, 1 mM $MgSO_4$, and 0.25 µM dNTPs were mixed, and total volume of the reaction solution was adjusted to 20 µL.

Reaction temperature condition is as follows: The DNA Thermal Cycler PTC-2000 manufactured by MJ Research Co., Ltd. was used and a cycle of 94° C. for 20 seconds and 68° C. for 2 minutes was repeated 35 times. For the first cycle, heat-retention at 94° C. was conducted for 1 minute 20 seconds. For the last cycle, the heat-retention at 68° C. was conducted for 5 minutes.

An amplified product was analyzed by separating it in 0.75% agarose (SeaKem GTG agarose, available from FMC BioProducts) gel electrophoresis and visualizing with ethidium bromide staining, to thereby detect a fragment of about 2 kb. The target DNA fragment was recovered from the gel by using QIAQuick Gel Extraction Kit (available from QIAGEN).

A 5'-end of the recovered DNA fragment was phosphorylated with T4 Polynucleotide Kinase (available from Takara Shuzo Co., Ltd.) and was inserted into an EcoRV site of the *Escherichia coli* vector (pBluescript II: available from STRATEGENE) by using Ligation Kit ver. 2 (available from Takara Shuzo Co., Ltd.), and the obtained plasmid DNA was used to transform *Escherichia coli* (DH5α strain). The obtained recombinant *Escherichia coli* was spread over an LB agar medium (10 g of tryptone, 5 g of yeast extract, 5 g of NaCl, and 15 g of agar dissolved in 1 L of distilled water) containing 50 µg/mL ampicillin and 50 µg/mL X-Gal.

Clones each forming a white colony on this medium were transferred to an LB agar medium containing 50 µg/mL ampicillin and 10% sucrose, and was cultured at 37° C. for 24 hours. Of those clones, clones which could not grow on the medium containing sucrose were subjected to liquid culture by a conventional method, and then the plasmid DNA was isolated. An *Escherichia coli* strain in which SacB gene is functionally expressed must be incapable of growing in the medium containing sucrose. The obtained plasmid DNA was digested with restriction enzymes SalI and PstI. The plasmid DNA was confirmed to have an insert of about 2 kb and the plasmid was named pBS/SacB.

(C) Construction of Chloramphenicol-Resistant SacB Vector 500 ng of *Escherichia coli* plasmid vector pHSG396 (chloramphenicol resistant marker, available from Takara Shuzo Co., Ltd.) was reacted with 10 units of restriction enzyme PshBI at 37° C. for 1 hour, and recovered by phenol/chloroform extraction and ethanol precipitation. Both ends of the resultant DNA were each made blunt with Klenow Fragment (available from Takara Shuzo Co., Ltd.), and MluI linker (available from Takara Shuzo Co., Ltd.) was ligated thereto by using the Ligation Kit ver. 2 (available from Takara Shuzo Co., Ltd.) to form a circular plasmid, and the obtained plasmid was used to transform the *Escherichia coli* (DH5α strain). The obtained recombinant *Escherichia coli* was spread on an LB agar medium containing 34 µg/mL chloramphenicol. A plasmid DNA was isolated from the obtained clones by a conventional method. A clone having a cleavage site of a restriction enzyme MluI was selected and named pHSG396Mlu.

Meanwhile, pBS/SacB constructed in the above section (B) was digested with the restriction enzymes SalI and PstI, and both ends of the obtained DNA were each made blunt with the Klenow Fragment. The MluI linker was ligated thereto by using the Ligation Kit ver. 2 (available from Takara Shuzo Co., Ltd.). Then, a DNA fragment of about 2.0 kb containing SacB gene was separated in 0.75% agarose gel electrophoresis, and recovered. This SacB gene fragment was ligated to the fragment obtained by digesting pHSG396Mlu with the restriction enzyme MluI and dephosphorylated with Alkaline Phosphatase Calf intestine (available from Takara Shuzo Co., Ltd.), by using the Ligation Kit ver. 2 (available from Takara Shuzo Co., Ltd.), and the obtained DNA was used to transform the *Escherichia coli* (DH5α strain). The obtained recombinant *Escherichia coli* was spread on an LB agar medium containing 34 µg/mL chloramphenicol.

The obtained colonies were transferred to an LB agar medium containing 34 µg/mL chloramphenicol and 10% sucrose, and cultured at 37° C. for 24 hours. Among these clones, plasmid DNA was isolated from the clones which could not grow on the medium containing sucrose by a conventional method. The obtained plasmid DNA was subjected to MluI digestion and analyzed. As a result, the plasmid DNA was confirmed to have an insert of about 2.0 kb and named pCMB1.

(D) Acquisition of Kanamycin-Resistant Gene

A kanamycin-resistant gene was obtained by performing PCR using a DNA of *Escherichia coli* plasmid vector pHSG299 (kanamycin resistant marker, Takara Shuzo Co., Ltd.) as a template; and using synthetic DNAs (shown in SEQ ID NOS: 3 and 4) as primers. The composition of the reaction solution is as follows: 1 ng of the template DNA, 0.1 µL of Pyrobest DNA polymerase (available from Takara Shuzo Co., Ltd.), 1-fold concentration of the supplied buffer, 0.5 µM of respective primers, and 0.25 µM dNTPs were mixed, and a total volume of the reaction solution was adjusted to 20 µL.

Reaction temperature condition is as follows: The DNA Thermal Cycler PTC-2000 manufactured by MJ Research Co., Ltd. was used and a cycle of 94° C. for 20 seconds, 62° C. for 15 seconds, and 72° C. for 1 minute 20 seconds was repeated 20 times. For the first cycle, heat-retention at 94° C. was conducted for 1 minute 20 seconds. For the last cycle, the heat-retention at 72° C. was conducted for 5 minutes.

An amplified product was analyzed by separating in 0.75% agarose (SeaKem GTG agarose, available from FMC BioProducts) gel electrophoresis and visualizing with ethidium bromide staining, to thereby detect a fragment of about 1.1 kb. The target DNA fragment was recovered from the gel by using the QIAQuick Gel Extraction Kit (available from QIAGEN). A 5'-end of the recovered DNA fragment was phosphorylated with T4 Polynucleotide Kinase (available from Takara Shuzo Co., Ltd.).

(E) Construction of Kanamycin-Resistant SacB Vector

A DNA fragment of about 3.5 kb obtained by digesting pCMB1 constructed in the above section (C) with restriction enzymes Van91I and ScaI was separated in 0.75% agarose gel electrophoresis, and recovered. The resultant DNA was mixed with the kanamycin resistant gene prepared in the above section (D) and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 µg/mL kanamycin.

A strain grown on the medium containing kanamycin was confirmed to be incapable of growing on the medium containing sucrose. Furthermore, the plasmid DNA prepared from the same strain showed the fragments of 354, 473, 1,807, and 1,997 bp by restriction enzyme HindIII digestion. Thus, it was concluded that the plasmid has the structure shown in FIG. 1, and the plasmid was named pKMB1.

Example 2

Construction of LDH Gene-Disrupted Strain (A) Extraction of a Genomic DNA from *Brevibacterium flavum* MJ233-ES Strain The *Brevibacterium flavum* MJ-233 strain was cultured until the late stage of logarithmic growth phase in a 10 mL A medium (2 g of urea, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 6 mg of $MnSO_4.4-5H_2O$, 200 µg of biotin, 100 µg of thiamine, 1 g of yeast extract, 1 g of casamino aid, and 20 g of glucose dissolved in 1 L of distilled water). The obtained bacterial cells were used to prepare a genomic DNA by the method described in the above section (A) of Example 1.

(B) Cloning of a Lactate Dehydrogenase Gene

A lactate dehydrogenase gene of MJ233 strain was obtained by performing PCR by using the DNA prepared in the above section (A) as a template; and using synthetic DNAs (SEQ ID NOS: 5 and 6) designed based on the nucleotide sequence of the gene described in JP11-206385A. The composition of the reaction solution is as follows: 1 µL of the template DNA, 0.2 µL of TaqDNA polymerase (available from Takara Shuzo Co., Ltd.), 1 time concentration of a supplied buffer, 0.2 µM of respective primers, and 0.25 µM dNTPs were mixed, and a total volume of the reaction liquid was adjusted to 20 µL.

Reaction temperature condition is as follows: The DNA Thermal Cycler PTC-2000 manufactured by MJ Research Co., Ltd. was used and a cycle of 94° C. for 20 seconds, 55° C. for 20 seconds, and 72° C. for 1 minute was repeated 30 times. For the first cycle, heat-retention at 94° C. was conducted for 1 minute 20 seconds. For the last cycle, the heat-retention at 72° C. was conducted for 5 minutes.

The amplified product was analyzed by separating in 0.75% agarose (SeaKem GTG agarose, available from FMC BioProducts) gel electrophoresis and visualizing with ethidium bromide staining, to thereby detect a fragment of about 0.95 kb. The target DNA fragment was recovered from the gel by using QIAQuick Gel Extraction Kit (available from QIAGEN).

The recovered DNA fragment was mixed with the PCR product-cloning vector pGEM-T Easy (available from Promega Corporation) and ligated thereto using Ligation Kit ver. 2 (available from Takara Shuzo Co., Ltd.), and the obtained plasmid DNA was used to transform *Escherichia coli* (DH5α strain). The obtained recombinant *Escherichia coli* was spread on an LB agar medium containing 50 µg/mL ampicillin and 50 µg/mL X-Gal.

Clones each forming a white colony on this medium were subjected to liquid culture by a conventional method, and then the plasmid DNA was purified. The obtained plasmid DNA was cleaved with restriction enzymes SacI and SphI. The plasmid DNA was confirmed to have an insert of about 1.0 kb and named pGEMT/CgLDH.

(C) Construction of a Plasmid for Disrupting Lactate Dehydrogenase Gene pGEMT/CgLDH prepared in the above section (B) was digested with restriction enzymes EcoRV and XbaI to remove a coding region of lactate dehydrogenase of about 0.25 kb. The each end of the remaining DNA fragment of about 3.7 kb was made blunt by the Klenow Fragment and self-ligated by using the Ligation Kit ver. 2 (available from Takara Shuzo Co., Ltd.), and the obtained plasmid was used to transform the *Escherichia coli* (DH5α strain). The obtained recombinant *Escherichia coli* was spread on an LB agar medium containing 50 μg/mL ampicillin.

A strain grown on this medium was subjected to liquid culture by a conventional method, and then the plasmid DNA was isolated. The obtained plasmid DNA was digested with restriction enzymes SacI and SphI. A clone having an insert of about 0.75 kb was selected and named pGEMT/ΔLDH.

Next, the DNA fragment of about 0.75 kb obtained by digesting pGEMT/ΔLDH with the restriction enzymes SacI and SphI was separated in 0.75% agarose gel electrophoresis and recovered, to prepare a lactate dehydrogenase gene fragment in which a part of its region is deleted. This DNA fragment was mixed with the pKMB1 constructed in Example 1 digested with the restriction enzymes SacI and SphI, and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin and 50 μg/mL X-Gal.

Figure 2:
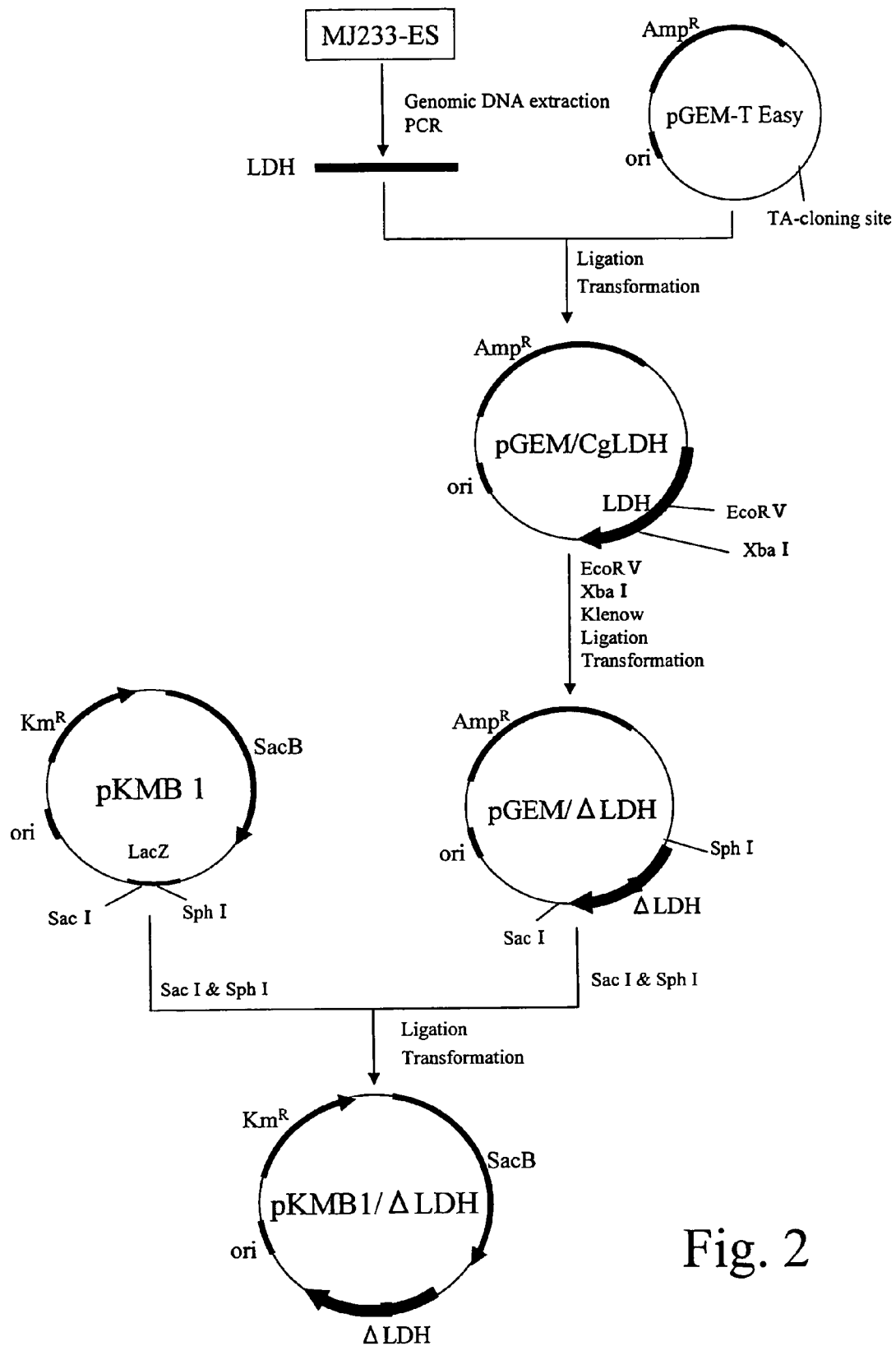
FIG. 2 shows the procedure for constructing the plasmid pKMB1/ΔLDH.

Clones each forming a white colony on this medium was subjected to liquid culture by a conventional method, and then the plasmid DNA was isolated. The obtained plasmid DNA was digested with restriction enzymes SacI and SphI. A clone having an insert of about 0.75 kb was selected and named pKMB1/ΔLDH (FIG. 2).

(D) Construction of Lactate Dehydrogenase Gene-Disrupted Strain Derived from *Brevibacterium flavum* MJ233-ES strain A plasmid DNA to be used for transformation of the *Brevibacterium flavum* MJ-233 strain was isolated from *Escherichia coli* JM110 strain transformed with pKMB1/ΔLDH by a calcium chloride method (Journal of Molecular Biology, 53, 159, 1970).

Endogenous plasmids were removed from *Brevibacterium flavum* MJ233 strain (FERM BP-1497) (curing) according to the conventional procedures (Wolf H et al., J. Bacteriol. 1983, 156 (3) 1165-1170, Kurusu Y et al., Agric Biol Chem. 1990, 54(2) 443-7) and then, the resulting plasmid-cured strain *Brevibacterium flavum* MJ233-ES was used for subsequent transformation.

The transformation of the *Brevibacterium flavum* MJ233-ES strain was performed by an electric pulse method (Res. Microbiolo., Vol. 144, p. 181-185, 1993), and the obtained transformant was spread on an LBG agar medium (10 g of tryptone, 5 g of yeast extract, 5 g of NaCl, 20 g of glucose, and 15 g of agar dissolved in 1 L of distilled water) containing 50 μg/mL kanamycin.

Because pKMB1/ΔLDH is a plasmid incapable of replicating in the *Brevibacterium flavum* MJ233-ES strain, a strain grown on this medium must have a kanamycin-resistant gene and SacB gene derived from the plasmid on its genome, as a result of homologous recombination between a lactate dehydrogenase gene on the plasmid and the same gene on the genome of the *Brevibacterium flavum* MJ-233 strain.

Next, the strain obtained by homologous recombination was subjected to liquid culture on an LBG medium containing 50 μg/mL kanamycin. The culture solution supposed to contain about 1,000,000 bacterial cells was spread on an LBG medium containing 10% sucrose. As a result, about 10 sucrose-insensitive strains in which the SacB gene was removed by the second homologous recombination were obtained.

The obtained strains include: a strain in which the lactate dehydrogenase gene was replaced by a deletion type derived from pKMB1/ΔLDH; and a strain in which the lactate dehydrogenase gene reverted to a wild type. Whether the lactate dehydrogenase gene is a deletion type or a wild type can be confirmed easily by subjecting a bacterial strain obtained by liquid culture in an LBG medium to direct PCR and detecting the lactate dehydrogenase gene. Analysis of the lactate dehydrogenase gene by using primers (SEQ ID NOS: 7 and 8) for PCR amplification results in a DNA fragment of 720 bp for a wild type and a DNA fragment of 471 bp for a deletion type.

As a result of the analysis of the sucrose-insensitive strain by the above-mentioned method, a strain having only a deletion type gene was selected and named *Brevibacterium flavum* MJ233/ΔLDH.

(E) Measurement of Lactate Dehydrogenase Activity

*Brevibacterium flavum* MJ233/ΔLDH strain prepared by the above (D) was inoculated into the culture medium A and then aerobically cultured at 30° C. for 15 hour with shaking. The resulting culture was centrifuged (3,000×g, 4° C. for 20 minutes) and bacterial cells were then collected, followed by washing with sodium-phosphate buffer (50 mM sodium phosphate buffer (pH 7.3)).

Subsequently, 0.5 g (wet weight) of washed bacterial cells was suspended in 2 ml of the above sodium-phosphate buffer and then treated with ultrasonicator (manufactured by Branson, Ltd.) on ice to obtain a lysis product of bacterial cells. The lysis product was centrifuged (10,000×g, 4° C. for 30 minutes) and the supernatant was then obtained as a crude enzyme solution. Similarly, a crude enzyme solution of *Brevibacterium flavum* MJ233-ES strain was prepared as a control and then subjected to the following activity measurement.

The lactate dehydrogenase activity was measured by determining the oxidation of coenzyme NADH to AND$^+$ as a change in absorbance at 340 nm in connection with the generation of lactic acid from pyruvic acid as a substrate (L. Kanarek and R. L. Hill, J. Biol. Chem. 239, 4202 (1964)). The reaction was carried out at 37° C. in 50 mM potassium-phosphate buffer (pH 7.2) in the presence of 10 mM pyruvic acid and 0.4 mM NADH. Consequently, the lactate dehydrogenase activity of the crude enzyme solution prepared from *Brevibacterium flavum* MJ233/ΔLDH strain was one tenth or less of the lactate dehydrogenase activity of the crude enzyme solution prepared from *Brevibacterium flavum* MJ233-ES strain.

Example 3

Construction of Expression Vector for Coryneform Bacterium (A) Preparation of a Promoter Fragment for Coryneform Bacterium A DNA fragment (hereinafter, referred to TZ4 promoter) shown in SEQ ID NO: 4 in JP07-95891A and reported to have high promoter activity in a coryneform bacterium was used. The promoter fragment was obtained by performing PCR by using the *Brevibacterium flavum* MJ233 genomic DNA prepared in the section (A) of Example 2 as a template; and using synthetic DNAs (SEQ ID NOS: 9 and 10) designed based on a sequence described as SEQ ID NO: 4 in JP07-95891A, as primers.

The composition of the reaction solution is as follows: 1 μL of the template DNA, 0.2 μL of PfxDNA polymerase (available from Invitrogen Japan K.K.), 1 time concentration of a supplied buffer, 0.3 μM of respective primers, 1 mM MgSO$_4$, and 0.25 μM dNTPs were mixed, and a total volume of the reaction solution was adjusted to 20 μL.

Reaction temperature condition is as follows: The DNA Thermal Cycler PTC-2000 manufactured by MJ Research Co., Ltd. was used and a cycle of 94° C. for 20 seconds, 60° C. for 20 seconds, and 72° C. for 30 seconds was repeated 35 times. For the first cycle, heat-retention at 94° C. was conducted for 1 minute 20 seconds. For the last cycle, the heat-retention at 72° C. was conducted for 2 minutes.

The amplified product was analyzed by separating in 2.0% agarose (SeaKem GTG agarose, available from FMC Bio-Products) gel electrophoresis and visualizing with ethidium bromide staining, to thereby detect a fragment of about 0.25 kb. The target DNA fragment was recovered from the gel by using the QIAQuick Gel Extraction Kit (available from QIAGEN).

The 5'-end of the recovered DNA fragment was phosphorylated with T4 Polynucleotide Kinase (available from Takara Shuzo Co., Ltd.) and was ligated to an SmaI site of an *Escherichia coli* vector pUC 19 (Takara Shuzo Co., Ltd.) by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL ampicillin and 50 μg/mL X-Gal.

Six clones each forming a white colony on this medium were subjected to liquid culture by a conventional method, and then the plasmid DNA was isolated, and the nucleotide sequence was determined. Of those, a clone having a TZ4 promoter inserted therein so to have transcription activity in an opposite direction with respect to the lac promoter on pUC 19 was selected and named pUC/TZ4.

Next, a DNA linker consisting of synthetic DNAs (SEQ ID NOS: 11 and 12) each having phosphorylated 5'-ends and having sticky ends corresponding to each of BamHI and PstI was added to the DNA fragment prepared by digesting pUC/TZ4 with restriction enzymes BamHI and PstI, and ligated with each other by using the Ligation Kit ver. 2 (available from Takara Shuzo Co., Ltd.), and the obtained plasmid DNA was used to transform the *Escherichia coli* (DH5α strain). This DNA linker includes a ribosome binding sequence (AG-GAGG) and a cloning site (the order of PacI, NotI, and ApaI from upstream) arranged downstream of the ribosome binding sequence.

Clones each forming a white colony on this medium were subjected to liquid culture by a conventional method, and then the plasmid DNA was isolated. Of the obtained plasmid DNAs, a plasmid DNA capable of being cleaved with a restriction enzyme NotI was selected and named pUC/TZ4-SD.

A promoter fragment of about 0.3 kb was obtained by digesting the pUC/TZ4-SD with a restriction enzyme PstI, making its end blunt with the Klenow Fragment, and cleaving the resultant DNA with a restriction enzyme KpnI, and separated in 2.0% agarose gel electrophoresis, and recovered.

(B) Construction of Expression Vector for Coryneform Bacterium pHSG298par-rep described in JP12-93183A was used as a plasmid capable of stable and autonomous replication in coryneform bacteria. This plasmid includes a replicating region and a region having a stabilization function of a natural plasmid pBY503 from *Brevibacterium stationis* IFO12144 strain, a kanamycin resistant gene derived from an *Escherichia coli* vector pHSG298 (Takara Shuzo Co., Ltd.), and a replicating region for *Escherichia coli*. A DNA was prepared by digesting pHSG298par-rep with a restriction enzyme SseI, making its end blunt with the Klenow Fragment, and digesting the resultant DNA with the restriction enzyme KpnI, and the DNA was mixed with the TZ4 promoter fragment prepared in the above section (A) and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin.

Figure 3:
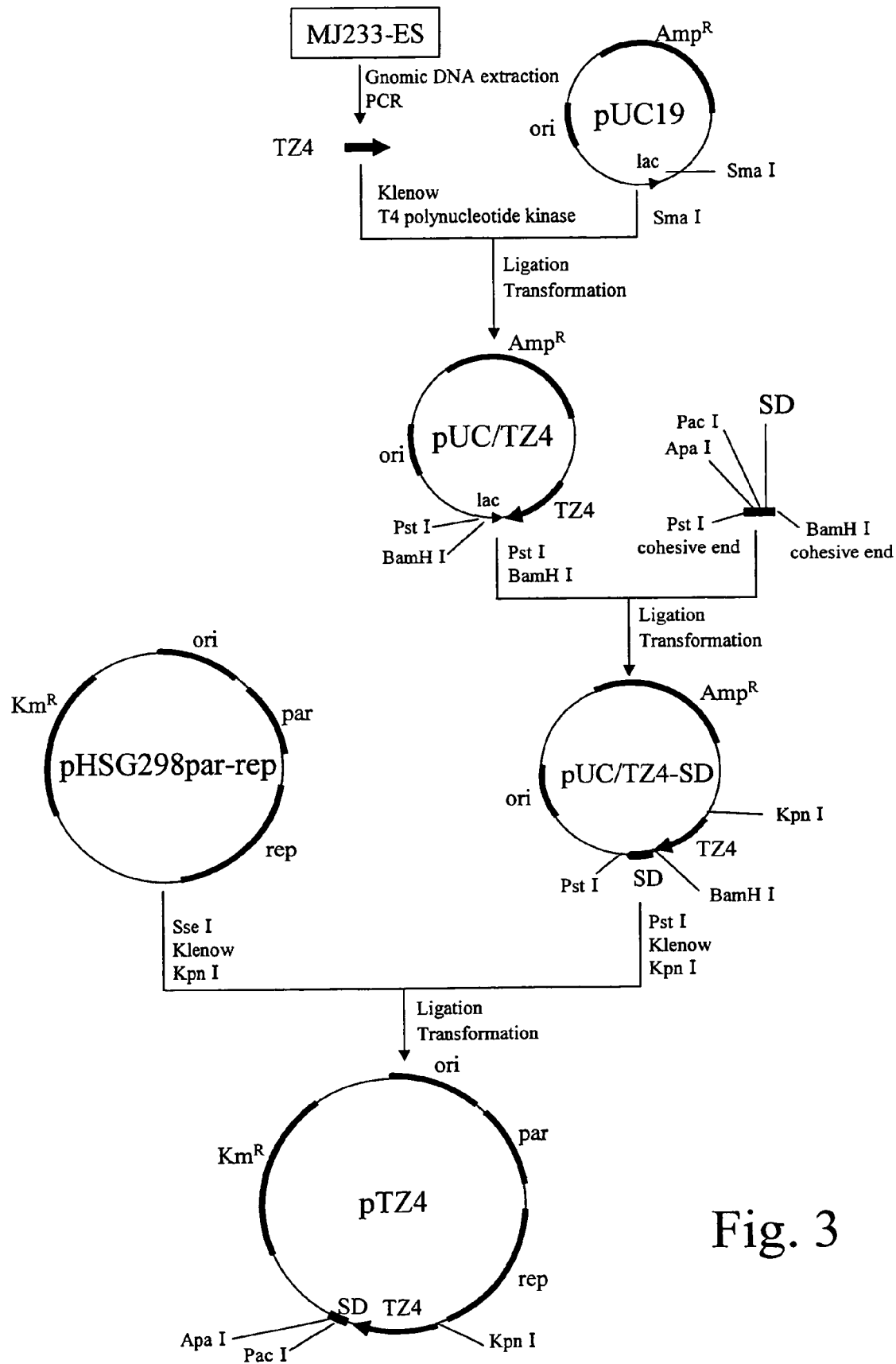
FIG. 3 shows the procedure for constructing the plasmid pTZ4.

A strain grown on this medium was subjected to liquid culture by a conventional method, and then the plasmid DNA was purified. Of the obtained plasmid DNA, a plasmid DNA capable of being digested with the restriction enzyme NotI was selected and named pTZ4 (FIG. 3 shows the construction procedure).

Example 4

Construction of Pyruvate Carboxylase Activity-Enhanced Strain (A) Acquisition of a Pyruvate Carboxylase Gene A pyruvate carboxylase gene derived from the *Brevibacterium flavum* MJ233 strain was obtained by performing PCR by using the DNA prepared in the section (A) of Example 2 as a template; and using synthetic DNAs (SEQ ID NOS: 13 and 14) designed based on a sequence of a pyruvate carboxylase gene of a *Corynebacterium glutamicum* ATCC 13032 strain whose entire genomic sequence was reported (GenBank Database Accession No. AP005276). The composition of the reaction solution is as follows: 1 μL of the template DNA, 0.2 μL of PfxDNA polymerase (available from Invitrogen Japan K. K.), 1-fold concentration of the supplied buffer, 0.3 μM of respective primers, 1 mM MgSO$_4$, and 0.25 μM dNTPs were mixed, and a total volume of the reaction liquid was adjusted to 20 μL.

Reaction temperature condition is as follows: The DNA Thermal Cycler PTC-2000 manufactured by MJ Research Co., Ltd. was used and a cycle of 94° C. for 20 seconds and 68° C. for 4 minutes was repeated 35 times. For the first cycle, heat-retention at 94° C. was conducted for 1 minute 20 seconds. For the last cycle, the heat-retention at 68° C. was conducted for 10 minutes. After completion of PCR, 0.1 M of Takara Ex Taq (Takara Shuzo Co., Ltd.) was added and kept at 72° C. for 30 minutes.

The amplified product was analyzed by separating in 0.75% agarose (SeaKem GTG agarose, available from FMC BioProducts) gel electrophoresis and visualizing with ethidium bromide staining, to thereby detect a fragment of about 3.7 kb. The target DNA fragment was recovered from the gel by using the QIAQuick Gel Extraction Kit (available from QIAGEN).

The recovered DNA fragment was mixed with the PCR product-cloning vector pGEM-TEasy (available from Promega Corporation) and ligated thereto by using the Ligation Kit ver. 2 (available from Takara Shuzo Co., Ltd.), and the obtained plasmid DNA was used to transform *Escherichia coli* (DH5α strain). The obtained recombinant *Escherichia coli* was spread on an LB agar medium containing 50 μg/mL ampicillin and 50 μg/mL X-Gal.

Clones each forming a white colony on this medium were subjected to liquid culture by a conventional method, and then the plasmid DNA was isolated. The obtained plasmid DNA was digested with restriction enzymes PacI and ApaI. The plasmid DNA was confirmed to have an insert of about 3.7 kb and named pGEM/MJPC.

A nucleotide sequence of the insert in pGEM/MJPC was determined by using the nucleotide sequencing device (model 377 XL, manufactured by Applied Biosystems) and BigDye Terminator Cycle Sequencing Kit ver. 3 (manufactured by Applied Biosystems). SEQ ID NO: 15 shows the determined nucleotide sequence and a predicted amino acid sequence. The amino acid sequence is extremely highly homologous (99.4%) to that derived from the *Corynebacterium glutamicum* ATCC 13032 strain, concluding that the pGEM/MJPC insert was a pyruvate carboxylase gene derived from the *Brevibacterium flavum* MJ233 strain.

(B) Construction of Plasmid for Enhancing Pyruvate Carboxylase Activity

Next, the pyruvate carboxylase gene fragment of about 3.7 kb obtained by digesting pGEM/MJPC with the restriction enzymes PacI and ApaI in the above section (A) was separated in 0.75% agarose gel electrophoresis, and recovered.

This DNA fragment was mixed with pTZ4 digested with the restriction enzymes PacI and ApaI in Example 3 and ligated thereto by using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin.

Figure 4:
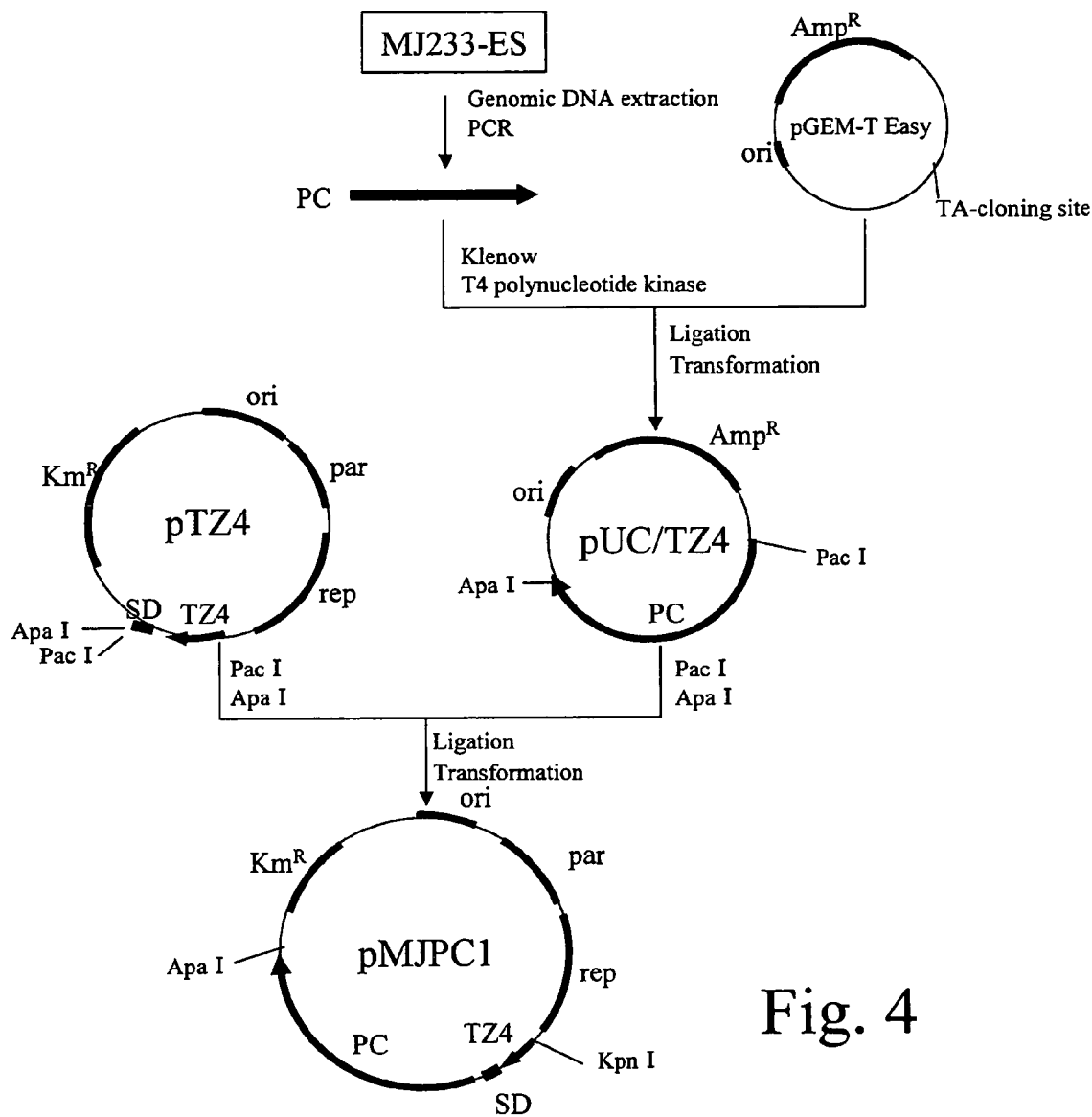
FIG. 4 shows the procedure for constructing the plasmid pMJPC1.

Strains grown on this medium were subjected to liquid culture by a conventional method, and then the plasmid DNA was purified. The obtained plasmid DNA was digested with restriction enzymes PacI and ApaI. A clone having an insert of about 3.7 kb was selected and named pMJPC1 (FIG. 4).

(C) Transformation of *Brevibacterium flavum* MJ233/ΔLDH Strain

A plasmid DNA pMJPC1 which is capable of replicating in the *Brevibacterium flavum* MJ233 strain was isolated from the *Escherichia coli* (DH5α strain) transformed in the above section (B).

The transformation of the *Brevibacterium flavum* MJ233/ΔLDH strain was performed by the electric pulse method (Res. Microbiolo., Vol. 144, p. 181-185, 1993), and the obtained transformant was spread on an LBG agar medium (10 g of tryptone, 5 g of yeast extract, 5 g of NaCl, 20 g of glucose, and 15 g of agar dissolved in 1 L of distilled water) containing 50 μg/mL kanamycin.

A strain grown on this medium was subjected to liquid culture by a conventional method, and then the plasmid DNA was extracted and analyzed with restriction enzyme digestion. The results confirmed that the strain retained pMJPC1, and the strain was named *Brevibacterium flavum* MJ233/PC/ΔLDH strain.

(D) Pyruvate Carboxylase Activity

The transformant strain *Brevibacterium flavum* MJ233/PC/ΔLDH obtained in the above section (C) was cultured overnight in 100 ml of the culture medium A containing 2% glucose and 25 mg/l kanamycin. The obtained bacterial cells were harvested and then washed with 50 ml of 50 mM potassium phosphate buffer (pH 7.5), followed by re-suspension in 20 ml of buffer having the same composition as mentioned above. The suspension was subjected to sonication with SONIFIER 350 (manufactured by Branson) and the centrifuged supernatant was then provided as cell-free extracts. The pyruvate carboxylase activity was determined using the resulting cell-free extracts. The measurement of enzyme activity was carried out by allowing the enzyme to react at 25° C. in a reaction solution containing 100 mM Tris/HCl buffer (pH 7.5), 0.1 mg/10 ml biotin, 5 mM magnesium chloride, 50 mM sodium hydrogen carbonate, 50 mM sodium pyruvate, 5 mM adenosine triphosphate disodium, 0.32 mM NADH, 20 units/1.5 ml malate dehydrogenase (manufactured by WAKO, originated from yeast). One unit (1 U) was defined as the amount of enzyme for catalyzing a decrease of 1 μmol of NADH per minute. The specific activity in the cell-free extracts of the strain transformed with pyruvate carboxylase gene was 0.2 U/mg of protein. On the other hand, from the bacterial cells prepared by similarly incubating the parent MJ233/ΔLDH strain using the culture medium A, no pyruvate carboxylase activity was detected by the activity measurement method.

Example 5

Cloning of *Escherichia coli* Fumarate Reductase Gene (A) Extraction of *Escherichia coli* DNA

*Escherichia coli* JM109 strain was incubated in 10 ml of LB culture medium until the late stage of the logarithmic growth phase, and the resulting bacterial cells were then subjected to the method described in the section (A) of Example 1 to prepare a genomic DNA.

(B) Cloning of *Escherichia coli* Fumarate Reductase Gene

The *Escherichia coli* fumarate reductase gene was obtained by PCR using the DNA prepared in the above section (A) as a template and synthetic DNAs (SEQ ID NOS: 17 and 18) designed on the basis of the sequence of the gene of *Escherichia coli* K12-MG 1655 strain whose the whole genome sequence had been reported (GenBank Database Accession NO. U00096).

Composition of reaction solution is as follows: 1 μL of template DNA, 0.2 μL of PfxDNA polymerase (manufactured by Invitrogen Co., Ltd.), 1-fold concentration of the supplied buffer, 0.3 μM of respective primers, 1 mM MgSO$_4$, and 0.25 μM of dNTPs were mixed, and the total volume was adjusted to 20 μL.

Reaction temperature condition is as follows: The DNA Thermal Cycler PTC-2000 manufactured by MJ Research Co., Ltd. was used and a cycle of 94° C. for 20 seconds and 68° C. for 4 minutes was repeated 35 times. For the first cycle, heat-retention at 94° C. was conducted for 1 minute 20 seconds. For the last cycle, the heat-retention at 68° C. was conducted for 10 minutes. After completion of PCR, 0.1 M of Takara Ex Taq (Takara Shuzo Co., Ltd.) was added and kept at 72° C. for 30 minutes.

The amplified product was analyzed by separating in 0.75% agarose (Sea Kem GTG agarose: manufactured by FMC BioProducts) gel electrophoresis and then visualized with ethidium bromide staining, thereby detecting a fragment of about 3.8 kb. The DNA fragment of interest was isolated from the gel by QIA Quick Gel Extraction Kit (manufactured by QIAGEN).

The recovered DNA fragment was mixed with the PCR product-cloning vector pT7 Blue T-Vector (manufactured by Novagen) and ligated thereto by Ligation Kit ver. 2 (manufactured by Takara Shuzo Co., Ltd.), and the obtained plasmid DNA was used to transform *Escherichia coli* (DH5α strain). The obtained recombinant *Escherichia coli* was spread on an LB agar culture medium containing 50 μg/mL ampicillin and 50 μg/mL X-Gal.

A clone forming a white colony on the culture medium was incubated in liquid culture according to a conventional method, followed by purifying the plasmid DNA. The resulting plasmid DNA was digested with restriction enzymes HindIII and KpnI, thereby confirming an insert fragment of about 3.9 kb, and named pFRD6.0.

The nucleotide sequence of the insert fragment of pFRD6.0 was determined using the nucleotide sequencing device (model 377XL) manufactured by Applied Biosystems, Inc. and BigDye Terminator Cycle Sequencing Kit ver. 3. The resulting nucleotide sequences and predicted amino acid sequences are described in SEQ ID NOS: 19 and 20-23.

Example 6

Construction of a Strain with Enhanced Activities of Pyruvate Carboxylase/Fumarate Reductase (A) Modification of a Restriction Enzyme Recognition Site of pMJPC1 pMJPC1 constructed in Example 3 was completely digested with the restriction enzyme KpnI, and its 5'-ends was dephosphorylated by a reaction with Calf intestine Alkaline Phosphatase (Takara Shuzo Co., Ltd.). The DNA linker consisting of the synthetic DNAs with phosphorylated 5'-ends (SEQ ID NOS: 24 and 25) was mixed with the obtained fragment and ligated thereto using the Ligation Kit ver. 2 (available from Takara Shuzo Co., Ltd.), and the obtained plasmid DNA was used to transform the *Escherichia coli* (DH5α strain). The obtained recombinant *Escherichia coli* was spread on an LB agar medium containing 50 μg/mL kanamycin.

A strain grown on this medium was subjected to liquid culture by a conventional method, and then the plasmid DNA was isolated. Of the obtained plasmid DNA, a plasmid DNA which can be digested with the restriction enzyme NdeI was selected and named pMJPC1.1.

(B) Construction of a Plasmid for Enhancing Activities of Pyruvate Carboxylase and fumarate Reductase A DNA fragment of about 3.9 kb was obtained by digesting pFRD6.0 prepared in Example 5 with the restriction enzyme HindIII, and making its end blunt with the Klenow Fragment, and digesting with the restriction enzyme KpnI. The DNA fragment was separated in 0.75% agarose gel electrophoresis, and recovered. The prepared fragment containing the *Escherichia coli* fumarate reductase gene was mixed and ligated, by using the Ligation Kit ver. 2 (available from Takara Shuzo Co., Ltd.), to the DNA which was obtained by digesting pMJPC1.1 prepared in the above section (A) with the restriction enzyme NdeI, making its end blunt with the Klenow Fragment, followed by digestion with the restriction enzyme KpnI. The obtained plasmid DNA was used to transform *Escherichia coli* (DH5α strain). The obtained recombinant *Escherichia coli* was spread on an LB agar medium containing 50 μg/mL kanamycin.

Figure 5:
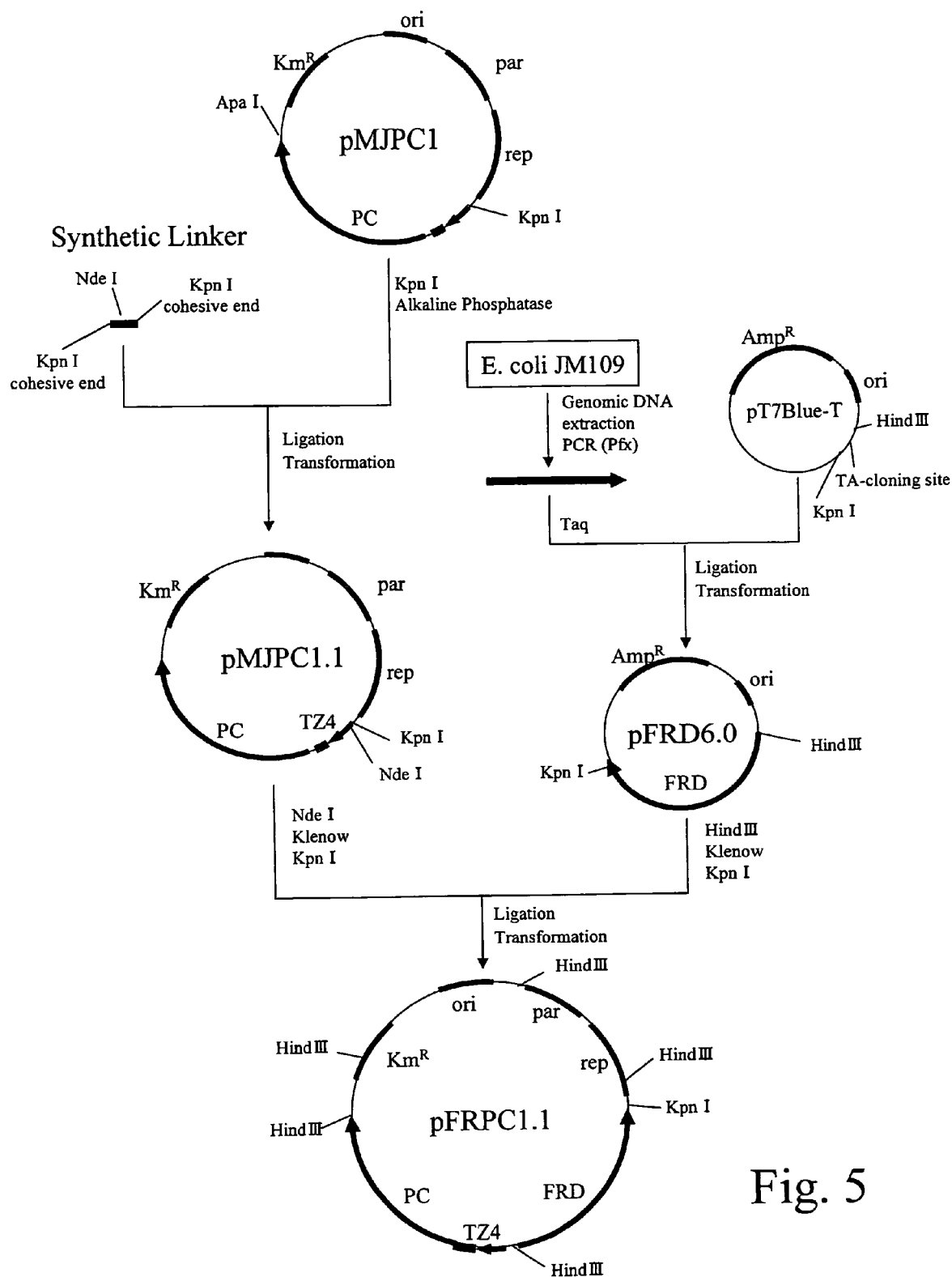
FIG. 5 shows the procedure for constructing the plasmid pFRPC1.1.

A strain grown on this medium was subjected to liquid culture by a conventional method, and then the plasmid DNA was isolated. The obtained plasmid DNA showed fragments of 505, 2,132, 2,675, 3,775, and 4,193 bp after restriction enzyme HindIII digestion. Thus, it was concluded that the DNA has the structure shown in FIG. 5, and the plasmid was named pFRPC1.1.

(B) Transformation of *Brevibacterium flavum* MJ233/ΔLDH strain

The transformation of the *Brevibacterium flavum* MJ233/ΔLDH strain with pFRPC1.1 was performed by the method described in the section (C) of Example 4, to thereby obtain a strain having the plasmid pFRPC1.1. This strain was named *Brevibacterium flavum* MJ233/FRD/PC/ΔLDH strain.

(C) FRD Enzyme Activity Measurement

The transformant, *Brevibacterium flavum* MJ233/FRD/PC/ΔLDH strain, prepared by the above section (B) was cultured overnight in 100 ml of the culture medium A containing 2% glucose and 25 mg/L kanamycin. The resulting bacterial cells were collected and washed with 50 ml of 50 mM potassium phosphate buffer (pH 7.5), followed by resuspension in 20 ml of buffer having the same composition as mentioned above. The suspension was subjected to sonication with SONIFIER 350 (manufactured by Branson) and the centrifuged supernatant was used as cell-free extracts. The fumarate reductase activity was determined using the cell-free extracts. The measurement of enzyme activity was carried out by allowing the extracts to react at 25° C. in a reaction solution containing 33 mM Tris/HCl buffer (pH 7.5), 0.1 mM EDTA, 20 mM sodium succinate, 2 mM $K_3Fe(CN)_6$. One unit (1 U) was defined as the amount of the enzyme for catalyzing a decrease of 2 μmol of $K_3Fe(CN)_6$ per minute. The specific fumarate reductase activity in the cell-free extracts of the strain expressing the plasmid pFRRC1.1 was 0.02 U/mg-protein. On the other hand, in the bacterial cells prepared by similarly culturing the parent MJ233/ΔLDH strain in the culture medium A, the specific activity was 0.01 U/mg-protein.

Example 7

Cloning of Succinate Dehydrogenase Gene of Coryneform Bacterium

Figure 6:
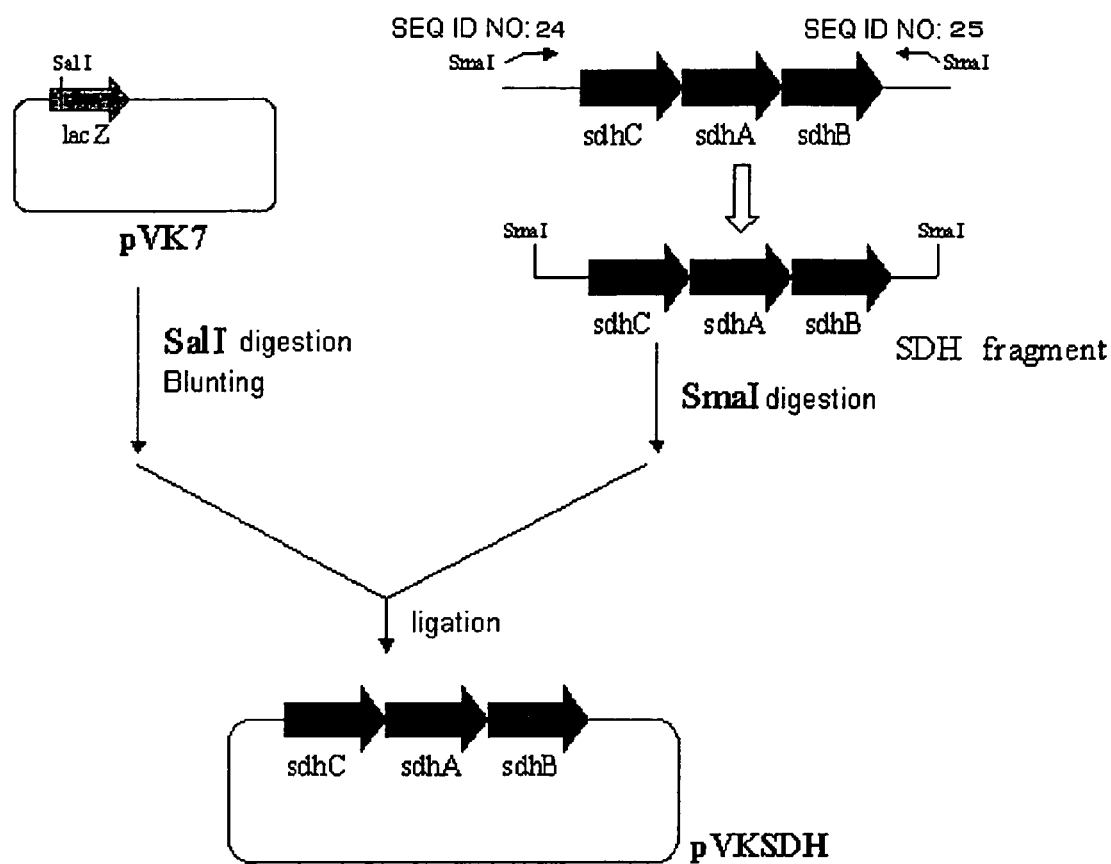
FIG. 6 shows the procedure for constructing the plasmid pVKSDH.

Succinate dehydrogenase (SDH) genes (hereinafter, referred to as sdhC, sdhA, and sdhB) of *Brevibacterium flavum* MJ233 strain were obtained by PCR using synthetic DNAs designed based on the nucleotide sequences of the genes of *Corynebacterium glutamicum* ATCC 13032 (GenBank Database Accession NO. NC_003450) as primers. Specifically, a DNA fragment (SEQ ID NO: 28) containing the gene forming an operon comprising sdhC-sdhA-sdhB was obtained by PCR using synthetic DNAs having SEQ ID NOS: 26 and 27 as primers and using the chromosomal DNA of *Brevibacterium flavum* MJ233 as a template. The PCR was carried out using KOD-PLUS-(manufactured by TOYOBO Co., Ltd.) according to the condition that one step of heat-retention at 94° C. for 5 minutes was performed and then a cycle of denature at 94° C. for 15 seconds, annealing at 56° C. for 30 seconds, and elongation at 72° C. for 4 minutes was repeated 25 times. The obtained PCR product was purified by a conventional procedure and then digested with SmaI. The DNA fragment was mixed and ligated, using Ligation Kit ver. 2 (manufactured by Takara Bio Inc.), to the DNA fragment which was prepared by digesting pVK7 (JP10-215883A) with SalI followed by blunting with DNA-Blunting Kit (manufactured by Takara Bio Inc.). This plasmid was used to transform competent cells of *Escherichia coli* JM109 (manufactured by Takara Bio Inc.) and the transformant was then spread on an LB culture containing 25 μg/ml kanamycin (hereinafter, abbreviated as Km), followed by overnight culture. Subsequently, colonies formed were picked up and single colonies were isolated, and thereby transformants were obtained. Plasmid was extracted from the transformants, and the plasmid in which a PCR product was inserted was named as pVKSDH. The procedures of constructing pVKSDH is shown in FIG. 6.

Example 8

Figure 7:
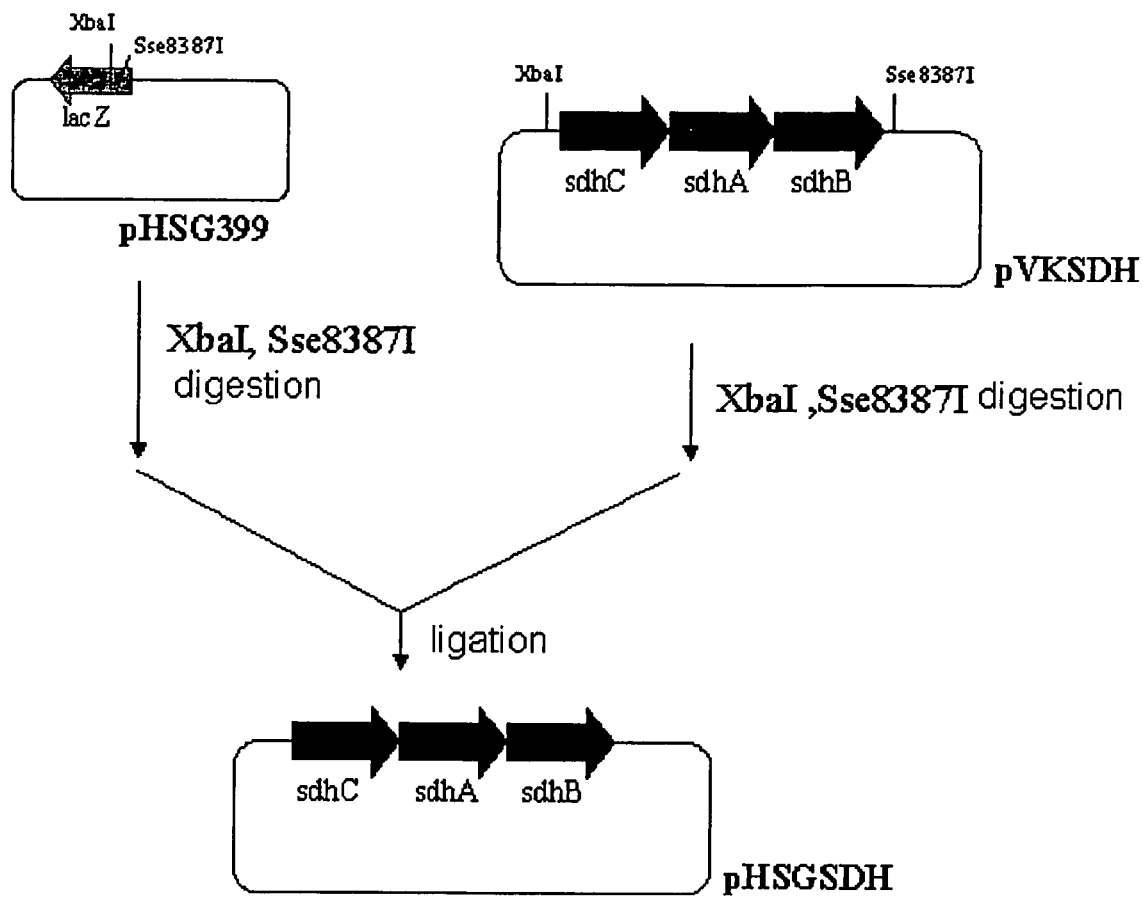
FIG. 7 shows the procedure for constructing the plasmid pHSGSDH.

Construction of a Plasmid for Enhancing Activities of Pyruvate Carboxylase and Succinate Dehydrogenase A DNA fragment containing three genes of sdhC, sdhA, and sdhB, which was obtained by digesting the pVKSDH constructed in Example 7 with XbaI and Sse8371, was mixed and ligated, by DNA Ligation Kit ver. 2 (manufactured by Takara Bio Inc.), to the fragment prepared by digesting pHSG399 (manufactured by Takara Bio Inc.) with XbaI and Sse83871. This DNA was used to transform competent cells of *Escherichia coli* JM109 (manufactured by Takara Bio Inc.) and the transformants were then spread on an LB culture containing 25 μg/ml chloramphenicol (hereinafter, abbreviated as Cm), 50 μg/ml X-Gal, and 1 mM IPTG, followed by overnight culture. Subsequently, appeared white colonies were picked up and single colonies were isolated, thereby transformants were obtained. Plasmid was extracted from the transformants and the plasmid, in which the DNA fragment containing sdhC, sdhA, and sdhB was inserted, was named as pHSGSDH (FIG. 7).

Figure 8:
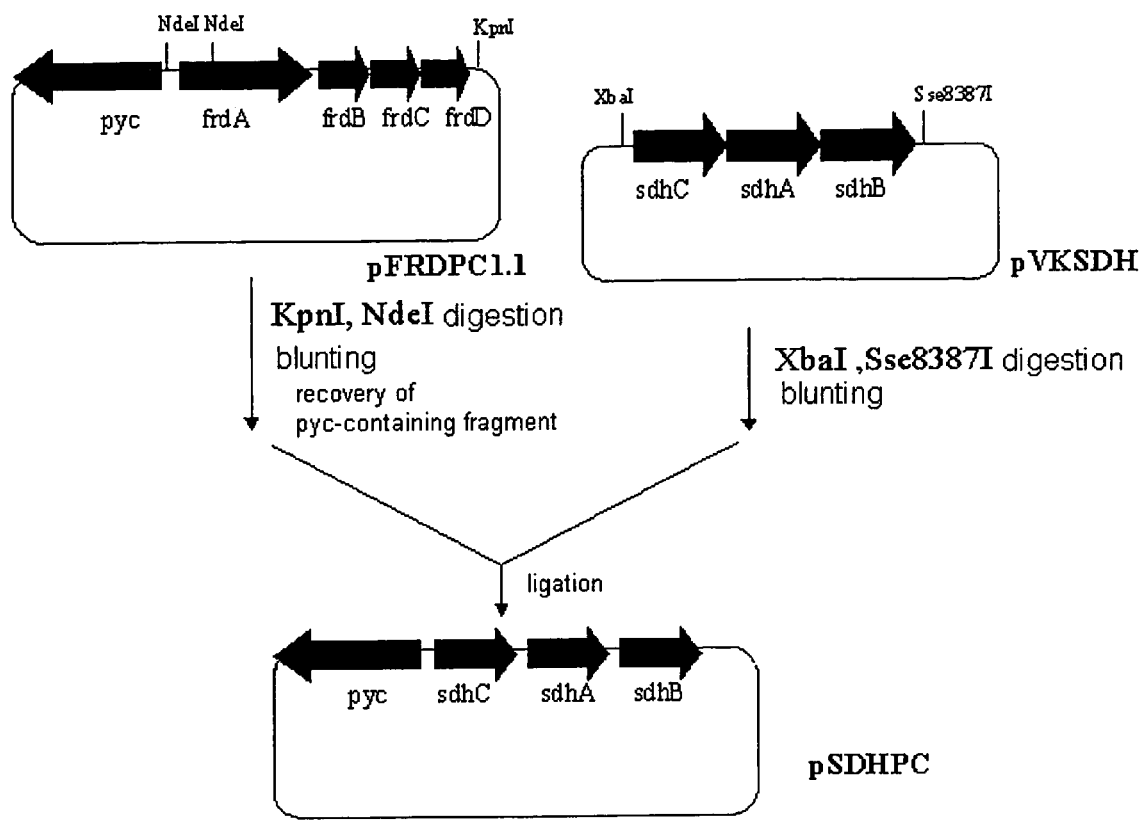
FIG. 8 shows the procedure for constructing the plasmid pSDHPC.

On the other hand, by digesting the plasmid pFRPC1.1 carrying the fumarate reductase gene of *Escherichia coli* described in Example 6 and the pyc gene from *Brevibacterium flavum*, with KpnI and NdeI, it is possible to recover a fragment containing the remaining region except the fumarate reductase gene from *Escherichia coli*. Therefore, pFRPC1.1 was digested with KpnI and NdeI and blunt-ended, and a fumarate reductase gene was removed, and the remaining DNA fragment was recovered. The DNA fragment containing sdhC, sdhA, and sdhB obtained by digestion of pHSGSDH with XbaI and Sse83871 was blunt-ended and then ligated to the recovered DNA fragment. This DNA was used to transform competent cells of *Escherichia coli* JM109 (manufactured by Takara Bio Inc.) and the transformants were spread on an LB culture containing 25 μg/ml Km, followed by overnight culture. Subsequently, appeared colonies were picked up and single colonies were isolated, thereby transformants were obtained. Plasmids were extracted from the transformants, and the plasmid, in which the DNA fragment containing sdhC, sdhA, and sdhB was inserted while frdA, frdB, frdC, and frdD genes were removed, was named as pSDHPC (FIG. 8).

Example 9

Construction of a Strain in which Pyruvate Carboxylase and Succinate Dehydrogenase are Enhanced Both pVKSDH and pSDHPC obtained respectively in Example 7 and Example 8 were capable of autonomous replication in cells of coryneform bacterium. Thus, each of the plasmids was used for the transformation of coryneform bacterium, and thereby transformants were obtained. The MJ233/ΔLDH strain constructed in Example 2 was transformed with each of pVKSDH and pSDHPC by the electrical pulse method and was then spread on a 25-μg/ml kanamycin-containing CM-Dex culture medium (5 g/L glucose, 10 g/L polypeptone, 10 g/L yeast extract, 1 g/L KH$_2$PO$_4$, 0.4 g/L MgSO$_4$.7H$_2$O, 0.01 g/L FeSO$_4$.7H$_2$O, 0.01 g/L MnSO$_4$.7H$_2$O, 3 g/L urea, 1.2 g/L soybean hydrolysate, pH 7.5 (KOH), and 15 g/L agar), followed by culture at 31.5° C. for about 24 hours.

The strain grown on this culture medium is a strain in which the plasmid is introduced. The obtained transformants were named MJ233/SDH/ΔLDH and MJ233/SDH/PC/ΔLDH, respectively. Furthermore, for preparing a control strain, the plasmid pVK7 and the plasmid pMJPC1 constructed in Example 4 were introduced into the MJ233/ΔLDH strain by the above method. The obtained transformants were named MJ233/ΔLDH/pVK7 and MJ233/PC/ΔLDH, respectively.

Example 10

Bacterial Cell Reaction

Ammonium Carbonate Neutralization, Semi-Aerobic Reaction 100 ml of a culture medium (containing 4 g of urea, 14 g of ammonium sulfate, 0.5 g of monobasic potassium phosphate, 0.5 g of dibasic potassium phosphate, 0.5 g of magnesium sulfate.7 hydrate, 20 mg of ferrous sulfate.7 hydrate, 20 mg of manganese sulfate-hydrate, 200 μg of D-biotin, 200 μg of thiamin hydrochloride, 1 g of yeast extract, 1 g of casamino acid, and 1000 ml of distilled water) was poured into a 500-mL conical flask and then heat-sterilized at 120° C. for 20 minutes. It was cooled to room temperature and then added with 4 mL of a 50% aqueous glucose solution, which had been previously sterilized, and 50 μL of a 5% kanamycin solution, which had been sterilized by filtration, and used for seed culture of *Brevibacterium flavum* MJ233/FRD/PC/ΔLDH strain prepared in Example 6(B) at 30° C. for 24 hours. A culture medium containing 12 g of urea, 42 g of ammonium sulfate, 1.5 g of potassium phosphate, 1.5 g of potassium diphosphate, 1.5 g of magnesium sulfate.7 hydrate, 60 mg of ferrous sulfate.7 hydrate, 60 mg of manganese sulfate-hydrate, 600 μg of D-biotin, 600 μg of thiamin hydrochloride, 3 g of yeast extract, 3 g of casamino acid, 1 ml of antifoaming agent (Adecanol LG294: manufactured by Asahi Denka Kogyo K. K.), and 2,500 mL of distilled water was poured into a 5-L fermenter, and then heat-sterilized at 120° C. for 20 minutes. It was cooled to room temperature and then added with 500 mL of 12% aqueous glucose solution which had been previously sterilized, and the whole amount of the seed culture was added into the medium, and cultured at 30° C. The main culture was carried out with aeration at a rate of 500 mL per minute and agitation at a rate of 500 rpm. After 12 hours, the glucose was almost completely consumed.

A culture medium containing 0.2 g of magnesium sulfate.7 hydrate, 8 mg of ferrous sulfate.7 hydrate, 8 mg of manganese sulfate.hydrate, 80 μg of D-biotin, 80 μg of thiamin hydrochloride, 1 mL of antifoaming agent (Adecanol LG294: manufactured by Asahi Denka Kogyo K. K.), and 200 mL of distilled water was poured into a 500-mL conical flask and then heat-sterilized at 120° C. for 20 minutes. After it had been cooled to room temperature, the medium was added to the bacterial cells harvested by centrifugation at 8,000 rpm for 5 minutes from the culture solution obtained by the main culture as described above so that the cells are re-suspended at O.D. (660 nm) of 60. In a 1-litter jar fermenter, 200 ml of the suspension and 200 ml of a pre-sterilized 20% glucose solution were added and then kept warm at 35° C. The pH was kept at 7.6 with 2 M ammonium carbonate, and the reaction was carried out with aeration at a rate of 100 mL per minute and agitation at a rate of 400 rpm.

In about 20 hours after initiating the reaction, glucose was almost completely consumed. The glucose consumption rate was 5.00 g/L/h, the succinate production rate was 2.66 g/L/h, and the yield thereof was 70.1%. In contrast, when *Brevibacterium flavum* MJ233/PC/ΔLDH strain prepared in Example 4(c) was reacted in the same way as described above, the glucose consumption rate was 4.74 g/L/h, the succinate production rate was 2.13 g/L/h, and the yield thereof was 58.7%.

Example 11

Bacterial Cell Reaction

Ammonium Carbonate Neutralization, Anaerobic Reaction

A reaction suspension was prepared in the same way as Example 10 described above and the pH was kept at 7.6 with 2 M ammonium carbonate, and a reaction was conducted with agitation at 200 rpm without aeration. In about 40 hours after initiating the reaction, glucose was almost completely consumed. The glucose consumption rate was 2.50 g/L/h, the succinate production rate was 1.35 g/L/h, and the yield thereof was 78.4%. In contrast, when *Brevibacterium flavum* MJ233/PC/ΔLDH strain prepared in Example 4(c) was reacted in the same way as described above, the glucose consumption rate was 2.38 g/L/h, the succinate production rate was 1.21 g/L/h, and the yield thereof was 74.4%.

Example 12

Bacterial Cell Reaction

Sodium Carbonate Neutralization, Semi-Aerobic Reaction

A reaction suspension was prepared in the same way as Example 10 described above and the pH was kept at 7.6 with 2 M sodium carbonate, and a reaction was similarly conducted. In about 28 hours after initiating the reaction, glucose was almost completely consumed. The glucose consumption rate was 3.60 g/L/h, the succinate production rate was 2.27 g/L/h, and the yield thereof was 82.8%. In contrast, when *Brevibacterium flavum* MJ233/PC/ΔLDH strain prepared in Example 4(c) was reacted in the same way as described above, the glucose consumption rate was 2.97 g/L/h, the succinate production rate was 1.97 g/L/h, and the yield thereof was 88.0%.

Example 13

Bacterial Cell Reaction

Sodium Carbonate Neutralization, Anaerobic Reaction

A reaction suspension was prepared in the same way as Example 10 described above and the pH was kept at 7.6 with 2 M sodium carbonate, and a reaction was conducted with agitation at 200 rpm without aeration. In about 32 hours after initiating the reaction, glucose was almost completely consumed. The glucose consumption rate was 3.13 g/L/h, the succinate production rate was 1.80 g/L/h, and the yield thereof was 97.1%. In contrast, when *Brevibacterium flavum* MJ233/PC/ΔLDH strain prepared in Example 4(c) was reacted in the same way as described above, the glucose consumption rate was 2.70 g/L/h, the succinate production rate was 1.57 g/L/h, and the yield thereof was 88.6%.

TABLE 1

| Reaction condition | Analytical items | MJ233/PC/ΔLDH | MJ233/FRD/PC/ΔLDH |
|---|---|---|---|
| Example 10: Ammonium carbonate neutralization, semi-aerobic reaction | Glc consumption rate (g/L/hr) | 4.7 | 5.0 |
| | Succinate production rate (g/L/hr) | 2.1 | 2.7 |
| | Malate accumulation (g/L) | 7.9 | 2.4 |
| | Succinate yield (%) | 58.7 | 70.1 |
| Example 11: Ammonium carbonate neutralization, anaerobic reaction | Glc consumption rate | 2.4 | 2.5 |
| | Succinate production rate | 1.2 | 1.4 |
| | Malate accumulation | 2.9 | 0.6 |
| | Succinate yield | 74.4 | 78.4 |
| Example 12: Sodium carbonate neutralization, semi-aerobic reaction | Glc consumption rate | 3.0 | 3.6 |
| | Succinate production rate | 2.0 | 2.3 |
| | Malate accumulation | 0.0 | 0.0 |
| | Succinic acid yield | 88.0 | 82.8 |
| Example 13: Sodium carbonate neutralization, anaerobic reaction | Glc consumption rate | 2.7 | 3.1 |
| | Succinate production rate | 1.6 | 1.8 |
| | Malate accumulation | 0.5 | 0.0 |
| | Succinate yield | 88.6 | 97.1 |

Example 14

Bacterial Cell Reaction

Magnesium Carbonate Neutralization, Anaerobic Culture

*Brevibacterium flavum* MJ233/ΔLDH/pVK7 strain and MJ233/SDH/PC/ΔLDH strain were cultured for the succinate production as follows. The bacterial cells of the MJ233/ΔLDH/pVK7 strain and MJ233/SDH/PC/ΔLDH strain cultured on CM-Dex plate (containing 25 μg/ml kanamycin) were inoculated into 3 ml of seed culture medium (10 g/L glucose, 2.5 g/L $(NH_4)_2SO_4$, 0.5 g/L $KH_2PO_4$, 0.25 g/L $MgSO_4 \cdot 7H_2O$, 2 g/L urea, 0.01 g/L $FeSO_4 \cdot 7H_2O$, 0.01 g/L $MnSO_4 \cdot 7H_2O$, 50 μg/L biotin, 100 μg/L VB1.HCl, 15 mg/L protocatechuic acid, 0.02 mg/L $CuSO_4$, and 10 mg/L $CaCl_2$, with pH 7.0 (KOH)). Under an aerobic condition, these strains were cultured at 31.5° C. for about 15 hours with shaking.

Then, 3 ml of the main culture medium (100 g/L glucose, 5 g/L $(NH_4)_2SO_4$, 2 g/L $KH_2PO_4$, 3 g/L urea, 0.01 g/L $FeSO_4 \cdot 7H_2O$, 0.01 g/L $MnSO_4 \cdot 7H_2O$, 200 μg/L biotin, 200 μg/L VB1.HCl, and 71.4 g/L $MgCO_3$, each concentration is a final concentration after addition, pH 6.8 (NaOH)) was added, and the succinate production culture was carried out while the tube was sealed hermetically with a silicon cap for preventing aeration. The incubation was performed at 31.5° C. for about 48 hours and terminated before the disappearance of sugar in the medium.

After completion of the culture, the accumulation amounts of succinate and by-product malate and fumarate in the culture medium were analyzed by liquid chromatography after the culture medium had been suitably diluted. Two ShimpackSCR-102H (Simadzu) columns were connected in series and used as a column, and a sample was eluted at 40° C. using 5 mM p-toluene sulfonic acid. The eluate was neutralized using 20 mM Bis-Tris aqueous solution containing 5 mM p-toluene sulfonic acid and 100 μM EDTA. The succinate, malate and fumarate were measured by determining the electric conductivity with CDD-10AD (Simadzu). The results are shown in Table 2.

It was found that the yield of succinic acid of the MJ233/SDH/ΔLDH strain increased by about 4%, compared to the MJ233/ALDH/pVK7 strain obtained by introducing a vector plasmid in the same host. In addition, the accumulation of malate decreased by 3.6 g/L and the accumulation of fumarate decreased by 0.5 g/L.

TABLE 2

Production of succinate, malate, and fumarate by SDH-amplified strain

| Strains | OD620 (x51 dilution) | Glucose consumption (g/L) | Succinate yield (%) | Malate (g/L) | Fumarate (g/L) |
| --- | --- | --- | --- | --- | --- |
| MJ233/ΔLDH/pVK7 | 0.258 | 66.1 | 55.8 | 6.4 | 1.6 |
| MJ233/SDH/ΔLDH | 0.370 | 82.1 | 60.2 | 2.8 | 1.1 |

(B) Culture Evaluation of the Strain in which SDH and PC are Simultaneously Amplified

*Brevibacterium flavum* MJ233/PC/ΔLDH strain and MJ233/SDH/PC/ΔLDH strain were cultured for succinate production as follows. The bacterial cells of the MJ233/PC/ΔLDH strain and MJ233/SDH/PC/ΔLDH strain cultured on CM-Dex plate were inoculated in 3 ml of the culture medium A (20 g/L glucose, 14 g/L $(NH_4)_2SO_4$, 0.5 g/L $KH_2PO_4$, 0.5 g/L $KH_2PO_4$, 0.5 g/L $MgSO_4.7H_2O$, 4 g/L urea, 0.02 g/L $FeSO_4.7H_2O$, 0.02 g/L $MnSO_4.7H_2O$, 200 μg/L biotin, 200 μg/L VB1.HCl, 1 g/L casamino acid, and 1 g/L yeast extract). Under aerobic condition, these strains were incubated at 31.5° C. for about 15 hours while shaking in a tube.

After that, 3 mL of main solution (200 g/L glucose, 30 g/L sodium sulfite, and 142.8 g/L $MgCO_3$) was added, and the succinate production culture was carried out while the tube was sealed hermetically with a silicon cap for preventing aeration. The incubation was performed at 31.5° C. for about 48 hours and terminated before the disappearance of sugar in the medium.

After completion of the culture, the accumulation amounts of succinate and by-product malate and fumarate in the culture medium were analyzed by liquid chromatography after the culture medium had been suitably diluted. Two Shim-packSCR-102H (Simadzu) columns were connected in series and used as a column, and a sample was eluted at 40° C. with 5 mM p-toluene sulfonic acid. The eluate was neutralized with 20 mM Bis-Tris aqueous solution containing 5 mM p-toluene sulfonic acid and 100 μM EDTA. The succinate and by-product malate and fumarate were measured by determining the electric conductivity with CDD-10AD (Simadzu). The results are shown in Table 3.

TABLE 3

Production of succinate, malate, and fumarate by the strain in which a combination of SDH and PC are amplified

| Strains | OD620 (x51 dilution) | Glucose consumption (g/L) | Succinate yield (%) | Malate (g/L) | Fumarate (g/L) |
| --- | --- | --- | --- | --- | --- |
| MJ233/PC/ΔLDH | 0.521 | 94.3 | 60.6 | 6.5 | 0.8 |
| MJ233/SDH/PC/ΔLDH | 0.451 | 89.8 | 63.4 | 3.6 | 0.6 |

In the MJ233/SDH/PC/ΔLDH strain, the yield of succinate increased by about 3% as compared to the MJ233/PC/ΔLDH strain in which only PC is enhanced, whereas the accumulation of malate decreased by 3.2 g/L, and the accumulation of fumarate decreased by 0.2 g/L.

In consideration of such results and the results of the above section (A), it was found that the amplification of SDH gene can be effective in increasing the yield of succinate as well as in lowering the amount of malate and fumarate as by-products upon production of succinate.

INDUSTRIAL APPLICABILITY

According to the production method of the present invention, succinic acid can be produced rapidly at high efficiency. The produced succinic acid can be used as food additives, drugs, cosmetics, and so on. In addition, a polymer comprising succinic acid can be produced by carrying out a polymerization reaction using the produced succinic acid as a raw material.

The invention claimed is:

1. A method for producing succinic acid by fermentation, comprising allowing a bacterium selected from coryneform bacterium, *Bacillus* bacterium, and *Rhizobium* bacterium or a cell preparation thereof to react with an organic raw material in a reaction solution containing a carbonate ion, a bicarbonate ion, or carbon dioxide gas under anaerobic conditions to generate succinic acid; and collecting the succinic acid, wherein said bacterium is modified by:
   having a succinate dehydrogenase gene from coryneform bacterium operably linked to a strong heterologous promoter, or
   increasing copy number of a succinate dehydrogenase gene from coryneform bacterium,
   wherein said succinate dehydrogenase gene comprises a nucleotide sequence having not less than 99% sequence identity to nucleotides 1153-3171 of SEQ ID NO: 28, a nucleotide sequence having not less than 99% sequence identity to nucleotides 3174-3920 of SEQ ID NO: 28, and a nucleotide sequence having not less than 99% sequence identity to nucleotides 363-1133 of SEQ ID NO: 28.

2. The method according to claim 1, wherein the bacterium is further modified to have a disrupted endogenous lactate dehygrogenase gene.

3. The method according to claim 1, wherein the bacterium is further modified by transformation with a plasmid containing a pyruvate carboxylase gene from coryneform bacterium, or by introducing or amplifying a pyruvate carboxylase gene from coryneform bacterium.

4. The method according to claim 1, wherein the organic raw material is glucose.

5. A method for producing a polymer containing succinic acid, comprising producing succinic acid by the method according to claim 1, and polymerizing the obtained succinic acid.

* * * * *

SEQUENCE LISTING

```
<160> NUMBER OF SEQ ID NOS: 31

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctttttaac ccatcacata tacctgccgt tcac                              34

<210> SEQ ID NO 2
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaaggttagg aatacggtta gccatttgcc tg                                   32

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaggtctgcc tcgtgaagaa g                                               21

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcattagaa aaactcatcg agcatca                                         27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgatgaaaga aaccgtcggc                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgtcagaaga actgcttctg                                                 20

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agttgcatac gcatacgcac tga                                             23

<210> SEQ ID NO 8
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagactggga ctgcaacgtc ttg                                            23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatctttcag ctgctcacac gtga                                           24

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatcttaggt cactaaaact aattcag                                        27

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatccaggag gcattaatta agcggccgcg ggccctgca                           39

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggcccgcgg ccgcttaatt aatgcctcct g                                   31

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
accttaatta atgtcgactc acacatcttc aacgcttcca gca                      43

<210> SEQ ID NO 14
<211> LENGTH: 44
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 14
gttgggccca ggtttaggaa acgacgacga tcaagtcgcc acct                            44

<210> SEQ ID NO 15
<211> LENGTH: 3423
<212> TYPE: DNA
<213> ORGANISM: Brevibacterium flavum
<220> FEATURE:
<221> NAME/KEY: CDS
<222> LOCATION: (1)..(3420)

<400> SEQUENCE: 15 atg tcg act cac aca tct tca acg ctt cca gca ttc aaa aag atc ttg            48
Met Ser Thr His Thr Ser Ser Thr Leu Pro Ala Phe Lys Lys Ile Leu
 1               5                  10                  15 gta gca aac cgc ggc gaa atc gcg gtc cgt gct ttc cgt gca gca ctc            96
Val Ala Asn Arg Gly Glu Ile Ala Val Arg Ala Phe Arg Ala Ala Leu
             20                  25                  30 gaa acc ggt gca gcc acg gta gct att tac ccc cgt gaa gat cgg gga           144
Glu Thr Gly Ala Ala Thr Val Ala Ile Tyr Pro Arg Glu Asp Arg Gly
         35                  40                  45 tca ttc cac cgc tct ttt gct tct gaa gct gtc cgc att ggt act gaa           192
Ser Phe His Arg Ser Phe Ala Ser Glu Ala Val Arg Ile Gly Thr Glu
     50                  55                  60 ggc tca cca gtc aag gcg tac ctg gac atc gat gaa att atc ggt gca           240
Gly Ser Pro Val Lys Ala Tyr Leu Asp Ile Asp Glu Ile Ile Gly Ala
 65                  70                  75                  80 gct aaa aaa gtt aaa gca gat gct att tac ccg gga tat ggc ttc ctg           288
Ala Lys Lys Val Lys Ala Asp Ala Ile Tyr Pro Gly Tyr Gly Phe Leu
                 85                  90                  95 tct gaa aat gcc cag ctt gcc cgc gag tgc gcg gaa aac ggc att act           336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct           384
Phe Ile Gly Pro Thr Pro Glu Val Leu Asp Leu Thr Gly Asp Lys Ser
        115                 120                 125 cgt gcg gta acc gcc gcg aag aag gct ggt ctg cca gtt ttg gcg gaa           432
Arg Ala Val Thr Ala Ala Lys Lys Ala Gly Leu Pro Val Leu Ala Glu
    130                 135                 140 tcc acc ccg agc aaa aac atc gat gac atc gtt aaa agc gct gaa ggc           480
Ser Thr Pro Ser Lys Asn Ile Asp Asp Ile Val Lys Ser Ala Glu Gly
145                 150                 155                 160 cag act tac ccc atc ttt gta aag gca gtt gcc ggt ggt gga cgc               528
Gln Thr Tyr Pro Ile Phe Val Lys Ala Val Ala Gly Gly Gly Gly Arg
                165                 170                 175 ggt atg cgc ttt gtt tct tca cct gat gag ctt cgc aaa ttg gca aca           576
Gly Met Arg Phe Val Ser Ser Pro Asp Glu Leu Arg Lys Leu Ala Thr
            180                 185                 190 gaa gca tct cgt gaa gct gaa gcg gca ttc ggc gac ggt tcg gta tat           624
Glu Ala Ser Arg Glu Ala Glu Ala Ala Phe Gly Asp Gly Ser Val Tyr
        195                 200                 205 gtc gag cgt gct gtg att aac ccc cag cac att gaa gtg cag atc ctt           672
Val Glu Arg Ala Val Ile Asn Pro Gln His Ile Glu Val Gln Ile Leu
    210                 215                 220 ggc gat cgc act gga gaa gtt gta cac ctt tat gaa cgt gac tgc tca           720
Gly Asp Arg Thr Gly Glu Val Val His Leu Tyr Glu Arg Asp Cys Ser
225                 230                 235                 240
```

```
ctg cag cgt cgt cac caa aaa gtt gtc gaa att gcg cca gca cag cat      768
Leu Gln Arg Arg His Gln Lys Val Val Glu Ile Ala Pro Ala Gln His
                245                 250                 255 ttg gat cca gaa ctg cgt gat cgc att tgt gcg gat gca gta aag ttc      816
Leu Asp Pro Glu Leu Arg Asp Arg Ile Cys Ala Asp Ala Val Lys Phe
            260                 265                 270 tgc cgc tcc att ggt tac cag ggc gcg gga act gtg gaa ttc ttg gtc      864
Cys Arg Ser Ile Gly Tyr Gln Gly Ala Gly Thr Val Glu Phe Leu Val
        275                 280                 285 gat gaa aag ggc aac cac gtt ttc atc gaa atg aac cca cgt atc cag      912
Asp Glu Lys Gly Asn His Val Phe Ile Glu Met Asn Pro Arg Ile Gln
    290                 295                 300 gtt gag cac acc gtg act gaa gaa gtc acc gag gtg gac ctg gtg aag      960
Val Glu His Thr Val Thr Glu Glu Val Thr Glu Val Asp Leu Val Lys
305                 310                 315                 320 gcg cag atg cgc ttg gct gct ggt gca acc ttg aag gaa ttg ggt ctg     1008
Ala Gln Met Arg Leu Ala Ala Gly Ala Thr Leu Lys Glu Leu Gly Leu
                325                 330                 335 acc caa gat aag atc aag acc cac ggt gcg gca ctg cag tgc cgc atc     1056
Thr Gln Asp Lys Ile Lys Thr His Gly Ala Ala Leu Gln Cys Arg Ile
            340                 345                 350 acc acg gaa gat cca aac aac ggc ttc cgc cca gat acc gga act atc     1104
Thr Thr Glu Asp Pro Asn Asn Gly Phe Arg Pro Asp Thr Gly Thr Ile
        355                 360                 365 acc gcg tac cgc tca cca ggc gga gct ggc gtt cgt ctt gac ggt gca     1152
Thr Ala Tyr Arg Ser Pro Gly Gly Ala Gly Val Arg Leu Asp Gly Ala
    370                 375                 380 gct cag ctc ggt ggc gaa atc acc gca cac ttt gac tcc atg ctg gtg     1200
Ala Gln Leu Gly Gly Glu Ile Thr Ala His Phe Asp Ser Met Leu Val
385                 390                 395                 400 aaa atg acc tgc cgt ggt tcc gat ttt gaa act gct gtt gct cgt gca     1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att     1296
Gln Arg Ala Leu Ala Glu Phe Thr Val Ser Gly Val Ala Thr Asn Ile
            420                 425                 430 ggt ttc ttg cgt gcg ttg ctg cgt gaa gag gac ttt act tcc aag cgc     1344
Gly Phe Leu Arg Ala Leu Leu Arg Glu Glu Asp Phe Thr Ser Lys Arg
        435                 440                 445 atc gcc acc gga ttt atc ggc gat cac cca cac ctc ctt cag gct cca     1392
Ile Ala Thr Gly Phe Ile Gly Asp His Pro His Leu Leu Gln Ala Pro
    450                 455                 460 cct gcg gat gat gag cag gga cgc atc ctg gat tac ttg gca gat gtc     1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gca cca     1488
Thr Val Asn Lys Pro His Gly Val Arg Pro Lys Asp Val Ala Ala Pro
                485                 490                 495 atc gat aag ctg ccc aac atc aag gat ctg cca ctg cca cgc ggt tcc     1536
Ile Asp Lys Leu Pro Asn Ile Lys Asp Leu Pro Leu Pro Arg Gly Ser
            500                 505                 510 cgt gac cgc ctg aag cag ctt gga cca gca gcg ttt gcc cgc gat ctc     1584
Arg Asp Arg Leu Lys Gln Leu Gly Pro Ala Ala Phe Ala Arg Asp Leu
        515                 520                 525 cgt gag cag gac gca ctg gca gtt act gat acc acc ttc cgc gat gca     1632
Arg Glu Gln Asp Ala Leu Ala Val Thr Asp Thr Thr Phe Arg Asp Ala
    530                 535                 540 cac cag tct ttg ctt gcg acc cga gtc cgc tca ttc gca ctg aag cct     1680
His Gln Ser Leu Leu Ala Thr Arg Val Arg Ser Phe Ala Leu Lys Pro
```

```
                     545                 550                 555                 560
gcg gca gag gcc gtc gca aag ctg act cct gag ctt ttg tcc gtg gag       1728
Ala Ala Glu Ala Val Ala Lys Leu Thr Pro Glu Leu Leu Ser Val Glu
                565                 570                 575 gcc tgg ggc ggt gcg acc tac gat gtg gcg atg cgt ttc ctc ttt gag       1776
Ala Trp Gly Gly Ala Thr Tyr Asp Val Ala Met Arg Phe Leu Phe Glu
        580                 585                 590 gat ccg tgg gac agg ctc gac gag ctg cgc gag gcg atg ccg aat gtg       1824
Asp Pro Trp Asp Arg Leu Asp Glu Leu Arg Glu Ala Met Pro Asn Val
                595                 600                 605 aac att cag atg ctg ctt cgc ggc cgc aac acc gtg gga tac acc cca       1872
Asn Ile Gln Met Leu Leu Arg Gly Arg Asn Thr Val Gly Tyr Thr Pro
        610                 615                 620 tac cca gac tcc gtc tgt cgc gcg ttt gtt aag gaa gct gcc acc tcc       1920
Tyr Pro Asp Ser Val Cys Arg Ala Phe Val Lys Glu Ala Ala Thr Ser
625                 630                 635                 640 ggc gtg gac atc ttc cgc atc ttc gac gcg ctt aac gac gtc tcc cag       1968
Gly Val Asp Ile Phe Arg Ile Phe Asp Ala Leu Asn Asp Val Ser Gln
                645                 650                 655 atg cgt cca gca atc gac gca gtc ctg gag acc aac acc gcg gtc gct       2016
Met Arg Pro Ala Ile Asp Ala Val Leu Glu Thr Asn Thr Ala Val Ala
        660                 665                 670 gaa gtg gct atg gct tat tct ggt gat ctt tcc gat ccg aat gaa aag       2064
Glu Val Ala Met Ala Tyr Ser Gly Asp Leu Ser Asp Pro Asn Glu Lys
                675                 680                 685 ctc tac acc ctg gat tac tac ctg aag atg gca gag gag atc gtc aag       2112
Leu Tyr Thr Leu Asp Tyr Tyr Leu Lys Met Ala Glu Glu Ile Val Lys
        690                 695                 700 tct ggc gct cac att ctg gct att aag gat atg gct ggt ctg ctt cgc       2160
Ser Gly Ala His Ile Leu Ala Ile Lys Asp Met Ala Gly Leu Leu Arg
705                 710                 715                 720 cca gct gca gcc acc aag ctg gtc acc gca ctg cgc cgt gaa ttt gat       2208
Pro Ala Ala Ala Thr Lys Leu Val Thr Ala Leu Arg Arg Glu Phe Asp
                725                 730                 735 ctg cca gtg cac gtg cac acc cac gac act gcg ggt ggc cag ctg gca       2256
Leu Pro Val His Val His Thr His Asp Thr Ala Gly Gly Gln Leu Ala
        740                 745                 750 acc tac ttt gct gca gct caa gct ggt gca gat gct gtt gac ggt gct       2304
Thr Tyr Phe Ala Ala Ala Gln Ala Gly Ala Asp Ala Val Asp Gly Ala
                755                 760                 765 tcc gca cca ctg tct ggc acc acc tcc cag cca tcc ctg tct gcc att       2352
Ser Ala Pro Leu Ser Gly Thr Thr Ser Gln Pro Ser Leu Ser Ala Ile
        770                 775                 780 gtt gct gca ttc gcg cac acc cgt cgc gat acc ggt ttg agc ctc gag       2400
Val Ala Ala Phe Ala His Thr Arg Arg Asp Thr Gly Leu Ser Leu Glu
785                 790                 795                 800 gct gtt tct gac ctc gag cca tac tgg gaa gca gtg cgc gga ctg tac       2448
Ala Val Ser Asp Leu Glu Pro Tyr Trp Glu Ala Val Arg Gly Leu Tyr
                805                 810                 815 ctg cca ttt gag tct gga acc cca ggc cca acc ggt cgc gtc tac cgc       2496
Leu Pro Phe Glu Ser Gly Thr Pro Gly Pro Thr Gly Arg Val Tyr Arg
        820                 825                 830 cac gaa atc cca ggc gga cag ctg tcc aac ctg cgt gca cag gcc acc       2544
His Glu Ile Pro Gly Gly Gln Leu Ser Asn Leu Arg Ala Gln Ala Thr
                835                 840                 845 gca ctg ggc ctt gcg gat cgt ttc gaa ctc atc gaa gac aac tac gcg       2592
Ala Leu Gly Leu Ala Asp Arg Phe Glu Leu Ile Glu Asp Asn Tyr Ala
        850                 855                 860 gca gtt aat gag atg ctg gga cgc cca acc aag gtc acc cca tcc tcc       2640
```

```
                Ala Val Asn Glu Met Leu Gly Arg Pro Thr Lys Val Thr Pro Ser Ser
                865                 870                 875                 880 aag gtt gtt ggc gac ctc gca ctc cac ctc gtt ggt gcg ggt gtg gat              2688
Lys Val Val Gly Asp Leu Ala Leu His Leu Val Gly Ala Gly Val Asp
                        885                 890                 895 cca gca gac ttt gct gca gat cca caa aag tac gac atc cca gac tct              2736
Pro Ala Asp Phe Ala Ala Asp Pro Gln Lys Tyr Asp Ile Pro Asp Ser
            900                 905                 910 gtc atc gcg ttc ctg cgc ggc gag ctt ggt aac cct cca ggt ggc tgg              2784
Val Ile Ala Phe Leu Arg Gly Glu Leu Gly Asn Pro Pro Gly Gly Trp
        915                 920                 925 cca gag cca ctg cgc acc cgc gca ctg gaa ggc cgc tcc gaa ggc aag              2832
Pro Glu Pro Leu Arg Thr Arg Ala Leu Glu Gly Arg Ser Glu Gly Lys
    930                 935                 940 gca cct ctg acg gaa gtt cct gag gaa gag cag gcg cac ctc gac gct              2880
Ala Pro Leu Thr Glu Val Pro Glu Glu Glu Gln Ala His Leu Asp Ala
945                 950                 955                 960 gat gat tcc aag gaa cgt cgc aac agc ctc aac cgc ctg ctg ttc ccg              2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc              2976
Lys Pro Thr Glu Glu Phe Leu Glu His Arg Arg Arg Phe Gly Asn Thr
            980                 985                 990 tct gcg ctg gat gat cgt gaa ttc ttc tac ggc ctg gtc gaa ggc cgc              3024
Ser Ala Leu Asp Asp Arg Glu Phe Phe Tyr Gly Leu Val Glu Gly Arg
        995                 1000                1005 gag act ttg atc cgc ctg cca gat gtg cgc acc cca ctg ctt gtt cgc              3072
Glu Thr Leu Ile Arg Leu Pro Asp Val Arg Thr Pro Leu Leu Val Arg
    1010                1015                1020 ctg gat gcg atc tcc gag cca gac gat aag ggt atg cgc aat gtt gtg              3120
Leu Asp Ala Ile Ser Glu Pro Asp Asp Lys Gly Met Arg Asn Val Val
1025                1030                1035                1040 gcc aac gtc aac ggc cag atc cgc cca atg cgt gtg cgt gac cgc tcc              3168
Ala Asn Val Asn Gly Gln Ile Arg Pro Met Arg Val Arg Asp Arg Ser
                1045                1050                1055 gtt gag tct gtc acc gca acc gca gaa aag gca gat tcc tcc aac aag              3216
Val Glu Ser Val Thr Ala Thr Ala Glu Lys Ala Asp Ser Ser Asn Lys
            1060                1065                1070 ggc cat gtt gct gca cca ttc gct ggt gtt gtc act gtg act gtt gct              3264
Gly His Val Ala Ala Pro Phe Ala Gly Val Val Thr Val Thr Val Ala
        1075                1080                1085 gaa ggt gat gag gtc aag gct gga gat gca gtc gca atc atc gag gct              3312
Glu Gly Asp Glu Val Lys Ala Gly Asp Ala Val Ala Ile Ile Glu Ala
    1090                1095                1100 atg aag atg gaa gca aca atc act gct tct gtt gac ggc aaa atc gat              3360
Met Lys Met Glu Ala Thr Ile Thr Ala Ser Val Asp Gly Lys Ile Asp
1105                1110                1115                1120 cgc gtt gtg gtt cct gct gca acg aag gtg gaa ggt ggc gac ttg atc              3408
Arg Val Val Val Pro Ala Ala Thr Lys Val Glu Gly Gly Asp Leu Ile
                1125                1130                1135 gtc gtc gtt tcc taa                                                          3423
Val Val Val Ser
        1140

<210> SEQ ID NO 16
<211> LENGTH: 1140
<212> TYPE: PRT
<213> ORGANISM: Brevibacterium flavum

<400> SEQUENCE: 16
```

-continued

```
Met Ser Thr His Thr Ser Ser Thr Leu Pro Ala Phe Lys Lys Ile Leu
 1               5                  10                  15

Val Ala Asn Arg Gly Glu Ile Ala Val Arg Ala Phe Arg Ala Ala Leu
                 20                  25                  30

Glu Thr Gly Ala Ala Thr Val Ala Ile Tyr Pro Arg Glu Asp Arg Gly
             35                  40                  45

Ser Phe His Arg Ser Phe Ala Ser Glu Ala Val Arg Ile Gly Thr Glu
         50                  55                  60

Gly Ser Pro Val Lys Ala Tyr Leu Asp Ile Asp Glu Ile Ile Gly Ala
 65                  70                  75                  80

Ala Lys Lys Val Lys Ala Asp Ala Ile Tyr Pro Gly Tyr Gly Phe Leu
                 85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ser Ser Pro Asp Glu Leu Arg Lys Leu Ala Thr
            180                 185                 190

Glu Ala Ser Arg Glu Ala Glu Ala Ala Phe Gly Asp Gly Ser Val Tyr
        195                 200                 205

Val Glu Arg Ala Val Ile Asn Pro Gln His Ile Glu Val Gln Ile Leu
    210                 215                 220

Gly Asp Arg Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
```

-continued

```
                420                 425                 430
Gly Phe Leu Arg Ala Leu Leu Arg Glu Glu Asp Phe Thr Ser Lys Arg
            435                 440                 445
Ile Ala Thr Gly Phe Ile Gly Asp His Pro His Leu Leu Gln Ala Pro
        450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
        515                 520                 525
Arg Glu Gln Asp Ala Leu Ala Val Thr Asp Thr Phe Arg Asp Ala
    530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
        595                 600                 605
Asn Ile Gln Met Leu Leu Arg Gly Arg Asn Thr Val Gly Tyr Thr Pro
    610                 615                 620
Tyr Pro Asp Ser Val Cys Arg Ala Phe Val Lys Glu Ala Ala Thr Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
        675                 680                 685
Leu Tyr Thr Leu Asp Tyr Tyr Leu Lys Met Ala Glu Glu Ile Val Lys
    690                 695                 700
Ser Gly Ala His Ile Leu Ala Ile Lys Asp Met Ala Gly Leu Leu Arg
705                 710                 715                 720
Pro Ala Ala Ala Thr Lys Leu Val Thr Ala Leu Arg Arg Glu Phe Asp
                725                 730                 735
Leu Pro Val His Val His Thr His Asp Thr Ala Gly Gly Gln Leu Ala
            740                 745                 750
Thr Tyr Phe Ala Ala Ala Gln Ala Gly Ala Asp Ala Val Asp Gly Ala
        755                 760                 765
Ser Ala Pro Leu Ser Gly Thr Thr Ser Gln Pro Ser Leu Ser Ala Ile
    770                 775                 780
Val Ala Ala Phe Ala His Thr Arg Arg Asp Thr Gly Leu Ser Leu Glu
785                 790                 795                 800
Ala Val Ser Asp Leu Glu Pro Tyr Trp Glu Ala Val Arg Gly Leu Tyr
                805                 810                 815
Leu Pro Phe Glu Ser Gly Thr Pro Gly Pro Thr Gly Arg Val Tyr Arg
            820                 825                 830
His Glu Ile Pro Gly Gly Gln Leu Ser Asn Leu Arg Ala Gln Ala Thr
        835                 840                 845
```

-continued

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val Arg
    1010                1015                1020

Leu Asp Ala Ile Ser Glu Pro Asp Asp Lys Gly Met Arg Asn Val Val
1025                1030                1035                1040

Ala Asn Val Asn Gly Gln Ile Arg Pro Met Arg Val Arg Asp Arg Ser
                1045                1050                1055

Val Glu Ser Val Thr Ala Thr Ala Glu Lys Ala Asp Ser Ser Asn Lys
            1060                1065                1070

Gly His Val Ala Ala Pro Phe Ala Gly Val Val Thr Val Thr Val Ala
        1075                1080                1085

Glu Gly Asp Glu Val Lys Ala Gly Asp Ala Val Ala Ile Ile Glu Ala
    1090                1095                1100

Met Lys Met Glu Ala Thr Ile Thr Ala Ser Val Asp Gly Lys Ile Asp
1105                1110                1115                1120

Arg Val Val Val Pro Ala Ala Thr Lys Val Glu Gly Gly Asp Leu Ile
                1125                1130                1135

Val Val Val Ser
        1140

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccacctgcag gactccacga tcggcaaaga aacga                                35

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 18
ggtatttaaa aaggcgcaga gcgtcgtttt gaacatagg                     39

<210> SEQ ID NO 19
<211> LENGTH: 3847
<212> TYPE: DNA
<213> ORGANISM: Escherichia coli
<220> FEATURE:
<221> NAME/KEY: CDS
<222> LOCATION: (440)..(2239)
<220> FEATURE:
<221> NAME/KEY: CDS
<222> LOCATION: (2241)..(2972)
<220> FEATURE:
<221> NAME/KEY: CDS
<222> LOCATION: (2986)..(3378)
<220> FEATURE:
<221> NAME/KEY: CDS
<222> LOCATION: (3392)..(3748)

<400> SEQUENCE: 19

```
ccacctgcag gactccacga tcggcaaaga aacgacggat ctccgccata atcgccgcgc      60
gttttaataa gttaggaatg gatgcgctcg gctgccagga tgccgtttcg ctcatagtta     120
aatctccagt ttttgacaag ggcacgaagt ctactcgcaa cgcgacggcg agacaaattt     180
tacgcaggaa tcaaacagcg gtgggcagtg actaaaaaaa gcacgatctg atggtttagt     240
aattaaatta atcatcttca gtgataattt agccctcttg cgcactaaaa aaatcgatct     300
cgtcaaattt cagacttatc catcagacta tactgttgta cctataaagg agcagtggaa     360
tagcgttcgc agaccgtaac tttcaggtac ttaccctgaa gtacgtggct gtgggataaa     420
aacaatctgg aggaatgtc gtg caa acc ttt caa gcc gat ctt gcc att gta    472
                         Val Gln Thr Phe Gln Ala Asp Leu Ala Ile Val
                          1               5                  10 ggc gcc ggt ggc gcg gga tta cgt gct gca att gct gcc gcg cag gca     520
Gly Ala Gly Gly Ala Gly Leu Arg Ala Ala Ile Ala Ala Ala Gln Ala
             15                  20                  25 aat ccg aat gca aaa atc gca cta atc tca aaa gta tac ccg atg cgt     568
Asn Pro Asn Ala Lys Ile Ala Leu Ile Ser Lys Val Tyr Pro Met Arg
         30                  35                  40 agc cat acc gtt gct gca gaa ggg ggc tcc gcc gct gtc gcg cag gat     616
Ser His Thr Val Ala Ala Glu Gly Gly Ser Ala Ala Val Ala Gln Asp
     45                  50                  55 cat gac agc ttc gaa tat cac ttt cac gat aca gta gcg ggt ggc gac     664
His Asp Ser Phe Glu Tyr His Phe His Asp Thr Val Ala Gly Gly Asp
 60                  65                  70                  75 tgg ttg tgt gag cag gat gtc gtg gat tat ttc gtc cac cac tgc cca     712
Trp Leu Cys Glu Gln Asp Val Val Asp Tyr Phe Val His His Cys Pro
                 80                  85                  90 acc gaa atg acc caa ctg gaa ctg tgg gga tgc cca tgg agc cgt cgc     760
Thr Glu Met Thr Gln Leu Glu Leu Trp Gly Cys Pro Trp Ser Arg Arg
             95                 100                 105 ccg gat ggt agc gtc aac gta cgt cgc ttc ggc ggc atg aaa atc gag     808
Pro Asp Gly Ser Val Asn Val Arg Arg Phe Gly Gly Met Lys Ile Glu
         110                 115                 120 cgc acc tgg ttc gcc gcc gat aag acc ggc ttc cat atg ctg cac acg     856
Arg Thr Trp Phe Ala Ala Asp Lys Thr Gly Phe His Met Leu His Thr
     125                 130                 135 ctg ttc cag acc tct ctg caa ttc ccg cag atc cag cgt ttt gac gaa     904
Leu Phe Gln Thr Ser Leu Gln Phe Pro Gln Ile Gln Arg Phe Asp Glu
140                 145                 150                 155
```

```
cat ttc gtg ctg gat att ctg gtt gat gat ggt cat gtt cgc ggc ctg        952
His Phe Val Leu Asp Ile Leu Val Asp Asp Gly His Val Arg Gly Leu
              160                 165                 170 gta gca atg aac atg atg gaa ggc acg ctg gtg cag atc cgt gct aac       1000
Val Ala Met Asn Met Met Glu Gly Thr Leu Val Gln Ile Arg Ala Asn
          175                 180                 185 gcg gtc gtt atg gct act ggc ggt gcg ggt cgc gtt tat cgt tac aac       1048
Ala Val Val Met Ala Thr Gly Gly Ala Gly Arg Val Tyr Arg Tyr Asn
      190                 195                 200 acc aac ggc ggc atc gtt acc ggt gac ggt atg ggt atg gcg cta agc       1096
Thr Asn Gly Gly Ile Val Thr Gly Asp Gly Met Gly Met Ala Leu Ser
  205                 210                 215 cac ggc gtt ccg ctg cgt gac atg gaa ttc gtt cag tat cac cca acc       1144
His Gly Val Pro Leu Arg Asp Met Glu Phe Val Gln Tyr His Pro Thr
220                 225                 230                 235 ggt ctg cca ggt tcc ggt atc ctg atg acc gaa ggt tgc cgc ggt gaa       1192
Gly Leu Pro Gly Ser Gly Ile Leu Met Thr Glu Gly Cys Arg Gly Glu
              240                 245                 250 ggc ggt att ctg gtc aac aaa aat ggc tac cgt tat ctg caa gat tac       1240
Gly Gly Ile Leu Val Asn Lys Asn Gly Tyr Arg Tyr Leu Gln Asp Tyr
          255                 260                 265 ggc atg ggc ccg gaa act ccg ctg ggc gag ccg aaa aac aaa tat atg       1288
Gly Met Gly Pro Glu Thr Pro Leu Gly Glu Pro Lys Asn Lys Tyr Met
      270                 275                 280 gaa ctg ggt cca cgc gac aaa gtc tct cag gcc ttc tgg cac gaa tgg       1336
Glu Leu Gly Pro Arg Asp Lys Val Ser Gln Ala Phe Trp His Glu Trp
  285                 290                 295 cgt aaa ggc aac acc atc tcc acg ccg cgt ggc gat gtg gtt tat ctc       1384
Arg Lys Gly Asn Thr Ile Ser Thr Pro Arg Gly Asp Val Val Tyr Leu
300                 305                 310                 315 gac ttg cgt cac ctc ggc gag aaa aaa ctg cat gaa cgt ctg ccg ttc       1432
Asp Leu Arg His Leu Gly Glu Lys Lys Leu His Glu Arg Leu Pro Phe
              320                 325                 330 atc tgc gaa ctg gcg aaa gcg tac gtt ggc gtc gat ccg gtt aaa gaa       1480
Ile Cys Glu Leu Ala Lys Ala Tyr Val Gly Val Asp Pro Val Lys Glu
          335                 340                 345 ccg att ccg gta cgt ccg acc gca cac tac acc atg ggc ggt atc gaa       1528
Pro Ile Pro Val Arg Pro Thr Ala His Tyr Thr Met Gly Gly Ile Glu
      350                 355                 360 acc gat cag aac tgt gaa acc cgc att aaa ggt ctg ttc gcc gtg ggt       1576
Thr Asp Gln Asn Cys Glu Thr Arg Ile Lys Gly Leu Phe Ala Val Gly
  365                 370                 375 gaa tgt tcc tct gtt ggt ctg cac ggt gca aac cgt ctg ggt tct aac       1624
Glu Cys Ser Ser Val Gly Leu His Gly Ala Asn Arg Leu Gly Ser Asn
380                 385                 390                 395 tcc ctg gcg gaa ctg gtg gtc ttc ggc cgt ctg gcc ggt gaa caa gcg       1672
Ser Leu Ala Glu Leu Val Val Phe Gly Arg Leu Ala Gly Glu Gln Ala
              400                 405                 410 aca gag cgt gca gca act gcc ggt aat ggc aac gaa gcg gca att gaa       1720
Thr Glu Arg Ala Ala Thr Ala Gly Asn Gly Asn Glu Ala Ala Ile Glu
          415                 420                 425 gcg cag gca gct ggc gtt gaa caa cgt ctg aaa gat ctg gtt aac cag       1768
Ala Gln Ala Ala Gly Val Glu Gln Arg Leu Lys Asp Leu Val Asn Gln
      430                 435                 440 gat ggc ggc gaa aac tgg gcg aag atc cgc gac gaa atg ggc ctg gct       1816
Asp Gly Gly Glu Asn Trp Ala Lys Ile Arg Asp Glu Met Gly Leu Ala
  445                 450                 455 atg gaa gaa ggc tgc ggt atc tac cgt acg ccg gaa ctg atg cag aaa       1864
Met Glu Glu Gly Cys Gly Ile Tyr Arg Thr Pro Glu Leu Met Gln Lys
460                 465                 470                 475
```

```
                                                   -continued acc atc gac aag ctg gca gag ctg cag gaa cgc ttc aag cgc gtg cgc      1912
Thr Ile Asp Lys Leu Ala Glu Leu Gln Glu Arg Phe Lys Arg Val Arg
                480                 485                 490 atc acc gac act tcc agc gtg ttc aac acc gac ctg ctc tac acc att      1960
Ile Thr Asp Thr Ser Ser Val Phe Asn Thr Asp Leu Leu Tyr Thr Ile
        495                 500                 505 gaa ctg ggc cac ggt ctg aac gtt gct gaa tgt atg gcg cac tcc gca      2008
Glu Leu Gly His Gly Leu Asn Val Ala Glu Cys Met Ala His Ser Ala
            510                 515                 520 atg gca cgt aaa gag tcc cgc ggc gcg cac cag cgt ctg gac gaa ggt      2056
Met Ala Arg Lys Glu Ser Arg Gly Ala His Gln Arg Leu Asp Glu Gly
        525                 530                 535 tgc acc gag cgt gac gac gtc aac ttc ctc aaa cac acc ctc gcc ttc      2104
Cys Thr Glu Arg Asp Asp Val Asn Phe Leu Lys His Thr Leu Ala Phe
540                 545                 550                 555 cgc gat gct gat ggc acg act cgc ctg gag tac agc gac gtg aag att      2152
Arg Asp Ala Asp Gly Thr Thr Arg Leu Glu Tyr Ser Asp Val Lys Ile
                560                 565                 570 act acg ctg ccg cca gct aaa cgc gtt tac ggt ggc gaa gcg gat gca      2200
Thr Thr Leu Pro Pro Ala Lys Arg Val Tyr Gly Gly Glu Ala Asp Ala
            575                 580                 585 gcc gat aag gcg gaa gca gcc aat aag aag gag aag gcg a   atg gct gag  2249
Ala Asp Lys Ala Glu Ala Ala Asn Lys Lys Glu Lys Ala     Met Ala Glu
                590                 595                 600 atg aaa aac ctg aaa att gag gtg gtg cgc tat aac ccg aaa gtc gat      2297
Met Lys Asn Leu Lys Ile Glu Val Val Arg Tyr Asn Pro Lys Val Asp
            605                 610                 615 acc gca ccg cat agc gca ttc tat gaa gtg cct tat gac gca act acc      2345
Thr Ala Pro His Ser Ala Phe Tyr Glu Val Pro Tyr Asp Ala Thr Thr
620                 625                 630                 635 tca tta ctg gat gcg ctg ggc tac atc aaa gac aac ctg gca ccg gac      2393
Ser Leu Leu Asp Ala Leu Gly Tyr Ile Lys Asp Asn Leu Ala Pro Asp
                640                 645                 650 ctg agc tac cgc tgg tcc tgc cgt atg gcg att tgt ggt tcc tgc ggc      2441
Leu Ser Tyr Arg Trp Ser Cys Arg Met Ala Ile Cys Gly Ser Cys Gly
            655                 660                 665 atg atg gtt aac aac gtg cca aaa ctg gca tgt aaa acc ttc ctg cgt      2489
Met Met Val Asn Asn Val Pro Lys Leu Ala Cys Lys Thr Phe Leu Arg
        670                 675                 680 gat tac acc gac ggt atg aag gtt gaa gcg tta gct aac ttc ccg att      2537
Asp Tyr Thr Asp Gly Met Lys Val Glu Ala Leu Ala Asn Phe Pro Ile
            685                 690                 695 gaa cgc gat ctg gtg gtc gat atg acc cac ttc atc gaa agt ctg gaa      2585
Glu Arg Asp Leu Val Val Asp Met Thr His Phe Ile Glu Ser Leu Glu
700                 705                 710                 715 gcg atc aaa ccg tac atc atc ggc aac tcc cgc acc gcg gat cag ggt      2633
Ala Ile Lys Pro Tyr Ile Ile Gly Asn Ser Arg Thr Ala Asp Gln Gly
                720                 725                 730 act aac atc cag acc ccg gcg cag atg gcg aag tat cac cag ttc tcc      2681
Thr Asn Ile Gln Thr Pro Ala Gln Met Ala Lys Tyr His Gln Phe Ser
            735                 740                 745 ggt tgc atc aac tgt ggt ttg tgc tac gcc gcg tgc ccg cag ttt ggc      2729
Gly Cys Ile Asn Cys Gly Leu Cys Tyr Ala Ala Cys Pro Gln Phe Gly
        750                 755                 760 ctg aac cca gag ttc atc ggt ccg gct gcc att acg ctg gcg cat cgt      2777
Leu Asn Pro Glu Phe Ile Gly Pro Ala Ala Ile Thr Leu Ala His Arg
            765                 770                 775 tat aac gaa gat agc cgc gac cac ggt aag aag gag cgt atg gcg cag      2825
Tyr Asn Glu Asp Ser Arg Asp His Gly Lys Lys Glu Arg Met Ala Gln
```

-continued

```
                780                 785                 790                 795
ttg aac agc cag aac ggc gta tgg agc tgt act ttc gtg ggc tac tgc         2873
Leu Asn Ser Gln Asn Gly Val Trp Ser Cys Thr Phe Val Gly Tyr Cys
                    800                 805                 810 tcc gaa gtc tgc ccg aaa cac gtc gat ccg gct gcg gcc att cag cag         2921
Ser Glu Val Cys Pro Lys His Val Asp Pro Ala Ala Ala Ile Gln Gln
            815                 820                 825 ggc aaa gta gaa agt tcg aaa gac ttt ctt atc gcg acc ctg aaa cca         2969
Gly Lys Val Glu Ser Ser Lys Asp Phe Leu Ile Ala Thr Leu Lys Pro
        830                 835                 840 cgc taaggagtgc aac atg acg act aaa cgt aaa ccg tat gta cgg cca          3018
Arg              Met Thr Thr Lys Arg Lys Pro Tyr Val Arg Pro
                         845                 850                 855 atg acg tcc acc tgg tgg aaa aaa ttg ccg ttt tat cgc ttt tac atg         3066
Met Thr Ser Thr Trp Trp Lys Lys Leu Pro Phe Tyr Arg Phe Tyr Met
                    860                 865                 870 ctg cgc gaa ggc acg gcg gtt ccg gct gtg tgg ttc agc att gaa ctg         3114
Leu Arg Glu Gly Thr Ala Val Pro Ala Val Trp Phe Ser Ile Glu Leu
                875                 880                 885 att ttc ggg ctg ttt gcc ctg aaa aat ggc ccg gaa gcc tgg gcg gga         3162
Ile Phe Gly Leu Phe Ala Leu Lys Asn Gly Pro Glu Ala Trp Ala Gly
            890                 895                 900 ttc gtc gac ttt tta caa aac ccg gtt atc gtg atc att aac ctg atc         3210
Phe Val Asp Phe Leu Gln Asn Pro Val Ile Val Ile Ile Asn Leu Ile
        905                 910                 915 act ctg gcg gca gct ctg ctg cac acc aaa acc tgg ttt gaa ctg gca         3258
Thr Leu Ala Ala Ala Leu Leu His Thr Lys Thr Trp Phe Glu Leu Ala
920                 925                 930                 935 ccg aaa gcg gcc aat atc att gta aaa gac gaa aaa atg gga cca gag         3306
Pro Lys Ala Ala Asn Ile Ile Val Lys Asp Glu Lys Met Gly Pro Glu
                    940                 945                 950 cca att atc aaa agt ctc tgg gcg gta act gtg gtt gcc acc atc gta         3354
Pro Ile Ile Lys Ser Leu Trp Ala Val Thr Val Val Ala Thr Ile Val
                955                 960                 965 atc ctg ttt gtt gcc ctg tac tgg taaggagcct gag atg att aat cca          3403
Ile Leu Phe Val Ala Leu Tyr Trp              Met Ile Asn Pro
            970                 975 aat cca aag cgt tct gac gaa ccg gta ttc tgg ggc ctc ttc ggg gcc         3451
Asn Pro Lys Arg Ser Asp Glu Pro Val Phe Trp Gly Leu Phe Gly Ala
980                 985                 990                 995 ggt ggt atg tgg agc gcc atc att gcg ccg gtg atg atc ctg ctg gtg         3499
Gly Gly Met Trp Ser Ala Ile Ile Ala Pro Val Met Ile Leu Leu Val
                    1000                1005                1010 ggt att ctg ctg cca ctg ggg ttg ttt ccg ggt gat gcg ctg agc tac         3547
Gly Ile Leu Leu Pro Leu Gly Leu Phe Pro Gly Asp Ala Leu Ser Tyr
                1015                1020                1025 gag cgc gtt ctg gcg ttc gcg cag agc ttc att ggt cgc gta ttc ctg         3595
Glu Arg Val Leu Ala Phe Ala Gln Ser Phe Ile Gly Arg Val Phe Leu
            1030                1035                1040 ttc ctg atg atc gtt ctg ccg ctg tgg tgt ggt tta cac cgt atg cac         3643
Phe Leu Met Ile Val Leu Pro Leu Trp Cys Gly Leu His Arg Met His
        1045                1050                1055 cac gcg atg cac gat ctg aaa atc cac gta cct gcg ggc aaa tgg gtt         3691
His Ala Met His Asp Leu Lys Ile His Val Pro Ala Gly Lys Trp Val
1060                1065                1070                1075 ttc tac ggt ctg gct gct atc ctg aca gtt gtc acg ctg att ggt gtc         3739
Phe Tyr Gly Leu Ala Ala Ile Leu Thr Val Val Thr Leu Ile Gly Val
                    1080                1085                1090 gtt aca atc taacgcatcg ccaatgtaaa tccggcccgc ctatggcggg                 3788
Val Thr Ile
```

Val Thr Ile ccgttttgta tggaaaccag accctatgtt caaaacgacg ctctgcgcct tttaatacc      3847

<210> SEQ ID NO 20
<211> LENGTH: 600
<212> TYPE: PRT
<213> ORGANISM: Escherichia coli

<400> SEQUENCE: 20

Val Gln Thr Phe Gln Ala Asp Leu Ala Ile Val Gly Ala Gly Gly Ala
 1               5                  10                  15

Gly Leu Arg Ala Ala Ile Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
        195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255

Asn Lys Asn Gly Tyr Arg Tyr Leu Gln Asp Tyr Gly Met Gly Pro Glu
            260                 265                 270

Thr Pro Leu Gly Glu Pro Lys Asn Lys Tyr Met Glu Leu Gly Pro Arg
        275                 280                 285

Asp Lys Val Ser Gln Ala Phe Trp His Glu Trp Arg Lys Gly Asn Thr
    290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
            340                 345                 350

Pro Thr Ala His Tyr Thr Met Gly Gly Ile Glu Thr Asp Gln Asn Cys

```
                355                 360                 365
Glu Thr Arg Ile Lys Gly Leu Phe Ala Val Gly Glu Cys Ser Ser Val
    370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415

Thr Ala Gly Asn Gly Asn Glu Ala Ala Ile Glu Ala Gln Ala Ala Gly
            420                 425                 430

Val Glu Gln Arg Leu Lys Asp Leu Val Asn Gln Asp Gly Gly Glu Asn
        435                 440                 445

Trp Ala Lys Ile Arg Asp Glu Met Gly Leu Ala Met Glu Glu Gly Cys
    450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
            500                 505                 510

Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
    530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala
        595                 600

<210> SEQ ID NO 21
<211> LENGTH: 244
<212> TYPE: PRT
<213> ORGANISM: Escherichia coli

<400> SEQUENCE: 21

Met Ala Glu Met Lys Asn Leu Lys Ile Glu Val Val Arg Tyr Asn Pro
1               5                   10                  15

Lys Val Asp Thr Ala Pro His Ser Ala Phe Tyr Glu Val Pro Tyr Asp
                20                  25                  30

Ala Thr Thr Ser Leu Leu Asp Ala Leu Gly Tyr Ile Lys Asp Asn Leu
            35                  40                  45

Ala Pro Asp Leu Ser Tyr Arg Trp Ser Cys Arg Met Ala Ile Cys Gly
        50                  55                  60

Ser Cys Gly Met Met Val Asn Asn Val Pro Lys Leu Ala Cys Lys Thr
65                  70                  75                  80

Phe Leu Arg Asp Tyr Thr Asp Gly Met Lys Val Glu Ala Leu Ala Asn
                85                  90                  95

Phe Pro Ile Glu Arg Asp Leu Val Val Asp Met Thr His Phe Ile Glu
            100                 105                 110

Ser Leu Glu Ala Ile Lys Pro Tyr Ile Ile Gly Asn Ser Arg Thr Ala
        115                 120                 125
```

```
Asp Gln Gly Thr Asn Ile Gln Thr Pro Ala Gln Met Ala Lys Tyr His
            130                 135                 140

Gln Phe Ser Gly Cys Ile Asn Cys Gly Leu Cys Tyr Ala Ala Cys Pro
145                 150                 155                 160

Gln Phe Gly Leu Asn Pro Glu Phe Ile Gly Pro Ala Ala Ile Thr Leu
                165                 170                 175

Ala His Arg Tyr Asn Glu Asp Ser Arg Asp His Gly Lys Lys Glu Arg
            180                 185                 190

Met Ala Gln Leu Asn Ser Gln Asn Gly Val Trp Ser Cys Thr Phe Val
        195                 200                 205

Gly Tyr Cys Ser Glu Val Cys Pro Lys His Val Asp Pro Ala Ala Ala
    210                 215                 220

Ile Gln Gln Gly Lys Val Glu Ser Ser Lys Asp Phe Leu Ile Ala Thr
225                 230                 235                 240

Leu Lys Pro Arg
```

<210> SEQ ID NO 22
<211> LENGTH: 131
<212> TYPE: PRT
<213> ORGANISM: Escherichia coli

<400> SEQUENCE: 22

```
Met Thr Thr Lys Arg Lys Pro Tyr Val Arg Pro Met Thr Ser Thr Trp
1               5                   10                  15

Trp Lys Lys Leu Pro Phe Tyr Arg Phe Tyr Met Leu Arg Glu Gly Thr
            20                  25                  30

Ala Val Pro Ala Val Trp Phe Ser Ile Glu Leu Ile Phe Gly Leu Phe
        35                  40                  45

Ala Leu Lys Asn Gly Pro Glu Ala Trp Ala Gly Phe Val Asp Phe Leu
    50                  55                  60

Gln Asn Pro Val Ile Val Ile Asn Leu Ile Thr Leu Ala Ala Ala
65                  70                  75                  80

Leu Leu His Thr Lys Thr Trp Phe Glu Leu Ala Pro Lys Ala Ala Asn
                85                  90                  95

Ile Ile Val Lys Asp Glu Lys Met Gly Pro Glu Pro Ile Ile Lys Ser
            100                 105                 110

Leu Trp Ala Val Thr Val Val Ala Thr Ile Val Ile Leu Phe Val Ala
        115                 120                 125

Leu Tyr Trp
    130
```

<210> SEQ ID NO 23
<211> LENGTH: 119
<212> TYPE: PRT
<213> ORGANISM: Escherichia coli

<400> SEQUENCE: 23

```
Met Ile Asn Pro Asn Pro Lys Arg Ser Asp Glu Pro Val Phe Trp Gly
1               5                   10                  15

Leu Phe Gly Ala Gly Gly Met Trp Ser Ala Ile Ile Ala Pro Val Met
            20                  25                  30

Ile Leu Leu Val Gly Ile Leu Leu Pro Leu Gly Leu Phe Pro Gly Asp
        35                  40                  45

Ala Leu Ser Tyr Glu Arg Val Leu Ala Phe Ala Gln Ser Phe Ile Gly
    50                  55                  60

Arg Val Phe Leu Phe Leu Met Ile Val Leu Pro Leu Trp Cys Gly Leu
```

```
                65                  70                  75                  80
His Arg Met His His Ala Met His Asp Leu Lys Ile His Val Pro Ala
                    85                  90                  95

Gly Lys Trp Val Phe Tyr Gly Leu Ala Ala Ile Leu Thr Val Val Thr
                100                 105                 110

Leu Ile Gly Val Val Thr Ile
        115

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atatgaaacc cggtac                                                       16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgggtttcat atgtac                                                       16

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggttcccggg gaggaggaat cccatgccca acc                                    33

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggttcccggg ggcacctacg gtgcaacagt tg                                     32

<210> SEQ ID NO 28
<211> LENGTH: 4123
<212> TYPE: DNA
<213> ORGANISM: Brevibacterium flavum
<220> FEATURE:
<221> NAME/KEY: CDS
<222> LOCATION: (363)..(1133)
<220> FEATURE:
<221> NAME/KEY: CDS
<222> LOCATION: (1153)..(3171)
<220> FEATURE:
<221> NAME/KEY: CDS
<222> LOCATION: (3174)..(3920)

<400> SEQUENCE: 28
```

-continued

```
ggttcccggg ggcacctacg gtgcaacagt tgcgaaaatt gtgtcacctg cgcaaagcct      60
tgcttcgatt cggggaattc gggtgtctaa acttttgat tgataccaaa cggggttaga     120
aactgttcgg atcggtatcc tgtgaggaag ctcaccttgg ttttagaatg ttgaaaaagc     180
ctcaggtttc cgcaggtaga gcacactcaa ttaaatgagc gtcaaacgac aataaagtaa     240
ggctacccta ataagtgggg ttttatgcct ctaaatagcc agttggggc ggtaggggag      300 cgtcccatga ctggttaatg cctcgatctg ggacgtacag taacaacgac actggaggtg     360
```

```
cc atg act gtt aga aat ccc gac cgt gag gca atc cgt cac gga aaa        407
   Met Thr Val Arg Asn Pro Asp Arg Glu Ala Ile Arg His Gly Lys
     1               5                   10                  15 att acg acg gag gcg ctg cgt gag cgt ccc gca tac ccg acc tgg gca       455
Ile Thr Thr Glu Ala Leu Arg Glu Arg Pro Ala Tyr Pro Thr Trp Ala
                20                  25                  30 atg aag ctg acc atg gcc atc act ggc cta atc ttc ggt ggc ttc gtt       503
Met Lys Leu Thr Met Ala Ile Thr Gly Leu Ile Phe Gly Gly Phe Val
            35                  40                  45 ctt gtt cac atg atc gga aac ctg aaa atc ttc atg ccg gac tac gca       551
Leu Val His Met Ile Gly Asn Leu Lys Ile Phe Met Pro Asp Tyr Ala
        50                  55                  60 gcc gat tct gcg cat ccg ggt gaa gca caa gta gat gtc tac ggc gag       599
Ala Asp Ser Ala His Pro Gly Glu Ala Gln Val Asp Val Tyr Gly Glu
    65                  70                  75 ttc ctg cgc gag atc gga tcc ccg atc ctc cca cac ggc tca gtc ctc       647
Phe Leu Arg Glu Ile Gly Ser Pro Ile Leu Pro His Gly Ser Val Leu
 80                  85                  90                  95 tgg atc cta cgt att atc ctg ctg gtc gca ttg gtt ctg cac atc tac       695
Trp Ile Leu Arg Ile Ile Leu Leu Val Ala Leu Val Leu His Ile Tyr
                    100                 105                 110 tgt gca ttc gca ttg acc ggc cgt tct cac cag tct cgc gga aag ttc       743
Cys Ala Phe Ala Leu Thr Gly Arg Ser His Gln Ser Arg Gly Lys Phe
                115                 120                 125 cgc cgt acc aac ctc gtt ggc ggc ttc aac tcc ttc gcg acc cgc tcc       791
Arg Arg Thr Asn Leu Val Gly Gly Phe Asn Ser Phe Ala Thr Arg Ser
            130                 135                 140 atg ctg gtg acc gga atc gtt ctc ctt gcg ttc att atc ttc cac atc       839
Met Leu Val Thr Gly Ile Val Leu Leu Ala Phe Ile Ile Phe His Ile
        145                 150                 155 ctc gac ctg acc atg ggt gtt gct cca gca gcc cca acc tca ttc gag       887
Leu Asp Leu Thr Met Gly Val Ala Pro Ala Ala Pro Thr Ser Phe Glu
160                 165                 170                 175 cac ggc gaa gta tac gca aac atg gtg gct tcc ttt agc cgc tgg cct       935
His Gly Glu Val Tyr Ala Asn Met Val Ala Ser Phe Ser Arg Trp Pro
                    180                 185                 190 gta gca att tgg tac atc att gcc aac ctg gtc ctg ttc gtc cac ctg       983
Val Ala Ile Trp Tyr Ile Ile Ala Asn Leu Val Leu Phe Val His Leu
                195                 200                 205 tct cac ggc atc tgg ctt gca gtc tct gac ctg gga atc acc gga cgt      1031
Ser His Gly Ile Trp Leu Ala Val Ser Asp Leu Gly Ile Thr Gly Arg
            210                 215                 220 cgc tgg agg gca atc ctc ctc gca gtt gcg tac atc gtt cct gca ctg      1079
Arg Trp Arg Ala Ile Leu Leu Ala Val Ala Tyr Ile Val Pro Ala Leu
        225                 230                 235 gtc ctg atc ggc aac atc acc att ccg ttc gcc atc gct gtt ggc tgg      1127
Val Leu Ile Gly Asn Ile Thr Ile Pro Phe Ala Ile Ala Val Gly Trp
240                 245                 250                 255 att gcg taaaggttag gaagaattt atg agc act cac tct gaa acc acc cgc     1179
Ile Ala                         Met Ser Thr His Ser Glu Thr Thr Arg
```

-continued

|  |  |  | 260 |  |  |  | 265 |  |  |  |  |  |
|---|---|---|---|---|---|---|---|---|---|---|---|---|

```
cca gag ttc atc cac cca gtc tcc gtc ctc cca gag gtc tca gct ggt      1227
Pro Glu Phe Ile His Pro Val Ser Val Leu Pro Glu Val Ser Ala Gly
            270                 275                 280 acg gtc ctt gac gct gca gag cca gct ggt gtt ccc acc aaa gac atg      1275
Thr Val Leu Asp Ala Ala Glu Pro Ala Gly Val Pro Thr Lys Asp Met
        285                 290                 295 tgg gaa tac caa aaa gac cac atg aac ctg gtc tcc cca ctg aac cga      1323
Trp Glu Tyr Gln Lys Asp His Met Asn Leu Val Ser Pro Leu Asn Arg
300                 305                 310 cgc aag ttc cgc gtc ctc gtc gtc ggc acc ggc ctg tcc ggt ggc gct      1371
Arg Lys Phe Arg Val Leu Val Val Gly Thr Gly Leu Ser Gly Gly Ala
            315                 320                 325                 330 gca gca gca gcc ctc ggc gaa ctc gga tac gac gtc aag gcg ttc acc      1419
Ala Ala Ala Ala Leu Gly Glu Leu Gly Tyr Asp Val Lys Ala Phe Thr
                    335                 340                 345 tac cac gac gca cct cgc cgt gcg cac tcc att gct gcg cag ggt ggc      1467
Tyr His Asp Ala Pro Arg Arg Ala His Ser Ile Ala Ala Gln Gly Gly
        350                 355                 360 gtt aac tcc gcc cgc ggc aag aag gta gac aac gac ggc gca tac cgc      1515
Val Asn Ser Ala Arg Gly Lys Lys Val Asp Asn Asp Gly Ala Tyr Arg
        365                 370                 375 cac gtc aag gac acc gtc aag ggc ggc gac tac cgt ggc cgc gag tcc      1563
His Val Lys Asp Thr Val Lys Gly Gly Asp Tyr Arg Gly Arg Glu Ser
380                 385                 390 gac tgc tgg cgt ctc gcc gtc gag tcc gtc cgc gtc atc gac cac atg      1611
Asp Cys Trp Arg Leu Ala Val Glu Ser Val Arg Val Ile Asp His Met
395                 400                 405                 410 aat gcc atc ggt gcg cca ttc gcc cgc gaa tac ggt ggc gcc ttg gca      1659
Asn Ala Ile Gly Ala Pro Phe Ala Arg Glu Tyr Gly Gly Ala Leu Ala
                    415                 420                 425 acc cgt tcc ttc ggt ggt gtg cag gtc tcc cgt acc tac tac acc cgt      1707
Thr Arg Ser Phe Gly Gly Val Gln Val Ser Arg Thr Tyr Tyr Thr Arg
        430                 435                 440 gga caa acc gga cag cag ctg cag ctc tcc acc gca tcc gca cta cag      1755
Gly Gln Thr Gly Gln Gln Leu Gln Leu Ser Thr Ala Ser Ala Leu Gln
        445                 450                 455 cgc cag atc cac ctc ggc tcc gta gag atc ttc acc cac aac gaa atg      1803
Arg Gln Ile His Leu Gly Ser Val Glu Ile Phe Thr His Asn Glu Met
    460                 465                 470 gtt gac gtc att gtc acc gaa cgt aat ggt gaa aag cgc tgc gaa ggc      1851
Val Asp Val Ile Val Thr Glu Arg Asn Gly Glu Lys Arg Cys Glu Gly
475                 480                 485                 490 ctg atc atg cgc aac ctg atc acc ggc gag ctc acc gca cac acc ggc      1899
Leu Ile Met Arg Asn Leu Ile Thr Gly Glu Leu Thr Ala His Thr Gly
                    495                 500                 505 cat gcc gtt atc ctg gca acc ggt ggt tac ggc aac gtg tac cac atg      1947
His Ala Val Ile Leu Ala Thr Gly Gly Tyr Gly Asn Val Tyr His Met
        510                 515                 520 tcc acc ctg gcg aag aac tcc aac gcc tcg gcc atc atg cgt gca tac      1995
Ser Thr Leu Ala Lys Asn Ser Asn Ala Ser Ala Ile Met Arg Ala Tyr
        525                 530                 535 gaa gcc ggc gca tac ttc gcg tcc cca tcg ttc atc cag ttc cac cca      2043
Glu Ala Gly Ala Tyr Phe Ala Ser Pro Ser Phe Ile Gln Phe His Pro
    540                 545                 550 acc ggc ctg cct gtg aac tcc acc tgg cag tcc aag acc att ctg atg      2091
Thr Gly Leu Pro Val Asn Ser Thr Trp Gln Ser Lys Thr Ile Leu Met
555                 560                 565                 570 tcc gag tcg ctg cgt aac gac ggc cgc atc tgg tcc cct aag gaa ccg      2139
```

```
            Ser Glu Ser Leu Arg Asn Asp Gly Arg Ile Trp Ser Pro Lys Glu Pro
                        575                 580                 585 aac gat aac cgc gat cca aac acc atc cct gag gat gag cgc gac tac          2187
Asn Asp Asn Arg Asp Pro Asn Thr Ile Pro Glu Asp Glu Arg Asp Tyr
                590                 595                 600 ttc ctg gag cgc cgc tac cca gca ttc ggt aac ctc gtc cca cgt gac          2235
Phe Leu Glu Arg Arg Tyr Pro Ala Phe Gly Asn Leu Val Pro Arg Asp
            605                 610                 615 gtt gct tcc cgt gcg atc tcc cag cag atc aac gct ggt ctc ggt gtt          2283
Val Ala Ser Arg Ala Ile Ser Gln Gln Ile Asn Ala Gly Leu Gly Val
        620                 625                 630 gga cct ctg aac aac gct gca tac ctg gac ttc cgc gac gcc acc gag          2331
Gly Pro Leu Asn Asn Ala Ala Tyr Leu Asp Phe Arg Asp Ala Thr Glu
635                 640                 645                 650 cgt ctc gga cag gac acc atc cgc gag cgt tac tcc aac ctc ttc acc          2379
Arg Leu Gly Gln Asp Thr Ile Arg Glu Arg Tyr Ser Asn Leu Phe Thr
                655                 660                 665 atg tac gaa gag gcc att ggc gag gac cca tac tcc agc cca atg cgt          2427
Met Tyr Glu Glu Ala Ile Gly Glu Asp Pro Tyr Ser Ser Pro Met Arg
            670                 675                 680 att gca ccg acc tgc cac ttc acc atg ggt ggc ctc tgg act gac ttc          2475
Ile Ala Pro Thr Cys His Phe Thr Met Gly Gly Leu Trp Thr Asp Phe
        685                 690                 695 aac gaa atg acg tca ctc cca ggt ctg ttc tgt gca ggc gaa gca tcc          2523
Asn Glu Met Thr Ser Leu Pro Gly Leu Phe Cys Ala Gly Glu Ala Ser
700                 705                 710 tgg acc tac cac ggt gca aac cgt ctg ggc gca aac tcc ctc tcc              2571
Trp Thr Tyr His Gly Ala Asn Arg Leu Gly Ala Asn Ser Leu Leu Ser
715                 720                 725                 730 gct tcc gtc gat ggc tgg ttc acc ctg cca ttc acc gtc cct aac tac          2619
Ala Ser Val Asp Gly Trp Phe Thr Leu Pro Phe Thr Val Pro Asn Tyr
                735                 740                 745 ctc ggc cca ttg ctt ggc gcc gag cgt ctg gca gag gac gca cca gaa          2667
Leu Gly Pro Leu Leu Gly Ala Glu Arg Leu Ala Glu Asp Ala Pro Glu
            750                 755                 760 gcg cag gcg gcg att gag cgt gca cag gct cgc atc gac cgc ctc atg          2715
Ala Gln Ala Ala Ile Glu Arg Ala Gln Ala Arg Ile Asp Arg Leu Met
        765                 770                 775 ggc aac cgc cca gag tgg atc ggc gac aac cca cac ggc cct gag tac          2763
Gly Asn Arg Pro Glu Trp Ile Gly Asp Asn Pro His Gly Pro Glu Tyr
780                 785                 790 tac cac cgc cag ctt ggc gat atc ctg tac ttc tcc tgt ggc gtt tct          2811
Tyr His Arg Gln Leu Gly Asp Ile Leu Tyr Phe Ser Cys Gly Val Ser
795                 800                 805                 810 cga aac gta aag gac ctc cag gac ggt atc gac aag atc cgt gcg ctc          2859
Arg Asn Val Lys Asp Leu Gln Asp Gly Ile Asp Lys Ile Arg Ala Leu
                815                 820                 825 cgc gag gac ttc tgg aag aac atg cgc atc acc ggc agc acc gat gag          2907
Arg Glu Asp Phe Trp Lys Asn Met Arg Ile Thr Gly Ser Thr Asp Glu
            830                 835                 840 atg aac cag gtt ctc gaa tac gca gca cgc gtt gct gat tac atc gac          2955
Met Asn Gln Val Leu Glu Tyr Ala Ala Arg Val Ala Asp Tyr Ile Asp
        845                 850                 855 ctc ggc gaa ctc atg tgc gtc gac gcc ctc gac cgc gac gag tcc tgt          3003
Leu Gly Glu Leu Met Cys Val Asp Ala Leu Asp Arg Asp Glu Ser Cys
860                 865                 870 ggc gcc cac ttc cgt gac gac cac ctc tcc gaa gac ggc gaa gca gaa          3051
Gly Ala His Phe Arg Asp Asp His Leu Ser Glu Asp Gly Glu Ala Glu
875                 880                 885                 890
```

```
cgt gac gac gaa aac tgg tgc ttc gtc tcc gca tgg gaa cca ggc aag    3099
Arg Asp Asp Glu Asn Trp Cys Phe Val Ser Ala Trp Glu Pro Gly Lys
                895                 900                 905 aac gga acc ttc gtc cgc cac gca gaa cca ctg ttc ttc gaa tcc gtc    3147
Asn Gly Thr Phe Val Arg His Ala Glu Pro Leu Phe Phe Glu Ser Val
            910                 915                 920 cca ctg cag aca agg aac tac aag ta atg aaa ctt aca ctt gag atc     3194
Pro Leu Gln Thr Arg Asn Tyr Lys     Met Lys Leu Thr Leu Glu Ile
        925                 930                 935 tgg cgt cag gca ggc cca act gca gaa ggc aag ttc gaa acc gta cgg    3242
Trp Arg Gln Ala Gly Pro Thr Ala Glu Gly Lys Phe Glu Thr Val Arg
    940                 945                 950 gtt gac gac gcc gtc gcg cag atg tct atc ctg gaa ctg cta gac cac    3290
Val Asp Asp Ala Val Ala Gln Met Ser Ile Leu Glu Leu Leu Asp His
955                 960                 965 gta aac aac aag ttc atc gaa gaa ggc aag gaa cca ttc gcg ttc gcc    3338
Val Asn Asn Lys Phe Ile Glu Glu Gly Lys Glu Pro Phe Ala Phe Ala
970                 975                 980                 985 tct gac tgc cgc gaa ggc atc tgt ggt acc tgt ggt ctc ctc gtg aac    3386
Ser Asp Cys Arg Glu Gly Ile Cys Gly Thr Cys Gly Leu Leu Val Asn
            990                 995                 1000 ggt cgc cct cac ggc gcc gac cag aac aag cct gcc tgt gcg cag cgc    3434
Gly Arg Pro His Gly Ala Asp Gln Asn Lys Pro Ala Cys Ala Gln Arg
        1005                1010                1015 ctg gtc agc tac aag gaa ggc gac acc ctt aag att gag cca ctg cgc    3482
Leu Val Ser Tyr Lys Glu Gly Asp Thr Leu Lys Ile Glu Pro Leu Arg
    1020                1025                1030 tcc gcc gca tac cca gtg atc aag gac atg gtc gtc gac cgc tcc gca    3530
Ser Ala Ala Tyr Pro Val Ile Lys Asp Met Val Val Asp Arg Ser Ala
1035                1040                1045 ctg gac cgc gtc atg gaa cag ggt ggc tac gtg acc atc aac gca ggt    3578
Leu Asp Arg Val Met Glu Gln Gly Gly Tyr Val Thr Ile Asn Ala Gly
1050                1055                1060                1065 acc gca cct gac gct gat acc ctc cac gtc aac cac gaa acc gca gaa    3626
Thr Ala Pro Asp Ala Asp Thr Leu His Val Asn His Glu Thr Ala Glu
            1070                1075                1080 ctc gca ctt gac cac gca gcc tgc atc ggc tgt ggt gca tgt gtc gct    3674
Leu Ala Leu Asp His Ala Ala Cys Ile Gly Cys Gly Ala Cys Val Ala
        1085                1090                1095 gcc tgc cct aac ggc gca gca cac ctg ttc acc ggc gca aag ctt gtt    3722
Ala Cys Pro Asn Gly Ala Ala His Leu Phe Thr Gly Ala Lys Leu Val
    1100                1105                1110 cac ctc tcc ctc ctc cca cta ggt aag gaa gag cgc gga ctg cgt gca    3770
His Leu Ser Leu Leu Pro Leu Gly Lys Glu Glu Arg Gly Leu Arg Ala
1115                1120                1125 cgt aag atg gtt gat gaa atg gaa acc aac ttc gga cac tgc tcc ctc    3818
Arg Lys Met Val Asp Glu Met Glu Thr Asn Phe Gly His Cys Ser Leu
1130                1135                1140                1145 tac ggc gag tgc gca gac gtt tgc ccc gca ggc atc cca ctg acc gct    3866
Tyr Gly Glu Cys Ala Asp Val Cys Pro Ala Gly Ile Pro Leu Thr Ala
            1150                1155                1160 gtg gca gct gtc acc aaa gaa cgt gcg cgt gca gct ttc cga ggc aaa    3914
Val Ala Ala Val Thr Lys Glu Arg Ala Arg Ala Ala Phe Arg Gly Lys
        1165                1170                1175 gac gac tagtctttaa tccaagtaag taccggttca gacagttaaa ccagaaagac    3970
Asp Asp gagtgaacac catgtcctcc gcgaaaaaga aacccgcacc ggagcgtatg cactacatca   4030
agggctatgt acctgtggcg tatagctctc cacactcatc cctcgagcgc agcgcaacct   4090
```
ggttgggcat gggattcctc ctccccggga acc                                    4123

<210> SEQ ID NO 29
<211> LENGTH: 257
<212> TYPE: PRT
<213> ORGANISM: Brevibacterium flavum

<400> SEQUENCE: 29

Met Thr Val Arg Asn Pro Asp Arg Glu Ala Ile Arg His Gly Lys Ile
1               5                   10                  15

Thr Thr Glu Ala Leu Arg Glu Arg Pro Ala Tyr Pro Thr Trp Ala Met
            20                  25                  30

Lys Leu Thr Met Ala Ile Thr Gly Leu Ile Phe Gly Gly Phe Val Leu
        35                  40                  45

Val His Met Ile Gly Asn Leu Lys Ile Phe Met Pro Asp Tyr Ala Ala
    50                  55                  60

Asp Ser Ala His Pro Gly Glu Ala Gln Val Asp Val Tyr Gly Glu Phe
65                  70                  75                  80

Leu Arg Glu Ile Gly Ser Pro Ile Leu Pro His Gly Ser Val Leu Trp
                85                  90                  95

Ile Leu Arg Ile Ile Leu Leu Val Ala Leu Val Leu His Ile Tyr Cys
            100                 105                 110

Ala Phe Ala Leu Thr Gly Arg Ser His Gln Ser Arg Gly Lys Phe Arg
        115                 120                 125

Arg Thr Asn Leu Val Gly Gly Phe Asn Ser Phe Ala Thr Arg Ser Met
    130                 135                 140

Leu Val Thr Gly Ile Val Leu Ala Phe Ile Ile Phe His Ile Leu
145                 150                 155                 160

Asp Leu Thr Met Gly Val Ala Pro Ala Pro Thr Ser Phe Glu His
                165                 170                 175

Gly Glu Val Tyr Ala Asn Met Val Ala Ser Phe Ser Arg Trp Pro Val
            180                 185                 190

Ala Ile Trp Tyr Ile Ile Ala Asn Leu Val Leu Phe Val His Leu Ser
        195                 200                 205

His Gly Ile Trp Leu Ala Val Ser Asp Leu Gly Ile Thr Gly Arg Arg
    210                 215                 220

Trp Arg Ala Ile Leu Leu Ala Val Ala Tyr Ile Val Pro Ala Leu Val
225                 230                 235                 240

Leu Ile Gly Asn Ile Thr Ile Pro Phe Ala Ile Ala Val Gly Trp Ile
                245                 250                 255

Ala

<210> SEQ ID NO 30
<211> LENGTH: 673
<212> TYPE: PRT
<213> ORGANISM: Brevibacterium flavum

<400> SEQUENCE: 30

Met Ser Thr His Ser Glu Thr Thr Arg Pro Glu Phe Ile His Pro Val
1               5                   10                  15

Ser Val Leu Pro Glu Val Ser Ala Gly Thr Val Leu Asp Ala Ala Glu
            20                  25                  30

Pro Ala Gly Val Pro Thr Lys Asp Met Trp Glu Tyr Gln Lys Asp His
        35                  40                  45

Met Asn Leu Val Ser Pro Leu Asn Arg Arg Lys Phe Arg Val Leu Val
    50                  55                  60

-continued

```
Val Gly Thr Gly Leu Ser Gly Ala Ala Ala Ala Leu Gly Glu
 65                  70                  75                  80

Leu Gly Tyr Asp Val Lys Ala Phe Thr Tyr His Asp Ala Pro Arg Arg
                 85                  90                  95

Ala His Ser Ile Ala Ala Gln Gly Gly Val Asn Ser Ala Arg Gly Lys
            100                 105                 110

Lys Val Asp Asn Asp Gly Ala Tyr Arg His Val Lys Asp Thr Val Lys
        115                 120                 125

Gly Gly Asp Tyr Arg Gly Arg Glu Ser Asp Cys Trp Arg Leu Ala Val
    130                 135                 140

Glu Ser Val Arg Val Ile Asp His Met Asn Ala Ile Gly Ala Pro Phe
145                 150                 155                 160

Ala Arg Glu Tyr Gly Gly Ala Leu Ala Thr Arg Ser Phe Gly Gly Val
                165                 170                 175

Gln Val Ser Arg Thr Tyr Tyr Thr Arg Gly Gln Thr Gly Gln Gln Leu
            180                 185                 190

Gln Leu Ser Thr Ala Ser Ala Leu Gln Arg Gln Ile His Leu Gly Ser
        195                 200                 205

Val Glu Ile Phe Thr His Asn Glu Met Val Asp Val Ile Val Thr Glu
    210                 215                 220

Arg Asn Gly Glu Lys Arg Cys Glu Gly Leu Ile Met Arg Asn Leu Ile
225                 230                 235                 240

Thr Gly Glu Leu Thr Ala His Thr Gly His Ala Val Ile Leu Ala Thr
                245                 250                 255

Gly Gly Tyr Gly Asn Val Tyr His Met Ser Thr Leu Ala Lys Asn Ser
            260                 265                 270

Asn Ala Ser Ala Ile Met Arg Ala Tyr Glu Ala Gly Ala Tyr Phe Ala
        275                 280                 285

Ser Pro Ser Phe Ile Gln Phe His Pro Thr Gly Leu Pro Val Asn Ser
    290                 295                 300

Thr Trp Gln Ser Lys Thr Ile Leu Met Ser Glu Ser Leu Arg Asn Asp
305                 310                 315                 320

Gly Arg Ile Trp Ser Pro Lys Glu Pro Asn Asp Asn Arg Asp Pro Asn
                325                 330                 335

Thr Ile Pro Glu Asp Glu Arg Asp Tyr Phe Leu Glu Arg Arg Tyr Pro
            340                 345                 350

Ala Phe Gly Asn Leu Val Pro Arg Asp Val Ala Ser Arg Ala Ile Ser
        355                 360                 365

Gln Gln Ile Asn Ala Gly Leu Gly Val Gly Pro Leu Asn Asn Ala Ala
    370                 375                 380

Tyr Leu Asp Phe Arg Asp Ala Thr Glu Arg Leu Gly Gln Asp Thr Ile
385                 390                 395                 400

Arg Glu Arg Tyr Ser Asn Leu Phe Thr Met Tyr Glu Glu Ala Ile Gly
                405                 410                 415

Glu Asp Pro Tyr Ser Ser Pro Met Arg Ile Ala Pro Thr Cys His Phe
            420                 425                 430

Thr Met Gly Gly Leu Trp Thr Asp Phe Asn Glu Met Thr Ser Leu Pro
        435                 440                 445

Gly Leu Phe Cys Ala Gly Glu Ala Ser Trp Thr Tyr His Gly Ala Asn
    450                 455                 460

Arg Leu Gly Ala Asn Ser Leu Leu Ser Ala Ser Val Asp Gly Trp Phe
465                 470                 475                 480
```

```
Thr Leu Pro Phe Thr Val Pro Asn Tyr Leu Gly Pro Leu Leu Gly Ala
            485                 490                 495

Glu Arg Leu Ala Glu Asp Ala Pro Glu Ala Gln Ala Ala Ile Glu Arg
            500                 505                 510

Ala Gln Ala Arg Ile Asp Arg Leu Met Gly Asn Arg Pro Glu Trp Ile
            515                 520                 525

Gly Asp Asn Pro His Gly Pro Glu Tyr Tyr His Arg Gln Leu Gly Asp
            530                 535                 540

Ile Leu Tyr Phe Ser Cys Gly Val Ser Arg Asn Val Lys Asp Leu Gln
545                 550                 555                 560

Asp Gly Ile Asp Lys Ile Arg Ala Leu Arg Glu Asp Phe Trp Lys Asn
                565                 570                 575

Met Arg Ile Thr Gly Ser Thr Asp Glu Met Asn Gln Val Leu Glu Tyr
            580                 585                 590

Ala Ala Arg Val Ala Asp Tyr Ile Asp Leu Gly Glu Leu Met Cys Val
            595                 600                 605

Asp Ala Leu Asp Arg Asp Glu Ser Cys Gly Ala His Phe Arg Asp Asp
            610                 615                 620

His Leu Ser Glu Asp Gly Glu Ala Glu Arg Asp Asp Glu Asn Trp Cys
625                 630                 635                 640

Phe Val Ser Ala Trp Glu Pro Gly Lys Asn Gly Thr Phe Val Arg His
                645                 650                 655

Ala Glu Pro Leu Phe Phe Glu Ser Val Pro Leu Gln Thr Arg Asn Tyr
            660                 665                 670

Lys

<210> SEQ ID NO 31
<211> LENGTH: 249
<212> TYPE: PRT
<213> ORGANISM: Brevibacterium flavum

<400> SEQUENCE: 31

Met Lys Leu Thr Leu Glu Ile Trp Arg Gln Ala Gly Pro Thr Ala Glu
1               5                   10                  15

Gly Lys Phe Glu Thr Val Arg Val Asp Asp Ala Val Ala Gln Met Ser
            20                  25                  30

Ile Leu Glu Leu Leu Asp His Val Asn Asn Lys Phe Ile Glu Glu Gly
        35                  40                  45

Lys Glu Pro Phe Ala Phe Ala Ser Asp Cys Arg Glu Gly Ile Cys Gly
    50                  55                  60

Thr Cys Gly Leu Leu Val Asn Gly Arg Pro His Gly Ala Asp Gln Asn
65              70                  75                  80

Lys Pro Ala Cys Ala Gln Arg Leu Val Ser Tyr Lys Glu Gly Asp Thr
                85                  90                  95

Leu Lys Ile Glu Pro Leu Arg Ser Ala Ala Tyr Pro Val Ile Lys Asp
            100                 105                 110

Met Val Val Asp Arg Ser Ala Leu Asp Arg Val Met Glu Gln Gly Gly
        115                 120                 125

Tyr Val Thr Ile Asn Ala Gly Thr Ala Pro Asp Ala Asp Thr Leu His
    130                 135                 140

Val Asn His Glu Thr Ala Glu Leu Ala Leu Asp His Ala Ala Cys Ile
145                 150                 155                 160

Gly Cys Gly Ala Cys Val Ala Ala Cys Pro Asn Gly Ala Ala His Leu
                165                 170                 175
```

-continued

```
Phe Thr Gly Ala Lys Leu Val His Leu Ser Leu Leu Pro Leu Gly Lys
            180                 185                 190

Glu Glu Arg Gly Leu Arg Ala Arg Lys Met Val Asp Glu Met Glu Thr
        195                 200                 205

Asn Phe Gly His Cys Ser Leu Tyr Gly Glu Cys Ala Asp Val Cys Pro
        210                 215                 220

Ala Gly Ile Pro Leu Thr Ala Val Ala Ala Val Thr Lys Glu Arg Ala
225                 230                 235                 240

Arg Ala Ala Phe Arg Gly Lys Asp Asp
                245
```